US011224857B2

(12) United States Patent
Tamaki et al.

(10) Patent No.: US 11,224,857 B2
(45) Date of Patent: Jan. 18, 2022

(54) METHOD FOR MANUFACTURING WATER ABSORBING AGENT

(71) Applicant: NIPPON SHOKUBAI CO., LTD., Osaka (JP)

(72) Inventors: Mariko Tamaki, Himeji (JP); Kazushi Torii, Himeji (JP); Hiroyuki Ikeuchi, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 374 days.

(21) Appl. No.: 16/089,285

(22) PCT Filed: Mar. 28, 2017

(86) PCT No.: PCT/JP2017/012751
§ 371 (c)(1),
(2) Date: Sep. 27, 2018

(87) PCT Pub. No.: WO2017/170604
PCT Pub. Date: Oct. 5, 2017

(65) Prior Publication Data
US 2019/0105633 A1 Apr. 11, 2019

(30) Foreign Application Priority Data

Mar. 28, 2016 (JP) .............................. JP2016-063762
Sep. 30, 2016 (JP) .............................. JP2016-194920

(51) Int. Cl.
*B01J 20/30* (2006.01)
*A61L 15/20* (2006.01)
*A61L 15/24* (2006.01)
*A61L 15/60* (2006.01)
*B01J 20/26* (2006.01)
*C08L 33/02* (2006.01)
*A61F 13/53* (2006.01)
*C08F 2/44* (2006.01)
*C08K 5/098* (2006.01)
*B01J 20/28* (2006.01)
*C08F 122/20* (2006.01)

(52) U.S. Cl.
CPC ........... *B01J 20/3085* (2013.01); *A61F 13/53* (2013.01); *A61L 15/20* (2013.01); *A61L 15/24* (2013.01); *A61L 15/60* (2013.01); *B01J 20/26* (2013.01); *B01J 20/265* (2013.01); *B01J 20/28* (2013.01); *B01J 20/30* (2013.01); *C08F 2/44* (2013.01); *C08F 122/20* (2013.01); *C08K 5/098* (2013.01); *C08L 33/02* (2013.01)

(58) Field of Classification Search
CPC ........ B01J 20/30; B01J 20/3085; B01J 20/26; B01J 20/265; B01J 20/28; A61F 13/53; A61L 15/20; A61L 15/24; A61L 15/60; C08F 2/44; C08F 22/20; C08K 5/098; C08L 33/02

USPC .......................................................... 502/402
See application file for complete search history.

(56) References Cited

U.S. PATENT DOCUMENTS

| | | | |
|---|---|---|---|
| 4,893,999 A | 1/1990 | Chmelir et al. | |
| 5,669,894 A | 9/1997 | Goldman et al. | |
| 6,241,928 B1 | 6/2001 | Hatsuda et al. | |
| 6,710,141 B1 | 3/2004 | Heide et al. | |
| 6,987,151 B2 | 1/2006 | Gartner et al. | |
| 7,183,456 B2 | 2/2007 | Hatsuda et al. | |
| 7,265,190 B2 | 9/2007 | Dairoku et al. | |
| 7,638,570 B2 | 12/2009 | Torii et al. | |
| 10,363,339 B2* | 7/2019 | Ueda ....................... | A61L 15/46 |
| 2001/0053807 A1 | 12/2001 | Miyake et al. | |
| 2005/0215734 A1 | 9/2005 | Dairoku et al. | |
| 2008/0161512 A1 | 7/2008 | Kawano et al. | |
| 2008/0194863 A1 | 8/2008 | Weismantel et al. | |
| 2012/0178621 A1 | 7/2012 | Elliott et al. | |
| 2015/0258237 A1 | 9/2015 | Machida et al. | |

(Continued)

FOREIGN PATENT DOCUMENTS

| | | |
|---|---|---|
| CN | 1515628 A | 7/2004 |
| CN | 101501131 A | 8/2009 |
| EP | 0942014 A2 | 9/1999 |

(Continued)

OTHER PUBLICATIONS

Extended European Search Report dated Sep. 12, 2019, which issued in the corresponding Application No. 17775141.9.
Edana, Centrifuge Retention Capacity 441.2-02, Recommended Test Method: Superabsorbent materials—Polyacrylate superabsorbent powders—Gravimetric Determination of Fluid Retention Capacity in Saline Solution After Centrifugation, 2002, pp. 303-309.
Edana, Extractables 470.2-02, Recommended Test Method: Superabsorbent materials—Polyacrylate superabsorbent powders—Determination of Extractable Polymer Content by Potentiometric Titration, 2002, pp. 333-339.
Edana, Absorption Under Pressure 442.2-02, Recommended Test Method: Superabsorbent materials—Polyacrylate superabsorbent powders—Gravimetric Determination of Absorption Under Pressure, 2002, pp. 311-317.

(Continued)

*Primary Examiner* — Edward M Johnson
(74) *Attorney, Agent, or Firm* — Dickinson Wright PLLC

(57) ABSTRACT

A water absorbent agent having a high water absorption multiplying factor where stickiness after absorbing liquid can be reduced when used as a hygienic material is produce by a method for manufacturing the water absorbing agent. The method for manufacturing a water absorbent agent having a centrifuge retention capacity (CRC) of 30 g/g or greater, includes subjecting an aqueous solution of a monomer that includes an acrylic acid (salt) to a polymerization step, a drying step, and a surface cross-linking step, and a step for adding α-hydroxycarboxylic acid (salt) before the drying step. The atomic weight of the soluble portion eluted when the water absorbent agent absorbs liquid and swells can be reduced by the α-hydroxycarboxylic acid (salt) before the drying step to reduce the stickiness of the water absorbent agent after absorption of liquid, which leads to discomfort during use of disposable diapers and the like.

8 Claims, 2 Drawing Sheets

(56) References Cited

U.S. PATENT DOCUMENTS

2017/0014801 A1 1/2017 Ikeuchi et al.

FOREIGN PATENT DOCUMENTS

| EP | 1108745 A1 | 6/2001 |
|---|---|---|
| JP | 2010-502768 A | 1/2010 |
| JP | 2010502768 A1 | 1/2010 |
| JP | 5415256 B2 | 11/2013 |
| JP | 5415256 B2 | 2/2014 |
| WO | 2005012369 A1 | 2/2005 |
| WO | 2005016393 A1 | 2/2005 |
| WO | WO 2005/012369 A1 | 2/2005 |
| WO | 2005075070 A1 | 8/2005 |
| WO | 2006100300 A1 | 9/2006 |
| WO | 2008/026772 A1 | 3/2008 |
| WO | 2008026772 A1 | 3/2008 |
| WO | WO 2008/026772 A1 | 3/2008 |
| WO | 2009123197 A1 | 10/2009 |
| WO | 2010502768 A1 | 1/2010 |
| WO | 2011025012 A1 | 3/2011 |
| WO | 2011025013 A1 | 3/2011 |
| WO | 2011040530 A1 | 4/2011 |
| WO | 2011111657 A1 | 9/2011 |
| WO | 2011126079 A1 | 10/2011 |
| WO | 2014/054656 A1 | 4/2014 |
| WO | 2015/108084 A1 | 7/2015 |
| WO | 2015/129917 A1 | 9/2015 |

OTHER PUBLICATIONS

Edana, Particle Size Distribution 420.2-02 Recommended Test Method: Superabsorbent material—Polyacrylate superabsorbent powders—Particle Size Distribution—Sieve Fractionation, 2002, pp. 285-289.

Edana, Moisture Content 430.2-02, Recommended Test Method: Superabsorbent materials—Polyacrylate superabsorbent powders—Moisture Content—Weight Loss Upon Heatings, 2002, pp. 291-295.

Edana, Residual Monomers 410.2-02, Recommended Test Method: Superabsorbent materials—Polyacrylate superabsorbent powders—Determination of the Amount of Residual Monomers, 2002, pp. 275-283.

Korean Notice of Preliminary Rejection dated Mar. 19, 2020, which issued in the corresponding Korean Patent Application No. 10-2018-7031027, including Eng. Translation.

Indonesian Office Action dated Apr. 2, 2020, which issued in the corresponding Indonesian Patent Application No. P00201808615, including Eng. Translation.

International Search Report dated Jun. 20, 2017, which issued in PCT Application No. PCT/JP2017/012751, including English translation.

Communication Pursuant to Article 94(3) EPC dated Jul. 24, 2020, which issued in the corresponding EP Patent Application No. 17 775 141.9.

Edana, pH 400.2-02, Recommended Test Method: Superabsorbent materials—Polyacrylate superabsorbent powders—Determination of pH, 2002, pp. 269-273.

Japanese Office Action dated Jan. 6, 2020, which issued in the corresponding Japanese Patent Application No. 2018-508102.

Korean Office Action dated Dec. 2, 2020, which issued in the corresponding Korean Patent Application No. 10-2018-7031027, including English translation.

Chinese Office Action dated Dec. 21, 2020, which issued in the corresponding Chineses Patent Application No. 201780032885.5, including English translation.

Japanese Final Office Action dated Oct. 2, 2020, which issued in the corresponding Japanese Patent Application No. 2018-508102.

European Communication Pursuant of Article 94(3) EPC dated Mar. 24, 2021, which issued in the European Patent Application No. 17 775 141.9.

Japanese Pre-Appeal Examination Report dated Apr. 6, 2021, which issued in the corresponding Japanese Patent Application No. 2018-508102.

European Communication Pursuant of Article 94(3) EPC dated Aug. 24, 2021, which issued in the European Patent Application No. 17 775 141.9.

Chinese Office Action dated Aug. 16, 2021, which issued in the corresponding Chinese Patent Application No. 201780032885.5.

* cited by examiner ized bed drying, infrared drying, microwave drying, drum dryer drying, azeotropic dehydration drying with a hydrophobic organic solvent, and high humidity drying with use of high-temperature vapor at preferably 120 to 250° C. and more preferably 150 to 200° C., and for preferably 5 to 120 minutes, more preferably 10 to 90 minutes, and still more preferably 15 to 60 minutes.
METHOD FOR MANUFACTURING WATER ABSORBING AGENT

TECHNICAL FIELD

The present invention relates to a method of manufacturing a water absorbent agent. More specifically, the present invention provides a method of manufacturing a water absorbent agent with a high fluid retention capacity that can reduce stickiness after absorbing a liquid upon use as a sanitation material. The present invention also relates to a component and application for improving the tactile sensation of a water absorbent agent. The present invention further relates to a water absorbent agent with both strong urine resistance and resistance to coloration over time, and a manufacturing method thereof.

BACKGROUND ART

It is known that the performance of a water absorbent agent is improved by adding a specific additive during the manufacturing process of the water absorbent agent.

Patent Literature 1 (Japanese Patent No. 5415256) discloses that an addition of a malic acid upon polymerization results in improvement in coloration over time.

CITATION LIST

Patent Literature

[PTL 1] Japanese Patent No. 5415256

SUMMARY OF INVENTION

Solution to Problem

The present invention provides a water absorbent agent, which has stickiness or discomfort of a soluble component of the water absorbent agent that has permeated through a non-woven fabric on the surface upon use as a sanitation material improved by adding an α-hydroxycarboxylic acid (salt) before a drying step during the manufacturing process of the water absorbent agent. Enhancement in absorption ratio of a water absorbent agent is generally achieved by reducing the number (density) of crosslinking points. It is understood that a reduction of crosslinking points increases the weight average molecular weight of a polymer component which is not bound to a polymer network (formed by crosslinking), resulting in worsening of tactile sensation (stickiness). It was found that the molecular weight of soluble components, which elute out when a water absorbent agent absorbs a liquid and swells, can be reduced by adding an α-hydroxycarboxylic acid (salt) prior to the drying step during the manufacturing process of the water absorbent agent. It was found as a result thereof that stickiness leading to discomfort upon actual use of paper diaper or the like can be reduced.

Furthermore, the inventors have found, as a result of diligent research, that a water absorbent agent with both strong urine resistance and resistance to coloration over time can be manufactured by polymerizing an aqueous monomer solution comprising an acrylic acid (salt) in the presence of an α-hydroxycarboxylic acid (salt) and performing at least one of the steps performed after polymerization in the presence of a chelating agent.

The present invention also provides the following items.
(Item 1)
A method of manufacturing a water absorbent agent with a centrifuge retention capacity (CRC) of 30 g/g or greater, comprising of subjecting an aqueous monomer solution comprising an acrylic acid (salt) to a polymerization step, a drying step, and a surface crosslinking step, wherein the method comprises a step of adding an α-hydroxycarboxylic acid (salt) before the drying step.
(Item 2)
The method of the preceding item, wherein the α-hydroxycarboxylic acid (salt) is added before, during, or after the polymerization step.
(Item 3)
The method of any one of the preceding items, wherein the α-hydroxycarboxylic acid (salt) is added before or during the polymerization step.
(Item 4)
The method of any one of the preceding items, further comprising a gel grinding step after the polymerization step and before the drying step.
(Item 5)
The method of any one of the preceding items, wherein the α-hydroxycarboxylic acid (salt) is added before or during the gel grinding step.
(Item 6)
The method of any one of the preceding items, wherein an amount of the α-hydroxycarboxylic acid (salt) to be added is 0.010 to 4.0 mol % with respect to the acrylic acid (salt).
(Item 7)
The method of any one of the preceding items, wherein the α-hydroxycarboxylic acid (salt) is one or more selected from the group consisting of a malic acid (salt) and a lactic acid (salt).
(Item 8)
The method of any one of the preceding items, wherein the α-hydroxycarboxylic acid (salt) is a malic acid (salt).
(Item 9)
The method of any one of the preceding items, wherein a centrifuge retention capacity (CRC) before crosslinking of the water absorbent agent is greater than 34 g/g.
(Item 10)
The method of any one of the preceding items, wherein an amount of a soluble component of the water absorbent agent is 10% by weight or greater and 30% by weight or less.
(Item 11)
The method of any one of the preceding items, wherein a molecular weight of a soluble component of the water absorbent agent is 200,000 Daltons or greater and 700,000 Daltons or less.
(Item 12)
The method of any one of the preceding items, further comprising a step of reusing fine powder generated after the manufacture of the water absorbent agent.
(Item 13)
The method of any one of the preceding items, wherein the drying step comprises a step of performing at least one drying procedure selected from the group consisting of heat drying, hot-air drying, vacuum drying, fluidized bed drying, infrared drying, microwave drying, drum dryer drying, azeotropic dehydration drying with a hydrophobic organic solvent, and high humidity drying with use of high-temperature vapor at preferably 120 to 250° C. and more preferably 150 to 200° C., and for preferably 5 to 120 minutes, more preferably 10 to 90 minutes, and still more preferably 15 to 60 minutes.

(Item 14)

The method of any one of the preceding items, wherein a peak temperature during a polymerization reaction of the aqueous monomer solution in the polymerization step is 85° C. or greater.

(Item 15)

The method of any one of the preceding items, further comprising a step of adding a chelating agent after the drying step.

(Item 16)

The method of any one of the preceding items, wherein the chelating agent is selected from the group consisting of iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyclohexane tetraacetic acid, bis(2-hydroxyethyl) glycine, diaminopropanol tetraacetic acid, ethylenediamine-2-propionic acid, glycol ether diamine tetraacetic acid, bis(2-hydroxybenzyl) ethylenediaminediacetic acid, 3-hydroxy-2,2-iminodisuccinic acid, iminodisuccinic acid, methylglycinediacetic acid, ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), polymethylenediamine tetra (methylenephosphonic acid), diethylenetriamine penta (methylenephosphonic acid), 1-hydroxyethylidene diphosphonic acid, ethylenediamine-N, N'-di(methylenephosphinic acid), ethylenediamine tetra(methylenephosphinic acid), nitriloacetic acid-di (methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), ethylenediamine tetra(methylenephosphonic acid) (EDTMP), polymethylenediamine tetra(methylenephosphonic acid), diethylenetriamine penta(methylenephosphonic acid), and 1-hydroxyethylidene diphosphonic acid, and salts thereof.

(Item 17)

The method of any one of the preceding items, wherein the chelating agent is diethylenetriaminepentaacetic acid or a salt thereof (DTPA) or ethylenediamine tetra(methylenephosphonic acid) or a salt thereof (EDTMP).

(Item 18)

The method of any one of the preceding items, further comprising a step of adding at least one selected from the group consisting of silicon dioxide, phosphate, and hydrotalcite as a moisture absorption fluidity improving agent after the drying step.

(Item 19)

The method of any one of the preceding items, wherein the water absorbent agent has reduced stickiness after absorbing a liquid.

(Item 20)

The method of any one of the preceding items, wherein a molecular weight of a soluble component of the water absorbent agent is reduced 8% or more.

(Item 21)

A surface-crosslinked polyacrylic acid (salt)-based water absorbent agent comprising an α-hydroxycarboxylic acid (salt) therein, wherein a centrifuge retention capacity (CRC) is 30 g/g or greater, (Item 22)

The water absorbent agent of the preceding item, wherein a molecular weight of a soluble component of the water absorbent agent is 200,000 Daltons or greater and 700,000 Daltons or less.

(Item 23)

The water absorbent agent of any one of the preceding items, wherein an amount of the α-hydroxycarboxylic acid (salt) is 0.010 to 4.0 mol % to a raw material acrylic acid (salt).

(Item 24)

The water absorbent agent of any one of the preceding items, wherein the α-hydroxycarboxylic acid (salt) is one or more selected from the group consisting of a malic acid (salt) and a lactic acid (salt).

(Item 25)

The water absorbent agent of any one of the preceding items, wherein the α-hydroxycarboxylic acid (salt) is a malic acid (salt).

(Item 26)

The water absorbent agent of any one of the preceding items, wherein a centrifuge retention capacity (CRC) before surface crosslinking of the water absorbent agent is greater than 34 g/g.

(Item 27)

The water absorbent agent of any one of the preceding items, wherein an amount of a soluble component of the water absorbent agent is 10% by weight or greater and 30% by weight or less.

(Item 28)

The water absorbent agent of any one of the preceding items, wherein the water absorbent agent has reduced stickiness after absorbing a liquid.

(Item 29)

The water absorbent agent of any one of the preceding items, wherein a molecular weight of a soluble component of the water absorbent agent is reduced 8% or more.

(Item 30)

A water absorbent agent obtained by the method of any one of the preceding items.

(Item 31)

An absorbent core comprising the water absorbent agent of any one of the preceding items.

(Item 32)

A sanitation article comprising the absorbent core of any one of the preceding items.

(Item 33)

A composition for reducing a molecular weight of a soluble component of a water absorbent agent, comprising an α-hydroxycarboxylic acid (salt).

(Item 34)

A composition for reducing stickiness of a water absorbent agent after absorbing a liquid, comprising an α-hydroxycarboxylic acid (salt).

(Item 35)

A composition for reducing a viscosity of a soluble component of a water absorbent agent upon swelling from absorbing a liquid, comprising an α-hydroxycarboxylic acid (salt).

(Item 36)

The composition of any one of the preceding items, wherein the water absorbent agent is a polyacrylic acid (salt)-based water absorbent agent.

(Item 37)
The composition of any one of the preceding items, wherein the α-hydroxycarboxylic acid (salt) is one or more selected from the group consisting of a malic acid (salt) and a lactic acid (salt).
(Item 38)
The composition of any one of the preceding items, wherein the α-hydroxycarboxylic acid (salt) is a malic acid (salt).
(Item 39)
Use of an α-hydroxycarboxylic acid (salt) for reducing a molecular weight of a soluble component of a water absorbent agent.
(Item 40)
Use of an α-hydroxycarboxylic acid (salt) for reducing stickiness of a water absorbent agent after absorbing a liquid.
(Item 41)
Use of an α-hydroxycarboxylic acid (salt) for reducing a viscosity of a soluble component of a water absorbent agent upon swelling from absorbing a liquid.
(Item 42)
The use of any one of the preceding items, wherein the water absorbent agent is a polyacrylic acid (salt)-based water absorbent agent.
(Item 43)
The use of any one of the preceding items, wherein the α-hydroxycarboxylic acid (salt) is one or more selected from the group consisting of a malic acid (salt) and a lactic acid (salt).
(Item 44)
The use of any one of the preceding items, wherein the α-hydroxycarboxylic acid (salt) is a malic acid (salt).
(Item 45)
A method of reducing a molecular weight of a soluble component of a water absorbent agent, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying.
(Item 46)
A method of reducing stickiness of a water absorbent agent after absorbing a liquid, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying.
(Item 47)
A method of reducing a viscosity of a soluble component of a water absorbent agent upon swelling after absorbing a liquid, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying.

(Item 48)
The method of any one of the preceding items, wherein the α-hydroxycarboxylic acid (salt) is one or more selected from the group consisting of a malic acid (salt) and a lactic acid (salt).
(Item 49)
The method of any one of the preceding items, wherein the α-hydroxycarboxylic acid (salt) is a malic acid (salt).
(Item A1)
A water absorbent agent comprised of a polyacrylic acid (salt) as main component, wherein a Fe/L-as degradable soluble component, extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, is 35% by weight or less, and a YI value after a coloration promotion test is 26 or less.
(Item A2)
The water absorbent agent of the preceding item, comprising an effective amount of a chelating agent and an α-hydroxycarboxylic acid (salt).
(Item A3)
The water absorbent agent of any of the preceding items, comprising the chelating agent at 0.001 to 1.0% by weight and comprising the α-hydroxycarboxylic acid (salt) at 0.02 to 1.5% by weight.
(Item A4)
The water absorbent agent of any of the preceding items, wherein the YI value after a coloration promotion test is 25 or less.
(Item A5)
The water absorbent agent of any of the preceding items, wherein a particle shape is an irregular pulverized shape.
(Item A6)
The water absorbent agent of any of the preceding items, wherein surface tension is 65 [mN/m] or greater.
(Item A7)
The water absorbent agent of any of the preceding items, wherein a centrifuge retention capacity (CRC) is 30 g/g or greater.
(Item A8)
The water absorbent agent of any of the preceding items, wherein a neutralization rate is uniform.
(Item A9)
The water absorbent agent of any of the preceding items, wherein the α-hydroxycarboxylic acid (salt) is selected from the group consisting of lactic acid, glycolic acid, malic acid, glyceric acid, tartaric acid, citric acid, isocitric acid, mevalonic acid, quinic acid, shikimic acid, β-hydroxypropionic acid, salicylic acid, creosotic acid, vanillic acid, syringic acid, resorcylic acid, pyrocatechuic acid, protocatechuic acid, gentisic acid, orsellinic acid, mandelic acid and gallic acid.
(Item A10)
The water absorbent agent of any of the preceding items, wherein the chelating agent is selected from the group consisting of iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyclohexane tetraacetic acid, bis(2-hydroxyethyl) glycine, diaminopropanol tetraacetic acid, ethylenediamine-2-propionic acid, glycol ether diamine tetraacetic acid, bis(2-hydroxybenzyl) ethylenediaminediacetic acid, 3-hydroxy-2,2-iminodisuccinic acid, iminodisuccinic acid, methylglycinediacetic acid, ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), polymethylenediamine tetra (methylenephosphonic acid), diethylenetriamine penta (methylenephosphonic acid), and 1-hydroxyethylidene diphosphonic acid.

(Item A11)

An absorbent core comprising the water absorbent agent of any one of the preceding items.

(Item A12)

A sanitation article comprising the absorbent core of the preceding item.

(Item A13)

A method of manufacturing a polyacrylic acid (salt)-based water absorbent agent, comprising a step of polymerizing an aqueous monomer solution having an acrylic acid (salt) as a main component in the presence of an α-hydroxycarboxylic acid (salt), wherein a chelating agent is added in at least one of the post-polymerization steps.

(Item A14)

The method of the preceding item, wherein the post-polymerization step is selected from the group consisting of a drying step, a surface treating (crosslinking) agent mixing step, a surface crosslinking (surface treating) step, a granulating step, and a curing step.

(Item A15)

The method of any of the preceding items, wherein the step of polymerizing is performed in the presence of the chelating agent.

(Item A16)

The method of any of the preceding items, wherein a ratio of a chelating agent that is present in the step of polymerizing and a chelating agent added in the post-polymerization step is 1:1 to 1:20.

(Item A17)

The method of any of the preceding items, wherein an amount of the chelating agent added in the post-polymerization step is 0.005 to 0.2 parts by weight relative to 100 parts by weight of water absorbent agent.

(Item A18)

The method of any of the preceding items, wherein content of an α-hydroxycarboxylic acid (salt) that is present in the step of polymerizing is 0.02 to 1.5 parts by weight relative to 100 parts by weight of acrylic acid (salt).

(Item A19)

The method of any of the preceding items, wherein the α-hydroxycarboxylic acid (salt) is selected from the group consisting of lactic acid, glycolic acid, malic acid, glyceric acid, tartaric acid, citric acid, isocitric acid, mevalonic acid, quinic acid, shikimic acid, g-hydroxypropionic acid, salicylic acid, creosotic acid, vanillic acid, syringic acid, resorcylic acid, pyrocatechuic acid, protocatechuic acid, gentisic acid, orsellinic acid, mandelic acid and gallic acid.

(Item A20)

The method of any of the preceding items, wherein the chelating agent is selected from the group consisting of iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyolohexane tetraacetic acid, bis(2-hydroxyethyl) glycine, diaminopropanol tetraacetic acid, ethylenediamine-2-propionic acid, glycol ether diamine tetraaoetic acid, bis(2-hydroxybenzyl) ethylenediaminediacetic acid, 3-hydroxy-2,2-iminodisuccinic acid, iminodisuccinic acid, methylglycinediacetic acid, ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di (methylenephosphonic acid), polymethylenediamine tetra (methylenephosphonic acid), diethylenetriamine penta (methylenephosphonic acid), and 1-hydroxyethylidene diphosphonic acid.

(Item A21)

The method of any of the preceding items, wherein a moisture absorption fluidity improving agent is further added in at least one of the post-polymerization steps.

(Item A22)

The method of any of the preceding items, wherein the moisture absorption fluidity improving agent comprises at least one selected from the group consisting of silicon dioxide, phosphate, and hydrotaloite.

(Item A23)

A composition for improving strong urine resistance of a water absorbent agent, comprising an α-hydroxycarboxylic acid (salt) and a chelating agent.

(Item A24)

A composition for improving resistance to coloration over time of a water absorbent agent, comprising an α-hydroxycarboxylic acid (salt) and a chelating agent.

(Item A25)

A composition for improving strong urine resistance and resistance to coloration over time of a water absorbent agent, comprising an α-hydroxycarboxylic acid (salt) and a chelating agent.

(Item A26)

Use of an α-hydroxycarboxylic acid (salt) and a chelating agent for improving strong urine resistance of a water absorbent agent.

(Item A27)

Use of an α-hydroxycarboxylic acid (salt) and a chelating agent for improving resistance to coloration over time of a water absorbent agent.

(Item A28)

Use of an α-hydroxycarboxylic acid (salt) and a chelating agent for improving strong urine resistance and resistance to coloration over time of a water absorbent agent.

(Item A29)

A method for improving strong urine resistance of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component, extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less; and a YI value after a coloration promotion test of 26 or less.
(Item A30)

A method of improving resistance to coloration over time of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component, extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less; and a YI value after a coloration promotion test of 26 or less.
(Item A31)

A method of improving strong urine resistance and resistance to coloration over time of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component, extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less; and a YI value after a coloration promotion test of 26 or less.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

The present invention has developed a water absorbent agent with a high fluid retention capacity, capable of reducing stickiness after absorbing a liquid upon use as a sanitation material. Most preferably, the present invention has developed a water absorbent agent with unprecedented, excellent absorbing capabilities (excellent, strong urine resistance and resistance to coloration over time) upon use of the water absorbent agent in actual use in absorbent articles such as diapers.

DESCRIPTION OF EMBODIMENTS

Figure 1:
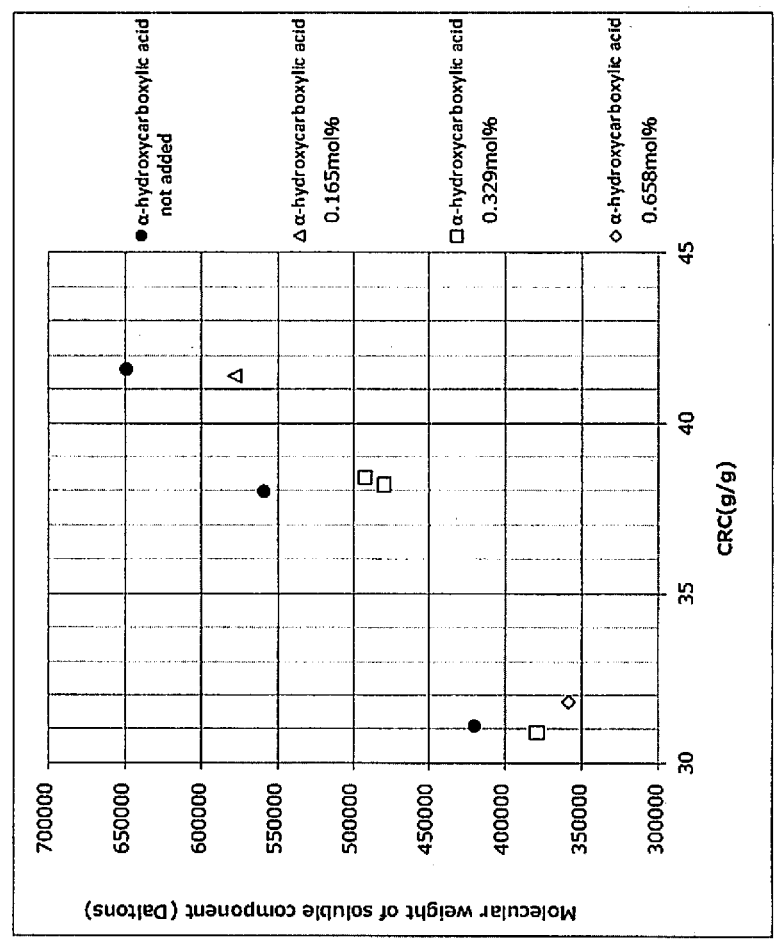
FIG. 1 is a graph plotting the relationship between centrifuge retention capacity (CRC) (g/g) and molecular weight of soluble component (Daltons) at various amounts of α-hydroxycarboxylic acid (salt) (0 mol %, 0.165 mol %, 0.329 mol %, and 0.658 mol % (Examples 3-5, Example 8, Examples 3, 4, and 7, and Example 1, respectively)) added to the water absorbent agents in the Examples and Comparative Examples of the present invention.

The present invention is explained hereinafter while presenting the best modes of the present invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

[1] Definitions of Terms (1-1) "Water Absorbent Resin"

"Water absorbent resin" in the present invention refers to a water-swellable, water-insoluble polymer gelling agent satisfying the following properties, i.e., a polymer gelling agent satisfying the following physical properties CRC as specified in ERT441.2-02 of 5 g/g or greater as "water swellable"; and Ext as specified in ERT470.2-02 of 50% by weight or less as "water-insoluble".

The water absorbent resin can be appropriately designed in accordance with the application thereof. The water absorbent resin is not particularly limited, but is preferably a hydrophilic crosslinked polymer in which an unsaturated monomer with a carboxyl group is crosslinked. The water absorbent resin is not limited to a form in which the entire amount (100% by weight) is a polymer. The water absorbent resin may be a water absorbent resin composition comprising an additive or the like, to the extent that the above physical properties (CRC and Ext) are satisfied.

Furthermore, the water absorbent resin in the present invention is not limited to final products, referring to, in some cases, intermediates in a manufacturing process of a water absorbent resin (e.g., crosslinked hydrogel polymers after polymerization, dried polymers after drying, water absorbent resin powder before surface crosslinking and the like). Together with the above water absorbent resin compositions, they are collectively called "water absorbent resin". Examples of shapes of a water absorbent resin include sheet, fiber, film, particle, and gel forms and the like, but a particulate water absorbent resin is preferred in the present invention.

(1-2) "Polyacrylic Acid (Salt)"

"Polyarcylic acid (salt)" in the present invention refers to a polyacrylic acid and/or a salt thereof. Polyacrylic acid (salt) refers to a polymer comprising, as a main component, an acrylic acid and/or a salt thereof (hereinafter, referred to as "acrylic acid (salt)") as a repeating unit, and a graft component as an optional component.

The "main component" refers to the amount of acrylic acid (salt) used (content) of generally 50 to 100 mol %, preferably 70 to 100 mol %, and more preferably 90 to 100 mol %, and still more preferably substantially 100 mol % relative to the whole monomer used in polymerization (excluding the internal crosslinking agent).

(1-3) "Water Absorbent Agent"

As used herein, a water absorbent agent refers to an absorbing gelating agent of an aqueous liquid, comprising a water absorbent resin as a main component. "Water absorbent agent" is also referred to as a "particulate water absorbent agent".

An aqueous liquid is not limited to water. An aqueous liquid may be urine, blood, sweat, feces, waste fluid, moisture, steam, ice, a mixture of water and an organic solvent and/or inorganic solvent, rain water, ground water or the like. It is not limited to specific liquids, as long as water is included. Preferred examples thereof include urine, menstrual blood, sweat, and other bodily fluids.

The water absorbent agent in the present invention is optimally used as a sanitation material for absorbing aqueous liquids. A water absorbent resin, as a polymer, is contained as a main component in a water absorbent agent. In other words, a water absorbent resin is preferably contained in a particulate water absorbent agent at 60 to 100% by mass, 70 to 100% by mass, 80 to 100% by mass, or 90 to 100% by mass. In addition, an additive, such as water and/or inorganic microparticles or multivalent metal cation, is optionally included as a non-polymer. Optimal water content is 0.2 to 30% by mass. In other words, water absorbent resin compositions integrated with such components are within the scope of the water absorbent agent.

The upper limit of a water absorbent resin in a water absorbent agent is about 99% by mass, 97% by mass, or particularly 95% by mass, and preferably further comprises water or an additive discussed below (inorganic microparticles or multivalent metal cation).

Examples of water absorbent resins used as a main component of a water absorbent agent include polyacrylic acid (salt)-based resin, polysulfonic acid (salt)-based resin, anhydrous maleic acid (salt)-based resin, polyacrylamide-based resin, polyvinylalcohol-based resin, polyethyleneoxide-based resin, polyaspartic acid (salt)-based resin, polyglutamic acid (salt)-based resin, polyalginic acid (salt)-based resin, starch-based resin, and cellulose-based resin. Preferably, polyacrylic acid (salt)-based resin is used.

(1-4) "EDANA" and "ERT"

"EDANA" is an acronym for European Disposables and Nonwovens Associations, and "ERT" is an acronym for a European standard (nearly a global standard) measurement method of water absorbent resins (EDANA Recommended Test Methods). In the present invention, physical properties of water absorbent resin are measured in accordance with the original copy of ERT (revised in 2002/known document) unless specifically noted otherwise.

(1-4-1) "CRC" (ERT441.2-02)

"CRC" is an acronym for Centrifuge Retention Capacity, referring to fluid retention capacity without pressure of a water absorbent resin (may also be called a "fluid retention capacity").

Specifically, CRC refers to the fluid retention capacity (unit; g/g) after placing 0.2 g of water absorbent resin in a non-woven fabric bag and then immersing the water absorbent resin in an overexcessive amount of aqueous 0.9% by weight sodium chloride solution for 30 minutes to allow the resin to freely swell, and then draining the resin with a centrifuge (250 G).

(1-4-2) "AAP" (ERT442.2-02)

"AAP" is an acronym for Absorption Against Pressure, referring to a fluid retention capacity of water absorbent resin under pressure.

Specifically, "AAP" means fluid retention capacity (unit; g/g) obtained after 0.9 g of a water absorbent resin is swollen in 0.9 wt % of aqueous sodium chloride solution in a largely excessive amount under a load of 2.1 kPa (21 g/cm$^2$, 0.3 psi) for 1 hour. In some measurements, the pressure condition is changed to 4.83 kPa (49 g/cm$^2$, 0.7 psi)

ERT442.2-02 also recites "Absorption Under Pressure", which substantially means the same.

(1-4-3)

"PSD" (ERT420.2-02)

"PSD" is an acronym of Particle Size Distribution, referring to the particle size distribution of water absorbent resin, which is measured by sieve classification.

The weight average particle diameter (D50) and logarithmic standard deviation (at) of particle size distribution are measured by the same method as "(3) Mass-Average Particle Diameter (D50) and Logarithmic Standard Deviation ($\sigma\zeta$) of Particle Diameter Distribution" described in U.S. Pat. No. 7,638,570.

(1-4-4) "Ext" (ERT470.2-02)

"Ext" is an abbreviation for Extractables, referring to a water-soluble component (amount of water-soluble component) of water soluble resin.

The "water-soluble component" is also simply referred to as "soluble component". When the amount of water-soluble component is indicated, the "amount of water-soluble component" is also referred to as "amount of soluble component" or simply as "soluble component", and may be referred to as "soluble component ratio" discussed below.

Specifically. "Ext" is the amount of dissolved polymer (unit; weight %) after 1.0 g of a water absorbent resin is added to 200 ml of 0.9 weight % of aqueous sodium chloride solution, and the resulting mixture is stirred for 16 hours at 500 rpm. The amount of dissolved polymer is measured by pH titration.

(1-4-5) "Moisture Content" (ERT430.2-02)

"Moisture Content" refers to the water content of water absorbent resin.

Specifically, moisture content refers to a value calculated from the amount of decrease from drying when 4.0 g of water absorbent resin is dried for 3 hours at 105° C. The value is in some cases measured by changing the water absorbent resin to 1.0 g and drying temperature to 180° C.

(1-4-6) "Residual Monomers" (ERT410.2-02)

"Residual Monomers" refers to the amount of monomer remaining in water absorbent resin.

Specifically, residual monomer refers to the amount of dissolved residual monomer (unit; ppm) after adding 1.0 g of water absorbent resin to 200 ml of aqueous 0.9% by weight sodium chloride solution, and stirring the solution for 1 hour at 500 rpm. The amount of dissolved residual monomer is measured using high performance liquid chromatography (HPLC).

(1-4-7) Other Physical Properties of Water Absorbent Resin Specified by EDANA

"pH" (ERT400.2-02) refers to the pH of water absorbent resin.

(1-5) "Liquid Permeability"

As used herein, "liquid permeability" of water absorbent resin refers to flowability of a liquid passing through between particles of swellable gel under load or no load. Representative measurement methods include SFC (Physiological saline Flow Conductivity) and GBP (Gel Bed Permeability).

"SFC" refers to liquid permeability of aqueous 0.69% by weight sodium chloride solution against water absorbent resin under a 2.07 kPa load. SFC is measured in accordance with the SFC testing method disclosed in U.S. Pat. No. 5,669,894.

"GBP" refers to liquid permeability of aqueous 0.9% by weight sodium chloride solution against water absorbent resin under load or free swelling. GBP is measured in accordance with the GBP testing method disclosed in International Publication No. WO 2005/016393.

(1-6) "Water Absorption Rate"

As used herein, the "water absorption rate" of water absorbent resin refers to a water absorption rate measured by "FSR" or "Vortex" (unit: seconds). "FSR" is an acronym for Free Swell Rate. Specific measurement methods are explained in the Examples disclosed below.

(1-7) Others

As used herein, "X to Y" indicating a range refers to "X or greater and Y or less". Unless specifically noted otherwise, the unit of weight "t (ton)" refers to "metric ton", and "ppm" refers to "weight ppm" or "mass ppm". Furthermore, each of "weight" and "mass", "parts by weight" and "parts by mass", and "% by weight" and "% by mass" is considered a synonym. Further, " . . . acid (salt)" refers to " . . . acid and/or salt thereof", and "(meth)acryl" refers to "acryl and/or methacryl".

Further, "liter" may be denoted as "l" or "L", and "% by weight" as "wt %" where convenient. Furthermore, detection limit or lower, upon measurement of a trace amount of a component, is denoted as N. D (Not Detected).

[2] Method of Manufacturing Polyacrylic Acid (Salt)-Based Water Absorbent Resin

The steps (2-1) to (2-10) of manufacturing the water absorbent resin of the present invention are shown hereinafter.

(2-1) Step of Preparing an Aqueous Monomer Solution

This step prepares an aqueous solution comprising an acrylic acid (salt) as a main component (hereinafter, referred to as "aqueous monomer solution"). A slurry of a monomer can also be used to the extent the water absorbing performance of the resulting water absorbent resin does not decrease, but this section explains an aqueous monomer solution for convenience.

The "main component" refers to the amount of acrylic acid (salt) used (content) of generally 50 mol % or greater, preferably 70 mol % or greater, and more preferably 90 mol % or greater (upper limit is 100 mol %) relative to the whole monomer subjected to a polymerization reaction of water absorbent resin (excluding the internal crosslinking agent).

(Acrylic Acid)

In the present invention, an acrylic acid and/or a salt thereof (hereinafter, referred to as "acrylic acid (salt)" is used as a monomer from the viewpoint of physical property and productivity of the resulting water absorbent resin.

The "acrylic acid" may be a known acrylic acid, preferably comprising methoxyphenols and more preferably p-methoxyphenol as a polymerization inhibitor at preferably 200 ppm or less, more preferably 10 to 160 ppm, and still more preferably 20 to 100 ppm from the viewpoint of polymerizability of the acrylic acid or hue of water absorbent resin. The compound described in US Patent Application No. 2008/0161512 is also applied for impurities in acrylic acids, Further, the "acrylic acid salt" is the above acrylic acid that has been neutralized with the basic composition disclosed below. Such acrylic acid salts may be an acrylic acid salt that is commercially available (e.g., sodium acrylate) or is neutralized and obtained at a water absorbent resin manufacturing plant.

(Basic Composition)

As used herein, "basic composition" refers to a composition comprising a basic compound. For example, commercially available aqueous sodium hydroxide solutions and the like fall under a basic composition.

Specific examples of the basic compounds include carbonates salts and bicarbonates salts of alkali metals, hydroxides of alkali metals, ammonia, organic amines, and the like. Such basic compounds that are strongly basic are desirable from the viewpoint of physical properties of the resulting water absorbent resin. Specifically, hydroxides of alkali metals such as sodium hydroxide, potassium hydroxide, and lithium hydroxide are preferable, and sodium hydroxide is more preferable.

(Neutralization)

As neutralization in the present invention, either neutralization of an acrylic acid (before polymerization) or neutralization of crosslinked hydrogel polymer obtained by crosslink polymerization of an acrylic acid (after polymerization) (hereinafter, referred to as "subsequent neutralization") may be selected or both may be used concurrently. Such neutralization is not particularly limited. Neutralization may be performed continuously or in batches, but the continuous form is preferred from the viewpoint of efficiency of production or the like.

The conditions described in International Publication No. WO 2009/123197 or US Patent Application Publication No. 2008/0194863 are also applicable to the present invention as conditions, such as a neutralization apparatus, neutralization temperature, and residence time.

The neutralization rate in the present invention is preferably 10 to 90 mol %, more preferably 40 to 85 mol %, still more preferably 50 to 80 mol %, and particularly preferably 60 to 75 mol %, relative to an acid group of a monomer. When the neutralization rate is less than 10 mol %, the fluid retention capacity may decrease significantly. On the other hand, when the neutralization rate exceeds 90 mol %, water absorbent resin with a high fluid retention capacity under pressure may not be obtained.

The neutralization rate is the same in subsequent neutralization. The above neutralization rate is also applicable for the neutralization rate of water absorbent resin as a final product. A neutralization rate of 75 mol % refers to a mixture of 25 mol % of acrylic acid and 75 mol % of acrylic acid salt. Such a mixture may also be called a partially neutralized acrylic acid.

(Other Monomer)

As used herein, "other monomer" refers to a monomer other than the acrylic acid (salt). Water absorbent resin can be manufactured by combined use of an acrylic acid (salt) therewith.

Examples of the other monomer include water-soluble or hydrophobic unsaturated monomers. Specifically, the compounds described in US Patent Application No. 2005/0215734 (excluding acrylic acids) are also applicable to the present invention.

(Internal Crosslinking Agent)

As an internal crosslinking agent used in the present invention, the compounds described in U.S. Pat. No. 6,241,928 are also applicable to the present invention. One or two or more compounds are selected thereamong while taking into consideration the reactivity.

Examples of internal crosslinking agents used in the present invention include one or more N,N'-methylenebisacrylamide, (poly)ethylene glycol di(meth)acrylate, (poly)propylene glycol di(meth)acrylate, (polyoxyethylene)trimethylol propane tri(meth)acrylate, trimethylolpropane di(meth)acrylate, polyethylene glycol di(β-acryloyloxy propionate), trimethylolpropane tri(β-acryloyloxy propionate), poly(meth)allyloxy alkane and other compounds with at least two polymerizable double bonds in a molecule, polyglycidyl ether (such as ethylene glycol diglycidyl ether and the like), polyol (such as ethylene glycol, polyethylene glycol, glycerol and sorbitol and the like), and other compounds that can form a covalent bond by reacting with a carboxyl group.

From the viewpoint of water absorbing performance or the like of the resulting water absorbent resin, a compound with two or more polymerizable unsaturated groups is preferred, a compound with a pyrolytic property at the following drying temperature is more preferred, and a compound with two or more polymerizable unsaturated groups with a (poly)alkylene glycol structural unit is still more preferred for use as an internal crosslinking agent.

The polymerizable unsaturated group is preferably an allyl group or a (meth)acrylate group, and more preferably a (meth)acrylate group. The (poly)alkylene glycol structural unit is preferably polyethylene glycol, and n is preferably 1 to 100 and more preferably 6 to 50.

Thus, the present invention preferably uses (poly)alkylene glycol di(meth)acrylate or (poly)alkylene glycol tri(meth)acrylate, and more preferably (poly)ethylene glycol di(meth)acrylate.

The amount of the internal crosslinking agent to be used is preferably 0.0001 to 10 mol % and more preferably 0.001 to 1 mol % relative to the whole monomer. The amount within the above range results in a desired water absorbent resin. If the amount is too low, gel strength tends to decrease and water-soluble component increases. If the amount is too high, the fluid retention capacity tends to decrease, which is not preferred. The amount of the internal crosslinking agent to be used can be appropriately adjusted to appropriately adjust the centrifuge retention capacity, the amount of soluble component, or the molecular weight of the soluble component of the resulting water absorbent agent.

In the present invention, a method of adding a predetermined amount of internal crosslinking agent in advance to an aqueous monomer solution to have a crosslinking reaction simultaneously with polymerization is preferably applied. Meanwhile, a method of post-crosslinking by adding an internal crosslinking agent during or after polymerization, a method of radical crosslinking using a radical polymerization initiator, a method of radiation crosslinking using active energy beams such as electron beams, UV rays or the like, etc. can also be used in addition to above method. These methods can also be used in combination.

(Other Substances that are Added to an Aqueous Monomer Solution)

The following substances can also be added upon preparation of an aqueous monomer solution from the viewpoint of improving the physical properties of resulting water absorbent resin.

Specifically, a hydrophilic polymer such as starch, starch derivative, cellulose, cellulose derivative, polyvinyl alcohol, polyacrylic acid (salt), or crosslinked polyacrylic acid (salt) can be added at preferably 50% by weight or less, more preferably at 20% by weight or less, still more preferably at 10% by weight or less, and particularly preferably 5% by weight or less (lower limit is 0% by weight), or a chain transfer agent, chelating agent, surfactant, a foaming agent for gas bubbles or the like, azo compound, or carbonate can be added at preferably 5% by weight or less, more preferably at 1% by weight or less, and still more preferably at 0.5% by weight or less (lower limit is 0% by weight).

Further, the above substance can be added to an aqueous monomer solution, added during polymerization, or both.

When water-soluble resin or water absorbent resin is used as the hydrophilic polymer, a graft polymer or a water absorbent resin composition (e.g., starch-acrylic acid polymer, PVA-acrylic acid polymer or the like) is obtained. Such polymers and water absorbent resin compositions are also within the scope of the present invention.

(Concentration of Monomer Component)

In this step, each of the above substances is added when preparing an aqueous monomer solution. The concentration of a monomer component in the aqueous monomer solution is not particularly limited, but is preferably 10 to 80% by weight, more preferably 20 to 75% by weight, and still more preferably 30 to 70% by weight from the viewpoint of physical properties of water absorbent resin. The concentration of the monomer component can be appropriately adjusted to appropriately adjust the centrifuge retention capacity, the amount of soluble component, or the molecular weight of the soluble component of the resulting water absorbent agent.

When an aqueous solution polymerization or reverse phase suspension polymerization is employed, a solvent other than water can be used concurrently as needed. In such a case, the type of solvent is not particularly limited.

The "concentration of a monomer component" (also denoted as "monomer concentration") is a value found from the following formula (1). The weight of the aqueous monomer solution does not include the weight of a graft component, water absorbent resin, or hydrophobic solvent in reverse phase suspension polymerization.

(Concentration of monomer component (% by weight))=(weight of monomer component)/(weight of aqueous monomer solution)×100    Formula (1)

(2-2) Polymerization Step

This is a step for polymerizing the acrylic acid (salt) based aqueous monomer solution obtained in the above preparation step of an aqueous monomer solution to obtain a crosslinked hydrogel polymer (hereinafter, referred to as "hydrogel").

(Polymerization Initiator)

The polymerization initiators used in the present invention are not particularly limited, as they are appropriately selected depending on a particular embodiment of polymerization or the like. Examples thereof include pyrolytic polymerization initiators, photolytic polymerization initiators, and redox-based polymerization initiators, which are used concurrently with a reducing agent for promoting degradation of such polymerization initiators. Specifically, one or two or more polymerization initiators disclosed in U.S. Pat. No. 7,265,190 are used. From the viewpoint of ease of handling of a polymerization initiator or physical properties of water absorbent resin, preferably a peroxide or azo compound, more preferably a peroxide, and still more preferably a persulfate is used.

Examples of pyrolytic polymerization initiators include persulfates: sodium persulfate, potassium persulfate, and ammonium persulfate; peroxides: hydrogen peroxide, t-butyl peroxide, and methyl ethyl ketone peroxide; azo compounds: azonitrile compounds, azoamidine compounds, cyclic azoamidine compounds, azoamide compounds, alkylazo compounds, 2,2'-azobis(2-amidinopropane) dihydrochloride, 2,2'-azobis[2-(2-imidazolin-2-yl) propane] dihydrochloride, and the like.

Examples of photolytic polymerization initiators include benzoyl derivatives, benzyl derivatives, acetophenone derivatives, benzophenone derivatives, azo compounds, and the like.

Examples of redox-based polymerization initiators include a system concurrently using and combining a reductive compound such as L-ascorbic acid or sodium hydrogen sulfite with the persulfate or peroxide. In the present invention, combined use of a photolytic polymerization initiator and a pyrolytic polymerization initiator is a preferred embodiment.

The amount of the polymerization initiator used with respect to a monomer is preferably 0.001 to 1 mol %, and more preferably 0.001 to 0.5 mol %. Further, the amount of the reducing agent used with respect to a monomer is preferably 0.0001 to 0.02 mol %.

Instead of the above polymerization initiators, an activation energy ray such as radiation, electron beam, or UV ray may be irradiated for a polymerization reaction, or such activation energy rays may be used in combination with a polymerization initiator.

(Polymerization Form)

The polymerization forms applied in the present invention are not particularly limited, but are preferably spray and droplet polymerization, aqueous solution polymerization, or reverse phase suspension polymerization, more preferably aqueous solution polymerization or reverse phase suspension polymerization, and still more preferably aqueous solution polymerization, from the viewpoint of water absorbing properties, ease of controlling polymerization, or the like. Among them, continuous aqueous solution polymerization is particularly preferable, which can be applied with either continuous belt polymerization or continuous kneader polymerization.

Specific forms of polymerization are disclosed, i.e., continuous belt polymerization is disclosed in U.S. Pat. Nos. 4,893,999 and 6,241,928, US Patent Application Publication No. 2005/215734, and the like, and continuous kneader polymerization is disclosed in U.S. Pat. Nos. 6,987,151, 6,710,141, and the like. The efficiency of producing water absorbent resin is improved by employing such continuous aqueous solution polymerization.

Preferred forms of the continuous aqueous solution polymerization include "high starting temperature polymerization" and "high concentration polymerization". "High starting temperature polymerization" refers to a form that starts polymerization at an aqueous monomer solution temperature of preferably 30° C. or greater, more preferably 35° C. or greater, still more preferably 40° C. or greater, and particularly preferably 50° C. or greater (upper limit is the boiling point). "High concentration polymerization" refers to a form of polymerization with a monomer concentration of preferably 30% by weight or greater, more preferably 35% by weight or greater, still more preferably 40% by weight or greater, and particularly preferably 45% by weight or greater (upper limit is the saturation concentration). These polymerization forms can be used in combination.

Polymerization can be performed under air atmosphere in the present invention, but polymerization is preferably performed under an inert gas atmosphere such as nitrogen or argon, from the viewpoint of the hue of the resulting water absorbent resin. In such a case, the oxygen concentration is preferably controlled to be, for example, 1% by volume or less. Dissolved oxygen in an aqueous monomer solution is preferably replaced with insert gas (e.g., dissolved oxygen; less than 1 mg/l).

In the present invention, polymerization can be bubble polymerization, which performs polymerization by dispersing gas bubbles (especially the above inert gas or the like) in an aqueous monomer solution.

Further, the concentration of solid components may be increased during polymerization in the present invention. The degree of increase in the solid components is defined by the following formula (2) as an indicator of such an increase in the concentration of solid components. The degree of increase in the concentration of solid components is preferably 1% by weight or greater, and more preferably 2% by weight or greater.

(Degree of increase in solid components (% by weight))=(concentration of solid components in hydrogel after polymerization (% by weight))−(concentration of solid components of aqueous monomer solution (% by weight))　　Formula (2):

However, the concentration of solid components of an aqueous monomer solution is a value that is found from the following formula (3), where components in a polymerization system are an aqueous monomer solution and graft component, water absorbent resin, and other solids (e.g., water insoluble microparticles or the like), which do not include a hydrophobic solvent in reverse phase suspension polymerization.

(Solid components in aqueous monomer solution (% by weight))=(weight of (monomer component+graft component+water absorbent resin+other solids))/(weight of components in polymerization system)×100　　Formula (3):

(α-Hydroxycarboxylic Acid (Salt))

It is generally preferable to add α-hydroxycarboxylic acid from the viewpoint of water absorbing properties, the hue of the resulting water absorbent agent (prevention of coloration) or the like. The present invention surprisingly found that addition of α-hydroxycarboxylic acid reduces the molecular weight of a soluble component of the resulting water absorbent agent, and therefore reduces stickiness and discomfort upon use as a sanitation material. From such additional viewpoints, addition of α-hydroxycarboxylic acid is more preferable.

Especially as an example of the manufacturing method of a water absorbent agent comprising an α-hydroxycarboxylic acid therein of the present invention, a method of mixing when the α-hydroxycarboxylic acid (salt) is mixed with an aqueous monomer solution is not particularly limited. For example, an α-hydroxycarboxylic acid (salt) or an aqueous α-hydroxycarboxylic acid (salt) solution is mixed with a monomer or an aqueous monomer solution to adjust an aqueous monomer solution comprising an α-hydroxycarboxylic acid (salt).

Furthermore, various physical properties of a water absorbent agent can be improved upon polymerization by adding to a monomer a water-soluble resin or water absorbent resin at for example 0 to 50% by weight or preferably at 0 to 20% by mass. Various physical properties of a water absorbent agent can also be improved by adding various foaming agents (carbonate, azo compound, gas bubbles and the like), surfactant, chelating agent, chain transfer agent such as hypophosphoric acid (salt) or the like at for example 0 to 5% by mass, and preferably at 0 to 1% by mass.

When an α-hydroxycarboxylic acid (salt) to be used is mixed with a monomer or hydrogel, a liquid, slurry, or solid (or powder) α-hydroxycarboxylic acid (salt) may be mixed directly or by using a solvent. The concentration and solvent upon mixing is not particularly limited, but generally 10 to 100% by mass, preferably 20 to 100% by mass, and more preferably 30 to 100% by mass aqueous solution is used.

When the α-hydroxycarboxylic acid used in the present invention is an α-hydroxymonocarboxylic acid such as a lactic acid, it is preferably 0.010 to 4.0 mol %, more preferably 0.025 to 2.5 mol % or 0.05 to 1.0 mol %, and most preferably 0.1 to 1.0 mol % relative to the unsaturated monomer from the viewpoint of water absorbing property and reduction of the molecular weight of a soluble component. Furthermore, when an α-hydroxypolybasic carboxylic acid such as malic acid, which is preferably used in the present invention, is used, the amount used is preferably 0.010 to 4.0 mol %, more preferably 0.025 to 2.5 mol % or 0.05 to 1.0 mol %, and most preferably 0.1 to 1.0 mol % relative to the unsaturated monomer from the viewpoint of water absorbing property and reduction of the molecular weight of a soluble component. The amount of α-hydroxycarboxylic acid (salt) used in the polymerization step can be appropriately adjusted to appropriately adjust the centrifuge retention capacity or the molecular weight of the soluble component of the resulting water absorbent agent.

"α-hydroxycarboxylic acid (salt)" refers to an α-hydroxycarboxylic acid and/or a salt thereof, which is a hydroxycarboxylic acid and/or a salt thereof with a hydroxyl group at position α in a molecule. Similarly, " . . . acid (salt)" refers to . . . acid and/or a salt thereof. Specifically, malic acid (salt) refers to a malic acid and/or a salt thereof, and lactic acid (salt) refers to a lactic acid and/or a salt thereof.

As the α-hydroxycarboxylic acid (salt), the compound and the amount used disclosed in International Publication No. WO 2011-040530 "[6] α-hydroxycarboxylic acid compound" are specifically applicable to the present invention.

A hydroxycarboxylic acid is a carboxylic acid also comprising a hydroxyl group in a molecule, including acids or salt thereof such as aliphatic hydroxy acids such as lactic acid, glycolic acid, malic acid, glyceric acid, tartaric acid, citric acid, isocitric acid, mevalonic acid, quinic acid, shikimic acid, and β-hydroxypropionic acid, aromatic hydroxy acids such as salicylic acid, creosotic acid, vanillic acid, syringic acid, resorcylic acid, pyrocatechuic acid, protocatechuic acid, gentisic acid, orsellinic acid, mandelic acid, gallic acid, and salts thereof.

Among the above compounds, α-hydroxycarboxylic acid used in the present invention refers to a carboxylic acid in which a hydroxyl group is bound to carbon at position α in a molecule, which is preferably an aliphatic hydroxycarboxylic acid such as a non-polymer α-hydroxycarboxylic acid and more preferably an aliphatic α-hydroxycarboxylic acid without a cyclic structure or an unsaturated group. An aromatic α-hydroxycarboxylic acid and α-hydroxycarboxylic acid with a cyclic structure or an unsaturated group is not preferred, because an oxidation reaction results in coloration thereof. Further, the molecular weight is preferably in the range of 40 to 2000, more preferably 60 to 1000, and particularly preferably 100 to 500. The α-hydroxycarboxylic acid used in the present invention is water soluble, with the solubility to 100 g of deionized water at 20±5° C. preferably 1 g or greater, more preferably 5 g or greater, still more preferably 10 g or greater, and particularly preferably 20 g or greater. Examples of such an α-hydroxycarboxylic acid include lactic acid (salt), citric acid (salt), malic acid (salt), isocitric acid (salt), glyceric acid (salt), tartaric acid (salt), D, L, and meso forms thereof, and the like. Preferably, an α-hydroxycarboxylic acid is one or more selected from lactic acid (salt), glycolic acid (salt), malic acid (salt), glyceric acid (salt), tartaric acid (salt), citric acid (salt), isocitric acid (salt), mevalonic acid (salt), quinic acid (salt), shikimic acid (salt), β-hydroxypropionic acid (salt), salicylic acid (salt), creosotic acid (salt), vanillic acid (salt), syringic acid (salt), resorcylic acid (salt), pyrocatechuic acid (salt), protocatechuic acid (salt), gentisic acid (salt), orsellinic acid (salt), mandelic acid (salt), and gallic acid (salt). One or more of these acids (salts) may be used concurrently as the α-hydroxycarboxylic acid (salt). More preferably, a malic acid (salt) and lactic acid (salt) may be concurrently used as the α-hydroxycarboxylic acid (salt).

An α-hydroxycarboxylic acid that is particularly preferably used is a malic acid, lactic acid, or an α-hydroxy polybasic carboxylic acid with 2 or more, preferably 2 to 10, more preferably 2 to 6, and still more preferably 2 to 4 carboxyl groups in the molecule. As an α-hydroxycarboxylic acid, malic acid (salt), citric acid (salt), isocitric acid (salt), or tartaric acid (salt) is particularly preferably used from the viewpoint of improving water absorbing properties or coloration and reducing the molecular weight of a soluble component. A malic acid (salt) is most preferably used as an α-hydroxycarboxylic acid.

When an α-hydroxycarboxylic acid is a salt in the present invention, it is preferably a monovalent salt form the viewpoint of solubility to water. An alkali metal salt such as lithium, potassium, or sodium, ammonium salt, monovalent amine salt or the like is preferably used. When an α-hydroxy polybasic carboxylic acid is used as a salt, all of the carboxyl groups may be a salt or only some may be a salt.

A method of adding an α-hydroxycarboxylic acid (salt) is discussed below in detail in the section of [6] Explanation of Preferred Embodiments (2-3) Post-Polymerization Step As used herein, "post-polymerization step" is a step performed after polymerization. The post-polymerization step is, but not limited to, at least one of gel grinding step, drying step, pulverizing step, classification step, surface treating (crosslinking) agent mixing step, surface crosslinking (surface treating) step, granulating step, curing step, and re-humidification step, and the like.

(2-4) Gel Grinding Step

This is a step for gel grinding hydrogel obtained in the polymerization step with, for example, a kneader, a screw extruder such as a meat chopper, or a gel grinder such as a cutter mill to obtain hydrogel particle (hereinafter, referred to as "hydrogel particle"). When the polymerization step is kneader polymerization, the polymerization step and the gel grinding step are simultaneously performed. When hydrogel particle is directly obtained during the polymerization procedure as in vapor phase polymerization, reverse phase suspension polymerization or the like, the gel grinding step is not performed in some cases.

For gel grinding conditions or forms other than those disclosed above, the disclosed content in International Publication No. WO 2011/126079 is preferably applied to the present invention.

(2-5) Drying Step

This is a step of drying the particular hydrogel obtained in the polymerization step and/or gel grinding step until it is a desired resin solid component to obtain a dried polymer. The resin solid portion is found from the reduction in dry weight (change in weight after heating 1 g of water absorbent resin for 3 hours at 180° C.), which is preferably 80% by weight or greater, more preferably 85 to 99% by weight, still more preferably 90 to 98% by weight, and particularly preferably 92 to 97% by weight.

Examples of methods of drying the hydrogel particle include, but are not particularly limited to, heat drying, hot-air drying, vacuum drying, fluidized bed drying, infrared drying, microwave drying, drum dryer drying, azeotropic dehydration drying with a hydrophobic organic solvent, high humidity drying with use of high-temperature vapor, and the like. Among them, hot air drying is preferred, and band drying that performs hot air drying on a ventilation belt, hot air drying using an endless belt, or drum dryer drying is more preferred from the viewpoint of drying efficiency.

The drying temperature in the hot air drying (temperature of hot air) is preferably 120 to 250° C., and more preferably 150 to 200° C. from the viewpoint of the drying efficiency and hue of water absorbent resin. Drying conditions other than the above drying temperature, such as the wind speed of hot air or drying time, may be appropriately determined in accordance with the water content or total weight of the hydrogel particle subjected to drying or the resin solid component of interest. Various conditions disclosed in International Publication Nos. WO 2006/100300, 2011/025012, 2011/025013, 2011/111657 and the like can be appropriately applied for band drying.

The drying temperature and drying time in the above range enables CRC (centrifuge retention capacity) or Ext (water-soluble component) of the resulting water absorbent resin to have a hue within a desired range (see the following [3]).

(2-6) Pulverizing Step and Classification Step

This is a step for pulverizing the dried polymer obtained in the drying step (pulverizing step) and adjusting the particle size in a predetermined range (classification step) to obtain water absorbent resin powder (powdered water absorbent resin prior to surface crosslinking is called "water absorbent resin powder" for convenience's sake).

Examples of equipment used in the pulverizing step in the present invention include high speed rotation mills such as roll mills, hammer mills, screw mills, and pin mills, vibration mills, knuckle mills, cylindrical mixers and the like, which are used in combination as needed.

Examples of methods of adjusting particle size in the classification step in the present invention include, but are not particularly limited to, sieve classification or gas flow classification using a JIS standard sieve (JIS Z8801-1 (2000)) and the like. The adjustment of particle size of water absorbent resin is not limited to the above pulverizing step and classification step. The adjustment can be appropriately performed in the polymerization step (especially reverse phase suspension polymerization or spray and droplet polymerization) or in other steps (e.g., granulating step or fine powder collecting step).

The water absorbent resin powder obtained in the present invention is, in terms of weight average particle diameter (D50), preferably 200 to 600 μm, more preferably 200 to 550 μm, still more preferably 250 to 500 μm, and particularly more preferably 350 to 450 μm. Further, the ratio of particles with a particle size of less than 150 μm is preferably 10% by weight or less more preferably 5% by weight or less, and still more preferably 1% by weight of less, and the ratio of particles with a particle size of 850 μm or greater is preferably 5% by weight of less, more preferably 3% by weight of less, and still more preferably 1% by weight or less. The lower limit of the ratios of such particles is preferable the lower it is in each case. 0% by weight is desirable, but the ratio may be about 0.1% by weight. Furthermore, the logarithmic standard deviation ($\sigma\zeta$) of particle size distribution is preferably 0.20 to 0.50, more preferably 0.25 to 0.40, and still more preferably 0.27 to 0.35. These granularities are measured using a standard sieve in accordance with the measurement method disclosed in U.S. Pat. No. 7,638,570 or EDANA ERT420.2-02.

The aforementioned granularities are applied to not only water absorbent resin after surface crosslinking (hereinafter, referred to as "water absorbent resin particles" in some cases where convenient), but also to water absorbent resin as a final product. For this reason, water absorbent resin particles are preferably subjected to surface crosslinking treatment (surface crosslinking step) and more preferably particle size adjustment by providing a size aligning step after the surface crosslinking step to maintain the particle size in the above range.

(2-7) Surface Crosslinking (Surface Treating) Step

This is a step of further providing a portion with a high crosslink density on a surface layer (a portion that is several 10s of μm from the surface of water absorbent resin powder) of water absorbent resin powder that is obtained through the aforementioned steps. The step is comprised of a mixing step, heating step, and cooling step (optional).

Said surface crosslinking step results in a water absorbent resin (water absorbent resin particles) that is crosslinked on the surface by a crosslinking reaction with a surface crosslinking agent, surface polymerization, radical crosslinking, or the like at the surface of water absorbent resin powder.

(Surface Crosslinking Agent)

Examples of surface crosslinking agents that are used in the present invention include, but are not particularly limited to, organic or inorganic surface crosslinking agents. Among them, organic surface crosslinking agents that react with a carboxyl group are preferred from the viewpoint of physical properties of water absorbent resin or ease with which a surface crosslinking agent is handled. Examples thereof include one or two or more types of surface crosslinking agents disclosed in U.S. Pat. No. 7,183,456. More specific examples thereof include polyhydric alcohol compounds, epoxy compounds, halo epoxy compounds, condensates with a multivalent amine compound or a halo epoxy compound thereof, oxazoline compounds, oxazolidinone compounds, multivalent metal salts, alkylene carbonate compounds, cyclic urea compounds, and the like.

The amount of the surface crosslinking agent used (total amount used when multiple agents are used) is preferably 0.01 to 10 parts by weight, and more preferably 0.01 to 5 parts by weight, relative to 100 parts by weight of water absorbent resin powder. Further, the surface crosslinking agent is preferably added as an aqueous solution. In such a case, the amount of water used, with respect to 100 parts by weight of water absorbent resin powder, is preferably 0.1 to 20 parts by weight, and more preferably 0.5 to 10 parts by weight. Optionally, when a hydrophilic organic solvent is used, the amount thereof that is used is preferably 10 parts by weight or less and more preferably 5 parts by weight of less, relative to 100 parts by weight of water absorbent resin powder.

Further, each of the additives added in the "re-humidification step" discussed below can be mixed and added to the surface crosslinking agent (aqueous solution) within the range of 5 parts by weight or less, or added separately in the mixing step.

(Mixing Step)

This is a step for mixing water absorbent resin powder with the surface crosslinking agent. Examples of methods of mixing the surface crosslinking agent include, but are not particularly limited to, a method of preparing a surface crosslinking agent solution in advance and mixing the solution by preferably spraying or titrating, and more preferably by spraying, the solution onto water absorbent resin powder.

The apparatus performing the mixing is not particularly limited, but is preferably a high speed stir mixer, and more preferably a high speed stir continuous mixer.

(Heating Step)

This is a step for adding heat to a mixture discharged from the mixing step to induce a crosslinking reaction on the surface of water absorbent resin powder.

The apparatus performing the crosslinking reaction is not particularly limited, but is preferably a paddle dryer.

The reaction temperature in the crosslinking reaction is appropriately determined in accordance with the type of surface crosslinking agent to be used, but is preferably 50 to 300° C., and more preferably 100 to 200° C. The heating temperature in the surface crosslinking step can be appropriately adjusted to appropriately adjust the centrifuge retention capacity of the resulting water absorbent agent.

The heating time in the heating step is not particularly limited, but is appropriately determined in accordance with the type, reactivity, amount, and the like of a surface crosslinking agent to be used, preferably 15 to 120 minutes and more preferably 30 to 60 minutes. The heating time in the surface crosslinking step can be appropriately adjusted to appropriately adjust the centrifuge retention capacity of the resulting water absorbent agent.

(Cooling Step)

This is an optional step provided as needed after the heating step.

The apparatus performing said cooling is not particularly limited, but is preferably an apparatus with the same specification as the apparatus used in the heating step, and more preferably a paddle dryer. This is because a heating medium can be replaced with a cooling medium to use the apparatus as a cooling apparatus. The water absorbent resin particle obtained in the heating step is forced to be cooled as needed in the cooling step, preferably to 40 to 80° C. and more preferably to 50 to 70° C.

(2-8) Re-Humidification Step

This is a step for adding at least one type of additive selected from the group consisting of the following multivalent metal salt compounds, polycationic polymers, chelating agents, inorganic reducing agents, and hydroxycarboxylic acid compounds to the water absorbent resin particle obtained in the surface crosslinking step.

Since the additives are added as an aqueous solution or slurry, a water absorbent resin particle is swelled up again with water. For this reason, this step is called the "re-humidification step". As disclosed above, the additive can also be mixed with water absorbent resin powder, simultaneously with the surface crosslinking agent (aqueous solution).

(Multivalent Metal Salt and/or Cationic Polymer)

It is preferable in the present invention to add a multivalent metal salt and/or cationic polymer from the viewpoint of improvement in the water absorption rate, liquid permeability, moisture absorption fluidity or the like of the resulting water absorbent resin.

As the multivalent metal salt and/or cationic polymer, the specific compounds and the amount used disclosed in "[7] Multivalent metal salt and/or cationic polymer" in International Publication No. WO 2011/040530 are applicable to the present invention.

(Chelating Agent)

"Chelating agent" refers to a polydentate ligand forming a chelating compound by forming a coordinate bond with a metal ion.

The mode of adding a chelating agent is not particularly limited, but a mode of adding a solution of a liquid or powder chelating agent dissolved in a hydrophilic solvent such as water or a mode of adding a fine powder chelating agent as powder is preferred in order to homogeneously disperse the chelating agent in a water absorbent agent.

In the present invention, it is preferable to add a chelating agent from the viewpoint of the hue (prevention of coloration, resistance to coloration over time), prevention of degradation (strong urine resistance), or the like of the resulting water absorbent resin.

As the above chelating agent, the specific compound and amount used that are disclosed in "[2] Chelating agent" in International Publication No. WO 2011/040530 are applicable to the present invention.

More specific examples of the chelating agent include phosphorous-based chelating agents and aminocarboxylic acid-based chelating agents.

As a phosphorous-based chelating agent used in the present invention, organic amino phosphate with an amino group is preferable, and water soluble organic amino phosphate or water soluble non-polymer organic amino phosphate is used. The number of amino groups per one molecule thereof is preferably one or more or two or more, and the number of phosphoric acid groups is preferably one or more, two or more, and especially three of more. The upper limit on the number of amino groups or phosphoric acid groups is generally 100 or less, or 10 or less, or especially 5 or less. Water solubility in the present invention refers to a compound that dissolves at 0.1 g or more, or 1 g or more, and especially 5 g or more to 100 g of water at 25° C. Further, the range of molecular weight is generally 50 to 5000, preferably 100 to 1000, and 200 to 500.

Examples of phosphorous-based chelating agents that are used include ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), ethylenediamine tetra (methylenephosphonic acid), polymethylenediamine tetra (methylenephosphonic acid), diethylenetriamine penta (methylenephosphonic acid), 1-hydroxyethylidene diphosphonic acid, and salts thereof. The most preferred phosphorous-based chelating agent in the present invention is ethylenediamine tetra(methylenephosphonic acid) or a salt thereof. Examples of preferred salts include alkali metal salts such as sodium salt and potassium salt, ammonium salts, and amine salts. Sodium salt and potassium salt are particularly preferably as a salt.

Examples of aminocarboxylic acid-base chelating agent used include iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyclohexane tetraacetic acid, bis(2-hydroxyethyl) glycine, diaminopropanol tetraacetic acid, ethylenediamine-2-propionic acid, glycol ether diamine tetraacetic acid, bis(2-hydroxybenzyl) ethylenediaminediacetic acid, 3-hydroxy-2,2-iminodisuccinic acid, iminodisuccinic acid, methylglycinediacetic acid and salts thereof. The most preferred aminocarboxylic acid-based chelating agent in the present invention is diethylenetriaminepentaacetic acid (DTPA) or a salt thereof. Examples of preferred salts include alkali metal salts such as sodium salt and potassium salt, ammonium salts, and amine salts. Sodium salt and potassium salt are particularly preferably as a salt.

The most preferred phosphorous-based chelating agent used in the present invention is diethylenetriaminepentaacetic acid (DTPA) or a salt thereof, or ethylenediamine tetra(methylenephosphonic acid) (EDTMP) or a salt thereof.

(Inorganic Reducing Agent)

It is preferable to add an inorganic reducing agent in the present invention from the viewpoint of the hue (prevention of coloration), prevention of degradation, and reduction of residual monomer or the like of the resulting water absorbent resin.

As the inorganic reducing agent, the specific compounds and the amount thereof disclosed in "[3] Inorganic reducing agent" in International Publication No. WO 2011/040530 are applicable to the present invention.

(2-9) Other Additive Adding Step

An additive other than the aforementioned additives can be added to impart various functions to water absorbent resin in the present invention. Specific examples of such additives include surfactants, compounds with a phosphorous atom, oxidizing agents, organic reducing agents, water insoluble inorganic microparticles, organic powder such as metal soap, deodorants, antimicrobial agents, pulp, thermoplastic fibers and the like. The compounds disclosed in International Publication No. WO 2005/075070 and the compounds disclosed in "[5] Water insoluble inorganic microparticles" of International Publication No. WO 2011/040530 are applied as the surfactant and the water insoluble inorganic microparticles, respectively.

The amount of the additive used (amount added) is not particularly limited because the amount is appropriately determined in accordance with the application, but is preferably 3 parts by weight or less and more preferably 1 part by weight or less relative to 100 parts by weight of water absorbent resin powder. The additive can also be added in a step that is different from the above steps.

(2-10) Other Steps

Besides the steps discussed above, a surface treating (crosslinking) agent mixing step, a curing step, a granulating step, size aligning step, fine powder removing step, fine powder reusing step or the like can be provided as needed in the present invention. Further, one or two or more of transporting step, storing step, packing step, preserving step and the like can be further comprised. The "size aligning step" comprises the fine powder removing step after the surface crosslinking step or a step for classifying and pulverizing when water absorbent resin aggregates to exceed a desired size. Further, "fine powder reusing step" comprises a form of adding unprocessed fine powder as in the present invention, or adding fine powder prepared into large hydrogel in one of the manufacturing steps for water absorbent resin.

[3] Physical Properties of Polyacrylic Acid (Salt)-Based Water Absorbent Agent

A polyacrylic acid (salt)-based water absorbent agent obtained by the manufacturing method of the present invention desirably controls at least one or more, preferably two or more including CRC, more preferably 3 or more including CRC, and most preferably all physical properties set forth in the following (3-1) to (3-13) within a desirable range when using the water absorbent agent in a sanitation product, especially paper diapers. If these physical properties do not meet the following range, there is a risk of the effect of the present invention not being sufficient to attain sufficient performance in high concentration paper diapers.

Further, the shape of a polyacrylic acid (salt)-based water absorbent agent obtained by the manufacturing method of the present invention is not particularly limited, but is preferably particulate. This section explains the physical properties of a preferred form, a particulate water absorbent agent. The following physical properties were measured in accordance with the EDANA method unless specifically noted otherwise.

(3-1) CRC (Centrifuge Retention Capacity)

CRC (centrifuge retention capacity) of the water absorbent agent of the present invention is 30 g/g or greater. The upper limit value is not particularly limited. A higher value is preferred, but CRC is preferably 70 g/g or less, more preferably 50 g/g or less, and still more preferably 40 g/g or less from the viewpoint of balance with other physical properties.

If the CRC exceeds 70 g/g, the rate at which a bodily fluid such as urine or blood is absorbed decreases, so that such CRC is not suitable for use in high absorption rate paper diapers or the like. CRC can be controlled with an internal crosslinking agent, surface crosslinking agent or the like.

CRC (centrifuge retention capacity) of the water absorbent agent of the present invention can be appropriately adjusted by the following "[4] Method of adjusting physical properties of polyacrylic acid (salt)-based water absorbent agent".

(3-2) AAP (Absorption Against Pressure)

AAp (absorption against pressure) of the water absorbent agent of the present invention is preferably 20 g/g or greater, more preferably 22 g/g or greater, still more preferably 23 g/g or greater, particularly preferably 24 g/g or greater, and most preferably 25 g/g or greater. The upper limit value is not particularly limited, but is preferably 30 g/g or less.

If the AAP is less than 20 g/g, the amount of liquid returned when pressure is applied to an absorbent core (generally referred to as "Re-Wet") increases, so that such AAP is not suitable as an absorbent core of a sanitation product such as paper diapers. AAP can be controlled with particle size, surface crosslinking agent, or the like.

(3-3) Particle Size (Particle Size Distribution, Weight Average Particle Diameter (D50), Logarithmic Standard Deviation ($\sigma\zeta$) of Particle Size Distribution)

Particle size (particle size distribution, weight average particle diameter (D50), logarithmic standard deviation ($\sigma\zeta$) of particle size distribution) of a water absorbent agent of the invention is controlled to be the same as the particle size of water absorbent agent powder (water absorbent resin powder) prior to surface crosslinking. Specifically, weight average particle diameter (D50) is preferably 200 to 600 μm, more preferably 200 to 550 μm, still more preferably 250 to 500 μm, and particularly preferably 350 to 450 μm. Further, the ratio of particles with a particle diameter of less than 150 μm is preferably 10% by weight or less, more preferably 5% by weight or less, and still more preferably 1% by weight or less, and the ratio of particles with a diameter of 850 μm or greater is preferably 5% by weight of less, more preferably 3% by weight or less, and still more preferably 1% by weight of less. The lower limit value of the ratio of these particles is preferably as low as possible in each case. 0% by weight is desirable, but may be about 0.1% by weight. Furthermore, logarithmic standard deviation (σζ) of particle size distribution is preferably 0.20 to 0.50, more preferably 0.25 to 0.40, and still more preferably 0.27 to 0.35. These granularities are measured using a standard sieve in accordance with the measurement method disclosed in U.S. Pat. No. 7,638,570 or EDANA ERT420.2-02.

(3-4) Ext (Water-Soluble Component)

Ext (water-soluble component) of the water absorbent agent of the present invention has an upper limit value that is generally 50% by weight or less, preferably 35% by weight of less, and more preferably 25% by weight of less. The lower limit value is preferably 10% by weight or greater, more preferably the amount of soluble component of the water absorbent agent is 13% by weight or greater, and still more preferably 15% by weight of greater.

If the Ext exceeds 50% by weight, there is a risk of obtaining a water absorbent agent with weak gel strength and poor liquid permeability. Furthermore, this results in higher Re-Wet, which is not suitable as an absorbent core of a sanitation product such as paper diapers. Ext can be controlled with an internal crosslinking agent or the like.

(3-5) Amount of Water Soluble Polymer and Soluble Component Ratio

Hereinafter, the amount of water soluble polymer may be abbreviated as "amount of water-soluble component" or "amount of soluble component". A water soluble polymer is also referred to as "water-soluble component" or "soluble component". A "soluble component ratio" is the ratio (I by weight) of soluble component in a water absorbent agent. "Soluble component ratio" may also be denoted, with % by weight as the unit, as "Ext", "water-soluble component", "soluble component", "amount of water-soluble component" or "amount of soluble component".

The amount of soluble component of the water absorbent agent of the present invention preferably has an upper limit of 50% by weight or less, 45% by weight or less, 40% by weight or less, 35% by weight or less, 30% by weight or less, 25% by weight or less, 20% by weight or less, 15% by weight or less, and 10% by weight or less. The upper limit is more preferably 35% by weight or less or 30% by weight of less. Although not wishing to be bound by any theory, this is because if the amount of soluble component exceeds 35% by mass, a water absorbent agent may have weak gel strength and poor liquid permeability. This is also because absorption ratio (CRC, AAP, and the like) can decrease over time when used for a long period of time in diapers. The amount of soluble component of the water absorbent agent of the present invention preferably has a lower limit of 10% by weight or greater, more preferably 13% by weight or greater, and still more preferably 15% by weight of greater. Possible combinations of the upper and lower limits of the amounts of soluble component are also within the scope of the present invention. More preferably, the amount of soluble component of the water absorbent agent of the present invention is 10% by weight or greater and 30% by weight or less. Although not wishing to be bound by any theory, an amount exceeding the upper limit of the preferred range is not preferable because a user may feel discomfort due to stickiness from a soluble component eluting out from a water absorbent agent that has absorbed a liquid in actual use of a water absorbing article using the water absorbent agent of the present invention. Further, an amount below the lower limit of the preferred range is not preferable because a large quantity of an internal crosslinking agent needs to be used, so that sufficient fluid retention capacity may not be attained.

The amount of soluble component of the water absorbent agent of the present invention can be appropriately adjusted by the following "[4] Method of adjusting physical properties of polyacrylic acid (salt)-based water absorbent agent".

(3-6) Water Content

Water content of the water absorbent agent of the present invention is preferably greater than 0% by weight and 15% by weight or less, more preferably 1 to 13% by weight, still more preferably 2 to 10% by weight, and particularly preferably 2 to 9% by weight.

The water content within the above range results in a water absorbent agent with excellent powder properties (e.g., fluidity, transportability, damage resistance, and the like).

(3-7) Residual Monomer

The residual monomer contained in the water absorbent agent of the present invention is, from the viewpoint of safety, preferably 500 ppm or less, more preferably 400 ppm or less, and still more preferably 300 ppm or less. The lower limit value is not particularly limited, but is preferably 0 ppm and more preferably about 10 ppm.

The residual monomer content within the above range results in a water absorbent agent with reduced stimulation to the skin or the like of the human body.

(3-8) FSR (Water Absorption Rate)

FSR (water absorption rate) of the water absorbent agent of the present invention is preferably 0.10 g/g/s or greater, more preferably 0.15 g/g/s or greater, still more preferably 0.20 g/g/s or greater, and particularly preferably 0.25 g/g/s or greater. The upper limit value is not particularly limited, but is preferably 5.0 g/g/s or less and more preferably 3.0 g/g/s or less.

The FSR of less than 0.10 g/g/s is not suitable as an absorbent core of a sanitation product such as paper diapers because there is a risk of a bodily fluid such as urine or blood not being sufficiently absorbed, resulting in fluid leakage. FSR can be controlled by bubble polymerization, particle size, or the like.

(3-9) Moisture Absorption Blocking Ratio

"Moisture absorption blocking" refers to a phenomenon of water absorbent resins aggregating with one another when absorbing moisture. "Moisture absorption blocking ratio" refers to the ratio of aggregation. The moisture absorption blocking ratio is calculated by the method described in the Example [Measurement of physical properties of water absorbent agent] (c) discussed below. The moisture absorption blocking ratio of the water absorbent agent of the present invention is adjusted by adding a moisture absorption fluidity improving agent to preferably 50% by mass or less, more preferably 30% by mass or less, and still more preferably 10% by mass or less. The lower limit value is 0% by mass or greater due to the nature of calculation. The amount of moisture absorption fluidity improving agent added can be adjusted in the range of 0% by mass to 1% by mass relative to the water absorbent agent to achieve the above moisture absorption blocking ratio. Although not wishing to be bound by any theory, the moisture absorption blocking ratio can be controlled to be low to stably use a water absorbent agent under any operational environment of usage conditions of the user (e.g., operation conditions in a diaper manufacturing process).

(3-10) Molecular Weight of Soluble Component

"Molecular weight of soluble component" or "soluble component molecular weight" refers to the weight average molecular weight of a soluble component. The molecular weight of a soluble component of the water absorbent agent of the present invention is preferably in the range of 50,000 Daltons or greater and 1,000,000 Daltons or less, more preferably 100,000 Daltons or greater and 800,000 Daltons or less, 150,000 Daltons or greater and 700,000 Daltons or less, 200,000 Daltons or greater and 700,000 Daltons or less, 150,000 Daltons or greater and 600,000 Daltons or less, or 200,000 Daltons or greater and 600,000 Daltons or less, and most preferably 200,000 Daltons or greater and 550,000 Daltons or less. Although not wishing to be bound by any theory, this is because a molecular weight within this range can exert an excellent effect of reducing stickiness in a water absorbent agent. The molecular weight of a soluble component of the water absorbent agent of the present invention preferably has a lower limit value of 30,000, 40,000, 50,000, 75,000, 100,000, 125,000, 150,000, 175,000, 200,000, 225,000, or 250.000 Daltons, and preferably has an upper limit value of 1,000,000, 900,000, 800,000, 700,000, 600,000, or 500,000. Possible combinations of the upper limit and lower limit values are also within the scope of the present invention. The weight average molecular weight of a soluble component of the water absorbent agent of the present invention can be calculated by the method described in the [Measurement of physical properties of water absorbent agent] (d) discussed below.

The molecular weight of a soluble component of the water absorbent agent of the present invention can be appropriately adjusted by the "[4] Method of adjusting physical properties of polyacrylic acid (salt)-based water absorbent agent" discussed below.

(3-11) Intrinsic Viscosity (IV) of Soluble Component

The intrinsic viscosity (IV) of a soluble component of the water absorbent agent of the present invention is preferably 0.5 to 4.5 dl/g, more preferably 0.8 to 4.2 dl/g, 1.0 to 3.8 dl/g, or 1.5 to 4.0 dl/g, and most preferably 1.5 to 3.5 dl/g. Although not wishing to be bound by any theory, this is because the above intrinsic viscosity (IV) of a soluble component reduces stickiness in tactile sensation evaluation of water absorbent agents. The intrinsic viscosity (IV) of a soluble component of the water absorbent agent of the present invention preferably has a lower limit value of 0.3, 0.4, 0.5, 0.6, 0.7, 0.8, 0.9, 1.0, 1.1, 1.2, 1.3, 1.4, 1.5, 1.6, 1.7, or 1.8 dl/g, and preferably an upper limit value of 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, or 3.0 dl/g. Possible combinations of the upper limit and lower limit values are also within the scope of the present invention. The intrinsic viscosity (IV) of a soluble component of the water absorbent agent of the present invention can be calculated by the method described in the [Measurement of physical properties of water absorbent agent] (d) discussed below.

(3-12) Soluble Component Molecular Weight Reduction Ratio (%)

"Soluble component molecular weight reduction ratio (%)" refers to a ratio of reduction of the molecular weight of a soluble component of a water absorbent agent containing an α-hydroxycarboxylic acid to the molecular weight of a soluble component of a water absorbent agent not containing an α-hydroxycarboxylic acid with the same CRC. The soluble component molecular weight reduction ratio (%) of the present invention is preferably 8% or greater, 9% or greater, 10% or greater, 11% or greater, 12% or greater, or 14% or greater, and most preferably 15% or greater. The upper limit value is not particularly limited, but is preferably 50% or less, and more preferably 40% or less. Possible combinations of the upper limit and lower limit values of the soluble component molecular weight reduction ratio (%) are also within the scope of the present invention. The soluble component molecular weight reduction ratio (%) of the water absorbent agent of the present invention can be calculated by the method described in the [Measurement of physical properties of water absorbent agent] (e) discussed below. The soluble component molecular weight reduction ratio (%) of a water absorbent agent can be used as an indicator of stickiness of the water absorbent agent after absorbing a liquid. Stickiness of a water absorbent agent can be considered reduced when the ratio is preferably 8% or greater, 9% or greater, 10% or greater, 11% or greater, 12% or greater, or 14% or greater, and most preferably 15% or greater.

(3-13) Stickiness of Water Absorbent Agent

Stickiness of the water absorbent agent of the present invention after absorbing a liquid is defined by a tactile sensation evaluation of an eluted soluble component on a non-woven fabric upon absorption of a pseudo-sanitation agent. Tactile sensation evaluation is specifically conducted by the method described in the [Measurement of physical properties of water absorbent agent] (f) Tactile sensation evaluation discussed below. Stickiness can be considered reduced when tactile sensation evaluation is preferably 2.5 or less, 2.3 or less, 2.1 or less, 2.0 or less, or 1.8 or less, and most preferably 1.5 or less.

(3-14) Stability of Coloration Over Time

Water absorbent agents obtained in the present invention can be suitably used for sanitation materials such as paper diapers, where significantly clear white color is maintained even in long term storage under high humidity or temperature conditions. Furthermore, a water absorbent agent obtained by the above manufacturing method is a water absorbent agent with color stability over time, exhibiting an L value (Lightness) of at least 70, more preferably 74 or greater, and particularly preferably 78 or greater in the Hunter Lab color scale measurement of particles exposed to an atmosphere with a temperature of 70±1° C. and relative humidity of 65±1% for 7 days with a spectrocolorimeter (the upper limit of an L value is generally 100, but 70 would not cause a substantial problem in actual use).

Yellowness (YI value/Yellow Index/see EP Patent No. 942014 and 1108745) before a coloration promotion test is preferably 0 to 30, more preferably 0 to 25, 0 to 23, 0 to 20, or 0 to 18, more preferably 0 to 13, still more preferably 0 to 10, and most preferably 0 to 5, and it is preferable to have hardly any yellow tinge. Furthermore, yellowness after a coloration promotion test under a temperature of 70±1° C. and relative humidity of 65±1% for 7 days defined in the Examples is 26.5 or less, exhibiting a surprisingly yellowing preventing property even after exposure to a harsh high temperature high humidity condition.

(3-15) Amount of Fe/L-as Degradable Soluble Component

The amount of Fe/L-as degradable soluble component (defined by the measurement method described in the Examples) is controlled to preferably 0 to 30% by weight, more preferably 0 to 25% by weight, and still more preferably 0 to 20% by weight by water content corrected value.

(3-16) Surface Tension

Surface tension (defined by the measurement method described in the Examples) is preferably 60 [mN/m] or greater, more preferably 65 [mN/m] or greater, still more preferably 67 [mN/m] or greater, particularly preferably 70 [mN/m] or greater, and most preferably 72 [mN/m] or greater, with no substantial decrease in surface tension. The upper limit is generally sufficient with 75 [mN/m].

[4] Method of Adjusting Physical Properties of Polyacrylic Acid (Salt)-Based Water Absorbent Agent The centrifuge retention capacity of the water absorbent agent of the present invention can be appropriately adjusted mainly by adjusting at least one selected from the group consisting of the amount of internal crosslinking agent in a polymerization step, the amount of α-hydroxycarboxylic acid (salt), concentration of monomer component, and heating temperature and heating time in a surface crosslinking step. Examples of the internal crosslinking agent and the amount thereof, and the α-hydroxycarboxylic acid (salt) and the amount thereof include the compounds and the amount described in (Internal crosslinking agent) and (α-hydroxycarboxylic acid (salt)) in "[2] Method of manufacturing polyacrylic acid (salt)-based water absorbent resin", respectively. Examples of the concentration of the monomer component include the concentration described in (Concentration of monomer component) in "[2] Method of manufacturing polyacrylic acid (salt)-based water absorbent resin". Examples of the heating temperature and heating time in a surface crosslinking step include the heating temperature and heating time described in (Heating step) in (2-6) Surface crosslinking step of "[2] Method of manufacturing polyacrylic acid (salt)-based water absorbent resin".

The amount of soluble component of the water absorbent agent of the present invention can be appropriately adjusted mainly by adjusting at least one selected from the group consisting of the concentration of a monomer component and the amount of internal crosslinking agent in a polymerization step. Examples of the internal crosslinking agent and the amount thereof include the compounds and the amount used described in (Internal crosslinking agent) in "[2] Method of manufacturing polyacrylic acid (salt)-based water absorbent resin". Examples of the concentration of the monomer component include the concentration described in (Concentration of monomer component) in "[2] Method of manufacturing polyacrylic acid (salt)-based water absorbent resin".

The molecular weight of soluble component of the water absorbent agent of the present invention can be appropriately adjusted mainly by adjusting at least one selected from the group consisting of the concentration of a monomer component, the amount of α-hydroxycarboxylic acid and the amount of internal crosslinking agent in a polymerization step. Examples of the internal crosslinking agent and the amount thereof, and the α-hydroxycarboxylic acid (salt) and the amount thereof include the compounds and the amount used described in (Internal crosslinking agent) and (α-hydroxycarboxylic acid (salt)) in "[2] Method of manufacturing polyacrylic acid (salt)-based water absorbent resin", respectively. Examples of the concentration of the monomer component include the concentration described in (Concentration of monomer component) in "[2] Method of manufacturing polyacrylic acid (salt)-based water absorbent resin".

[5] Application of Polyacrylic Acid (Salt)-Based Water Absorbent Agent

The applications of the water absorbent agent of the present invention are not particularly limited, but preferred examples include applications in absorbent core for a sanitation product such as paper diapers, sanitary napkins, and incontinence pads. In particular, the water absorbent agent can be used as an absorbent core of a high concentration paper diaper (those with high amount of water absorbent agent used per sheet of paper diaper), which had problems in odor from the raw material, coloration, and the like. Furthermore, a significant effect can be expected when used on the top layer of the absorbent core.

Besides water absorbent agents, water absorbent materials such as pulp fiber can be used as the absorbent core. In such a case, the content (core concentration) of water absorbent agent in an absorbent core is preferably 20 to 100% by weight, more preferably 40 to 100% by weight, still more preferably 50 to 100% by weight, still even more preferably 60 to 100% by weight, particularly preferably 70 to 100% by weight, and the most preferably 75 to 95% by weight.

The core concentration in the above range allows a water absorbent article to maintain a white color with cleanliness when using the absorbent core in the top layer of a water absorbent article. Furthermore, it has excellent diffusibility of bodily fluid such as urine or blood, so that an increase in the amount of absorption is expected by efficient fluid distribution.

[6] Explanation of Preferred Embodiments

The preferred embodiments of the present invention are described hereinafter. It is understood that the following embodiments are provided to facilitate the understanding of the present invention, so that the scope of the present invention is not limited to the following descriptions. It is apparent that those skilled in the art can refer to the descriptions herein to make appropriate modifications within the scope of the present invention. It is understood that the following embodiments of the present invention can be used alone or as a combination thereof.

(6-1) Preferred Embodiments of Method of Manufacturing Water Absorbent Agent of the Present Invention In one aspect of the present invention, a method of manufacturing a water absorbent with a centrifuge retention capacity (CRC) of 30 g/g or greater, comprising of subjecting an aqueous monomer solution comprising an acrylic acid (salt) to a polymerization step, a drying step, and a surface crosslinking step, wherein the method comprises a step of adding an α-hydroxycarboxylic acid (salt) before the drying step is provided. Although not wishing to be bound by any theory, this is because addition of an α-hydroxycarboxylic acid (salt) before a drying step in the manufacture of a water absorbent with high fluid retention capacity reduces the molecular weight of a soluble component in the generated polymer and reduces the molecular weight of a soluble component eluting out when swollen after absorbing a liquid to reduce the viscosity, resulting in reduced stickiness or discomfort upon use as a sanitation material.

Addition of any additive before the drying step may be referred to as internal addition, and addition of any additive after the drying step may be referred to as external addition.

It was found that the present invention can internally add an α-hydroxycarboxylic acid (salt) in the manufacture of a water absorbent with a high fluid retention capacity to reduce the molecular weight of a soluble component eluting out when the water absorbent agent swells after absorbing a liquid, resulting in a reduction of stickiness leading to discomfort upon actual use of paper diapers or the like.

Any chelating agent (e.g., diethylenetriaminepentaacetic acid (DTPA), ethylenediamine tetra(methylenephosphonic acid) (EDTMP), or the like) can be externally added to the water absorbent agent of the present invention from the viewpoint of the hue (prevention of coloration), prevention of degradation, or the like. Furthermore, an α-hydroxycarboxylic acid (salt) may be internally added and any chelating agent (e.g., diethylenetriaminepentaacetic acid (DTPA) or a salt thereof, ethylenediamine tetra(methylenephosphonic acid) (EDTMP) or a salt thereof, or the like) may be externally added to the water absorbent agent of the present invention from the viewpoint of the hue (prevention of coloration), prevention of degradation, or the like.

In the present invention, Examples of preferred centrifuge retention capacity (CRC) of a water absorbent include 30 g/g or greater, 31 g/g or greater, 32 g/g or greater, 33 g/g or greater, 34 g/g or greater, 35 g/g or greater, 36 g/g or greater, 37 g/g or greater, 38 g/g or greater, 39 g/g or greater, 40 g/g or greater, 41 g/g or greater, 42 g/g or greater, 43 g/g or greater, 44 g/g or greater, and 45 g/g. The centrifuge retention capacity (CRC) is particularly preferably 30 g/g or greater. For a water absorbent agent with centrifuge retention capacity of less than 30 g/g under the above conditions, a reduction in the molecular weight of soluble component is not observed so that stickiness of a water absorbent after absorbing a liquid, which is the problem to be solved of the present invention, does not occur.

In one preferred embodiment, the water absorbent agent has reduced stickiness after absorbing a liquid. A reduction in stickiness of a water absorbent can be defined, with a ratio of reduction in the molecular weight of a soluble component of the water absorbent agent (i.e., soluble component molecular weight reduction ratio (%)) as an indicator. Stickiness of a water absorbent can be considered reduced when the soluble component molecular weight reduction ratio (%) of a water absorbent is preferably 8% or greater, 9% or greater, 10% or greater, 11% or greater, 12% or greater, or 14% or greater, and most preferably 15% or greater.

In one preferred embodiment, the α-hydroxycarboxylic acid (salt) is added before, during, or after the polymerization step. More preferably, the α-hydroxycarboxylic acid (salt) is added before or during the polymerization step. Specifically, the α-hydroxycarboxylic acid (salt) is preferably added to an aqueous monomer solution before polymerization. Alternatively, the α-hydroxycarboxylic acid (salt) is preferably added to an aqueous monomer solution after initiation of polymerization, specifically after 2 minutes from initiation of polymerization. The α-hydroxycarboxylic acid (salt) may be added at any point (e.g., after 1 minute, 2 minutes, 3 minutes, 5 minutes, 10 minutes, 20 minutes or the like after initiation of polymerization) from the initiation of polymerization to the end of polymerization of an aqueous monomer solution.

In another preferred embodiment, the method further comprises a gel grinding step after the polymerization step and before the drying step, and the α-hydroxycarboxylic acid (salt) is added before or during the step for gel grinding. More preferably, the α-hydroxycarboxylic acid (salt) is added during the gel grinding step. Specifically, the α-hydroxycarboxylic acid (salt) is added upon gel grinding hydrogel obtained after polymerization.

In the most preferred embodiment, the α-hydroxycarboxylic acid (salt) is added before or during the polymerization step.

In one preferred embodiment, an amount of the α-hydroxycarboxylic acid (salt) to be added is 0.010 to 4.0 mol % with respect to the acrylic acid (salt). More preferably, the amount of the α-hydroxycarboxylic acid (salt) to be added is 0.025 to 2.5 mol % or 0.05 to 1.0 mol % and most preferably 0.1 to 1.0 mol % with respect to the acrylic acid (salt). Although not wishing to be bound by any theory, this is because the amount is preferred from the viewpoint of water absorbing properties or reduction in the molecular weight of a soluble component. The amount of the α-hydroxycarboxylic acid (salt) to be added preferably has a lower limit value of 0.005, 0.006, 0.007, 0.008, 0.009, 0.010, 0.011, 0.012, 0.015, 0.02, 0.025, 0.03, 0.035, 0.040, 0.05, 0.055, 0.06, 0.065, 0.07, 0.075, 0.08, 0.085, 0.09, 0.1, 0.11, 0.12, 0.15, or 0.2 mol %, and upper limit value of 5.0, 4.5, 4.0, 3.5, 3.0, 2.5, 2.0, 1.5, 1.0, or 0.5 mol %. Possible combinations of the upper and lower limit values are also within the scope of the present invention.

In one preferred embodiment, the α-hydroxycarboxylic acid (salt) is one or more selected from the group consisting of lactic acid (salt), glycolic acid (salt), malic acid (salt), glyceric acid (salt), tartaric acid (salt), citric acid (salt), isocitric acid (salt), mevalonic acid (salt), quinic acid (salt), shikimic acid (salt), β-hydroxypropionic acid (salt), salicylic acid (salt), creosotic acid (salt), vanillic acid (salt), syringic acid (salt), resorcylic acid (salt), pyrocatechuic acid (salt), protocatechuic acid (salt), gentisic acid (salt), orsellinic acid (salt), mandelic acid (salt) and gallic acid (salt). One or more of these acids (salts) may be used in combination as the α-hydroxycarboxylic acid (salt). Preferably, the α-hydroxycarboxylic acid (salt) is one or more selected from the group consisting of a malic acid (salt) and a lactic acid (salt). A malic acid (salt) and a lactic acid (salt) may be used in combination as the α-hydroxycarboxylic acid (salt). Most preferably, the α-hydroxycarboxylic acid (salt) is a malic acid (salt).

In one preferred embodiment, a centrifuge retention capacity (CRC) before crosslinking of the water absorbent agent is preferably greater than 34 g/g, greater than 36 g/g, greater than 38 g/g, greater than 40 g/g, greater than 42 g/g, greater than 44 g/g, greater than 46 g/g, greater than 48 g/g, greater than 50 g/g, greater than 52 g/g, or greater than 54 g/g. A particularly preferred centrifuge retention capacity (CRC) before crosslinking of the water absorbent agent is greater than 34 g/g. For a water absorbent agent with centrifuge retention capacity of less than 30 g/g under the above conditions, a reduction in the molecular weight of soluble component is not observed, so that stickiness of a water absorbent agent, which is the problem to be solved of the present invention, does not occur.

In one preferred embodiment, an amount of soluble component of the water absorbent agent is 8% by weight or greater and 30% by weight or greater, 10% by weight or greater and 30% by weight or less, 13% by weight or greater and 30% by weight of less, 15% by weight of greater and 30% by weight or less, 17% by weight or greater and 30% by weight or less, 10% by weight or greater and 35% by weight or less, 13% by weight or greater and 35% by weight or less, 15% by weight of greater and 35% by weight or less, 10% by weight or greater and 25% by weight or less, 13% by weight or greater and 25% by weight or less, or 15% by weight or greater and 25% by weight or less. Preferably, the lower limit is 10% by weight or greater, more preferably 13% by weight or greater, and still more preferably 15% by weight or greater. Preferably the upper limit is 30% by weight or less. More preferably, an amount of a soluble component of the water absorbent agent is 10% by weight or greater and 30% by weight or less. Although not wishing to be bound by any theory, an amount exceeding the upper limit of the preferred range is not preferable because a user may feel discomfort due to stickiness from a soluble component eluting out from a water absorbent agent that has absorbed a liquid in actual use of a water absorbent article using the water absorbent agent of the present invention. Further, an amount below the lower limit of the preferred range is not preferable because a large quantity of an internal crosslinking agent needs to be used, so that sufficient fluid retention capacity may not be attained.

In one preferred embodiment, the molecular weight of a soluble component of the water absorbent agent is in the range of 50,000 Daltons or greater and 1,000,000 Daltons or less, more preferably 100,000 Daltons or greater and 800,000 Daltons or less, 150,000 Daltons or greater and 700,000 Daltons or less, 200,000 Daltons or greater and 700,000 Daltons or less, 150,000 Daltons or greater and 600,000 Daltons or less, or 200,000 Daltons or greater and 600,000 Daltons or less, and most preferably 200,000 Daltons or greater and 550,000 Daltons or less. Although not wishing to be bound by any theory, this is because a molecular weight within this range can exert an excellent effect of reducing stickiness in a water absorbent agent. Thus, reduction in stickiness of a water absorbent agent can be defined with the molecular weight of a soluble component of the water absorbent agent as an indicator. Stickiness of a water absorbent agent can be considered reduced when the molecular weight of a soluble component is preferably 200,000 Daltons or greater and 700,000 Daltons or less, and most preferably 200,000 Daltons or greater and 550,000 Daltons or less.

In one preferred embodiment, the surface crosslinking step is performed after the drying step. Preferably, a surface crosslinking step comprises at least one of the steps described in "(2-6) Surface crosslinking step".

In one preferred embodiment, a method comprises a step of measuring an amount of iron component in a raw material, caustic soda (NaOH). The following amount of iron component is measured by a known method, such as ICP (high frequency inductively coupled plasma) emission spectroscopy. The amount of iron component in raw material NaOH is, as iron oxide ($Fe_2O_3$), preferably 10 ppm or less, more preferably 5 ppm or less, still more preferably 2 ppm or less, and most preferably 1 ppm or less.

In one preferred embodiment, the method further comprises at least one of classification step, surface crosslinking step, re-humidification step, granulating step, size aligning step, fine powder removing step, and fine powder reusing step.

In one preferred embodiment, the method further comprises a step of reusing fine powder generated in the manufacture of the water absorbent agent. Preferably, fine powder is generated in any of the steps after a polymerization step. More preferably, fine powder is generated during or after a step selected from the group consisting of a gel grinding step, drying step, pulverizing step, classification step, surface crosslinking step, re-humidification step, granulating step, size aligning step, and fine powder removing step. Still more preferably, fine powder is mainly generated during or after a pulverizing step.

In one embodiment, the drying step comprises a step of performing at least one drying procedure selected from the group consisting of heat drying, hot-air drying, vacuum drying, fluidized bed drying, infrared drying, microwave drying, drum dryer drying, azeotropic dehydration drying with a hydrophobic organic solvent, and high humidity drying with use of high-temperature vapor at preferably 120 to 250° C. and more preferably 150 to 200° C., and for preferably 5 to 120 minutes, more preferably 10 to 90 minutes, and still more preferably 15 to 60 minutes. A more preferred drying procedure is hot air drying using an endless belt or drum dryer drying from the viewpoint of hue and drying efficiency.

In one preferred embodiment, a peak temperature during a polymerization reaction of the aqueous monomer solution in the polymerization step is 85° C. or greater. In a more preferred embodiment, a peak temperature during a polymerization reaction of the aqueous monomer solution in the polymerization step is 90° C. or greater. Specifically, the peak temperature during a polymerization reaction of the aqueous monomer solution in the polymerization step is preferably 85° C. or greater, 86° C. or greater, 87° C. or greater, 88° C. or greater, 89° C. or greater, or 90° C. or greater. The upper limit value is preferably 100° C. or less, 98° C. or less, or 95° C. or less.

In one preferred embodiment, the method further comprises a step of adding a chelating agent after the drying step. This is because adding a chelating agent can impart a water absorbent agent with an effect of hue (prevention of coloration), prevention of degradation, or the like.

In one preferred embodiment, the amount of chelating agent added after the drying step is 0.001 to 5.0 parts by weight, 0.002 to 3.0 parts by weight, 0.003 to 1.0 parts by weight, or 0.004 to 0.5 parts by weight and particularly preferably 0.005 to 0.2 parts by weight relative to 100 parts by weight of water absorbent agent. Although not wishing to be bound by any theory, this is because this amount is preferred from the viewpoint of hue (prevention of coloration), prevention of degradation, or the like. The amount of chelating agent to be added preferably has a lower limit value of 0.0005, 0.001, 0.0015, 0.002, 0.0025, 0.003, 0.0035, 0.004, 0.0045, 0.005, 0.0055, or 0.006 parts by weight, and preferably has a upper limit value of 6.0, 5.5, 5.0, 4.5, 4.0, 3.5, 3.0, 2.5, 2.0, 1.5, 1.0, 0.7, 0.6, 0.5, 0.4, 0.3, 0.2, or 0.1 parts by weight. Possible combinations of the upper and lower limits are also within the scope of the present invention.

In one preferred embodiment, the chelating agent includes phosphorous-based chelating agents and aminocarboxylic acid-based chelating agents.

A preferred phosphorous-based chelating agent is selected from the group consisting of ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), ethylenediamine tetra(methylenephosphonic acid) (EDTMP), polymethylenediamine tetra(methylenephosphonic acid), diethylenetriamine penta(methylenephosphonic acid), 1-hydroxyethylidene diphosphonic acid, and salts thereof. Preferably, the phosphorous-based chelating agent is selected from ethylenediamine tetra(methylenephosphonic acid) and a salt thereof. More preferably, the phosphorous-based chelating agent is sodium salt of ethylenediamine tetra(methylenephosphonic acid). Still more preferably, the phosphorous-based chelating agent is ethylenediamine tetra (methylenephosphonic acid)pentasodium.

A preferred aminocarboxylic acid-based chelating agent is selected from the group consisting of iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyclohexane tetraacetic acid, bis(2-hydroxyethyl) glycine, diaminopropanol tetraacetic acid, ethylenediamine-2-propionic acid, glycol ether diamine tetraacetic acid, bis(2-hydroxybenzyl) ethylenediaminediacetic acid, 3-hydroxy-2, 2-iminodisuccinic acid, iminodisuccinic acid, methylglycinediacetic acid and salts thereof. More preferably, the aminocarboxylic acid-based chelating agent is a sodium salt of diethylenetriaminepentaacetic acid. Still more preferably, the aminocarboxylic acid-based chelating agent is diethylenetriaminepentaacetic acid trisodium.

The chelating agent in the present invention is most preferably diethylenetriaminepentaacetic acid or a salt thereof (DTPA) or a salt thereof, or ethylenediamine tetra (methylenephosphonic acid) (EDTMP) or a salt thereof.

In one preferred embodiment, the method further comprises a step of adding a moisture absorption fluidity improving agent after the drying step. This is because, for example, fluidity and liquid permeability in a dry state can be significantly improved and blocking upon moisture absorption can be suppressed thereby.

In one preferred embodiment, the moisture absorption fluidity improving agent comprises at least one selected from the group consisting of silicon dioxide (silica), phosphate, and hydrotalcite.

In one aspect of the present invention, a water absorbent agent obtained by the method of manufacturing a water absorbent of the present invention described herein is provided.

In one aspect of the present invention, an absorbent core comprising the water absorbent agent obtained by the method of manufacturing a water absorbent agent of the present invention described herein is provided.

In one aspect of the present invention, a sanitation article comprising the absorbent core comprising the water absorbent agent obtained by the method of manufacturing a water absorbent agent of the present invention described herein is provided. Although not wishing to be bound by any theory, this is because the sanitation article can reduce the molecular weight of a soluble component eluted out when a water absorbent agent swells after absorbing a liquid, resulting in reduction of stickiness leading to discomfort upon actual use of paper diapers or the like.

(6-2) Most Preferred Embodiment of Method of Manufacturing a Water Absorbent Agent In one aspect of the present invention, the present invention provides a method of manufacturing a polyacrylic acid (salt)-based absorbent agent, comprising a step of polymerizing an aqueous monomer solution having an acrylic acid (salt) as a main component in the presence of an α-hydroxycarboxylic acid (salt), wherein at least one of the post-polymerization step is performed in the presence of a chelating agent. Although not wishing to be bound by any theory, this is because a water absorbent agent with both strong urine resistance and resistance to coloration over time can be manufactured by polymerizing in the presence of an α-hydroxycarboxylic acid (salt) and performing at least one step performed after polymerization in the presence of a chelating agent.

In one preferred embodiment, the post-polymerization step is selected from the group consisting of a drying step, a surface treating (crosslinking) agent mixing step, a surface crosslinking (surface treating) step, a granulating step, and a curing step. Preferably, the steps performed in the method of manufacturing a water absorbent agent of the present invention are performed in the order of a drying step, a surface treating (crosslinking) agent mixing step, a surface crosslinking (surface treating) step, a granulating step, and a curing step.

In one preferred embodiment, the step of polymerizing is performed in the presence of the chelating agent. Although not wishing to be bound by any theory, this is because urine resistance of a water absorbent agent obtained thereby is further improved.

In one preferred embodiment, a ratio of a chelating agent that is added in the step of polymerizing and a chelating agent added in the post-polymerization step is 1:1 to 1:20, 1:2 to 1:20, 1:3 to 1:20, 1:4 to 1:20, 1:5 to 1:20, 1:6 to 1:20, 1:7 to 1:20, 1:8 to 1:20, 1:9 to 1:20, 1:10 to 1:20, 1:11 to 1:20, 1:12 to 1:20, 1:13 to 1:20, 1:14 to 1:20, 1:15 to 1:20, 1:16 to 1:20, 1:17 to 1:20, 1:18 to 1:20, 1:19 to 1:20, 1:1 to 1:19, 1:1 to 1:18, 1:1 to 1:17, 1:1 to 1:16, 1:1 to 1:15, 1:1 to 1:14, 1:1 to 1:13, 1:1 to 1:12, 1:1 to 1:11, 1:1 to 1:10, 1:1 to 1:9, 1:1 to 1:8, 1:1 to 1:7, 1:1 to 1:6, 1:1 to 1:5, 1:1 to 1:4, 1:1 to 1:3, or 1:1 to 1:2.

In one preferred embodiment, an amount of the chelating agent added in the post-polymerization step is 0.005 to 0.2 parts by weight, 0.006 to 0.2 parts by weight, 0.007 to 0.2 parts by weight, 0.008 to 0.2 parts by weight, 0.009 to 0.2 parts by weight, 0.01 to 0.2 parts by weight, 0.02 to 0.2 parts by weight, 0.03 to 0.2 parts by weight, 0.04 to 0.2 parts by weight, 0.05 to 0.2 parts by weight, 0.06 to 0.2 parts by weight, 0.07 to 0.2 parts by weight, 0.09 to 0.2 parts by weight, 0.005 to 0.09 parts by weight, 0.005 to 0.08 parts by weight, 0.005 to 0.07 parts by weight, 0.005 to 0.06 parts by weight, 0.005 to 0.05 parts by weight, 0.005 to 0.04 parts by weight, 0.005 to 0.03 parts by weight, 0.005 to 0.02 parts by weight, 0.005 to 0.01 parts by weight, 0.005 to 0.009 parts by weight, 0.005 to 0.008 parts by weight, 0.005 to 0.007 parts by weight, or 0.005 to 0.006 parts by weight relative to 100 parts by weight of absorbent agent.

In one preferred embodiment, content of an α-hydroxycarboxylic acid (salt) that is added in the step of polymerizing is 0.02 to 1.5 parts by weight, 0.03 to 1.5 parts by weight, 0.04 to 1.5 parts by weight, 0.05 to 1.5 parts by weight, 0.06 to 1.5 parts by weight, 0.07 to 1.5 parts by weight, 0.08 to 1.5 parts by weight, 0.09 to 1.5 parts by weight, 0.1 to 1.5 parts by weight, 0.2 to 1.5 parts by weight, 0.3 to 1.5 parts by weight, 0.4 to 1.5 parts by weight, 0.5 to 1.5 parts by weight, 0.6 to 1.5 parts by weight, 0.7 to 1.5 parts by weight, 0.8 to 1.5 parts by weight, 0.9 to 1.5 parts by weight, 1.0 to 1.5 parts by weight, 1.1 to 1.5 parts by weight, 1.2 to 1.5 parts by weight, 1.3 to 1.5 parts by weight, 1.4 to 1.5 parts by weight, 0.02 to 1.4 parts by weight, 0.02 to 1.3 parts by weight, 0.02 to 1.2 parts by weight, 0.02 to 1.1 parts by weight, 0.02 to 1.0 parts by weight, 0.02 to 0.9 parts by weight, 0.02 to 0.8 parts by weight, 0.02 to 0.7 parts by weight, 0.02 to 0.6 parts by weight, 0.02 to 0.5 parts by weight, 0.02 to 0.4 parts by weight, 0.02 to 0.3 parts by weight, 0.02 to 0.2 parts by weight, 0.02 to 0.1 parts by weight, 0.02 to 0.09 parts by weight, 0.02 to 0.08 parts by weight, 0.02 to 0.07 parts by weight, 0.02 to 0.06 parts by weight, 0.02 to 0.05 parts by weight, 0.02 to 0.04 parts by weight, or 0.02 to 0.03 parts by weight relative to 100 parts by weight of acrylic acid (salt).

In one preferred embodiment, the method comprises a step of classifying surface crosslinked (surface treated) water absorbent resin into multiple different granularities, a step of adding a chelating agent for each of the multiple different granularities, and a step of remixing multiple water absorbent resins after adding the chelating agent to obtain a water absorbent agent. Although not wishing to be bound by any theory, this is because a water absorbent agent with high gel stability, small variation in gel stability between granularities, and excellent water absorbing property (e.g., absorption against pressure, centrifuge retention capacity, liquid permeability, moisture absorption blocking resistance, low coloration and the like) can be obtained by appropriately changing the amount of chelating agent added for each of the multiple different granularities.

(6-3) Preferred Properties of Water Absorbent Agent of the Present Invention

In one aspect of the present invention, a surface-cross-linked polyacrylic acid (salt)-based water absorbent agent comprising an α-hydroxycarboxylic acid (salt) therein, wherein a centrifuge retention capacity (CRC) is 30 g/g or greater is provided.

In the present invention, the centrifuge retention capacity (CRC) of the water absorbent agent is preferably 30 g/g or greater, 31 g/g or greater, 32 g/g or greater, 33 g/g or greater, 34 g/g or greater, 35 g/g or greater, 36 g/g or greater, 37 g/g or greater, 38 g/g or greater, 39 g/g or greater, 40 g/g or greater, 41 g/g or greater, 42 g/g or greater, 43 g/g or greater, 44 g/g or greater, or 45 g/g or greater. A particularly preferable predetermined centrifuge retention capacity (CRC) is 30 g/g or greater. For a water absorbent agent with centrifuge retention capacity of less than 30 g/g under the above conditions, a reduction in the molecular weight of soluble component is not observed so that stickiness of a water absorbent agent after absorbing a liquid, which is the problem to be solved of the present invention, does not occur. The water absorbent agent of the present invention also encompasses water absorbent agents with the features described in the method described in (6-1).

In one preferred embodiment, the water absorbent agent has reduced stickiness after absorbing a liquid. Reduction in stickiness of a water absorbent agent can be defined with a ratio of reduction in the molecular weight of the water absorbent agent (i.e., soluble component molecular weight reduction ratio (%)) as an indicator. Stickiness of a water absorbent agent is considered reduced when the soluble component molecular weight reduction ratio of a water absorbent agent is preferably 8% or greater, 9% or greater, 10% or greater, 11% or greater, 12% or greater, or 14% or greater, and most preferably 15% or greater. Alternatively, reduction in stickiness of a water absorbent agent can be defined with the molecular weight of a soluble component of the water absorbent agent as an indicator. Stickiness of a water absorbent agent is considered reduced when the molecular weight of a soluble component is preferably 200,000 Daltons or greater and 700,000 Daltons or less, and most preferably 200,000 Daltons or greater and 550,000 Daltons or less.

In one aspect of the present invention, a water absorbent agent obtained by the method described in (6-1) is provided.

In one aspect of the present invention, an absorbent core comprising a water absorbent agent obtained by the method described in (6-1) or the water absorbent agent described in (6-3) is provided.

In one aspect of the present invention, a sanitation article comprising the absorbent core is provided. Although not wishing to be bound by any theory, this is because the sanitation article can reduce the molecular weight of a soluble component eluting out when a water absorbent agent swells after absorbing a liquid, resulting in reduction of stickiness leading to discomfort upon actual use of paper diapers or the like.

(6-4) Most Preferred Properties of Water Absorbent Agent of the Present Invention In one aspect, the present invention is a water absorbent agent comprised of a polyacrylic acid (salt) as main component, wherein a Fe/L-as degradable soluble component extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes is 35% by weight or less, 30% by weight or less, 25% by weight or less, 20% by weight or less, 15% by weight or less, 10% by weight or less, 5% by weight or less, or 0% by weight, and a YI value after a coloration promotion test is 26 or less is provided. The problem in incontinence or the like is that the presence of ascorbic acid in addition of iron component contained therein has a synergistically negative impact such as degradation, coloration or the like of a water absorbent agent. Such a synergistic negative impact could not be evaluated in the past. A system that can evaluate such a synergistically negative impact was developed for the first time using a degradation solution comprised of physiological saline comprising L-ascorbic acid and divalent iron ions, so that the effect on the impact can be evaluated. As a result of diligent research in the present invention with this evaluation system, an effect of improving such synergistically negative impact was found in a water absorbent agent with both strong urine resistance and resistance to coloration over time by a method of adding a chelating agent to a polyacrylic acid (salt)-based water absorbent agent obtained by polymerizing an aqueous monomer solution with an acrylic acid (salt) as a main component in the presence of an α-hydroxycarboxylic acid (salt).

While it is known that resistance to coloration over time is improved by adding an α-hydroxycarboxylic acid (salt) upon polymerization, urine resistance in the presence of iron is not desirable and problematic. Furthermore, the negative impact of iron component is further exacerbated in the presence of ascorbic acid. It was revealed by the evaluation system developed in the present invention that such a synergistic negative impact cannot be solved only by adding an α-hydroxycarboxylic acid (salt). It was found that this can be improved by combined use of an α-hydroxycarboxylic acid (salt) and a chelating agent in the present invention. Such an improvement was found to have a positive effective by adding a combination of a chelating agent at 0.001 to 1.0% by weight and an α-hydroxycarboxylic acid (salt) at 0.02 to 1.5% by weight. The amount of chelating agent present in a water absorbent agent is preferably (1A) 0.001 to 1.0 parts by weight, more preferably (1B) 0.001 to 0.5 part by weight, still more preferably (1C) 0.001 to 0.25 parts by weight, and particularly preferably (1D) 0.001 to 0.15 parts by weight relative to 100 parts by weight of water absorbent agent. The amount of α-hydroxycarboxylic acid (salt) present in a water absorbent agent is preferably (2A) 0.02 to 1.5 parts by weight, more preferably (2B) 0.05 to 1.0 parts by weight, and still more preferably (2C) 0.1 to 1.0 parts by weight relative to 100 parts by weight of the water absorbent agent. The amount of chelating agent present in a water absorbent agent is selected from any of (1A), (1B), (1C), and (1D), and the amount of chelating agent present in a water absorbent agent is selected form any of (2A), (2B), and (2C). A combination of the amount of α-hydroxycarboxylic acid (salt) present in a water absorbent agent and the amount of chelating agent present in a water absorbent agent is any combination of the above selections. It was completely unexpectedly found that combined use of an α-hydroxycarboxylic acid (salt) and a chelating agent is better for resistance to coloration over time than adding only one of the two.

An addition of sodium bisulfite (SBS) can potentially improve resistance to coloration over time, but there is a risk of metal corrosion in the manufacturing process when adding SBS to water absorbent resin. It was found that such a risk of metal corrosion can be improved by combined use of an α-hydroxycarboxylic acid (salt) and a chelating agent. Furthermore, it is known that resistance to coloration over time is improved by using ethylenediamine tetra(methylenephosphonic acid) (EDTMP). Meanwhile, there is a problem of worsening resistance to coloration over time or urine resistance in the presence of a multivalent metal component such as aluminum. The problem of coexistence of a multivalent metal can be solved by phosphoric acid granulation. Meanwhile, a large quantity, i.e., 1%, of phosphoric acid is added for phosphoric acid granulation, so that there is still a problem of worsening the water absorbing property or the like. It was revealed by the evaluation system developed in the present invention that these problems cannot be solved only by adding a chelating agent, or by a change to another chelating agent. It was found that this can be improved by combined use of an α-hydroxycarboxylic acid (salt) and a chelating agent in the present invention.

The water absorbent agent of the present invention exhibits an excellent value of Fe/L-as degradable soluble component, which is an indicator newly developed in the present invention, with respect to urine resistance in the presence of iron. Further, manufacture of the water absorbent agent of the present invention does not add sodium hydrogen sulfate, so that there is no risk of metal corrosion in the manufacturing process. The manufacture also does not add phosphoric acid, so that there is no problem of worsening water absorbing property or the like.

In a preferred embodiment, the water absorbent agent of the present invention comprises a chelating agent at 0.001 to 1.0% by weight, 0.002 to 1.0% by weight, 0.003 to 1.0% by weight, 0.004 to 1.0% by weight, 0.005 to 1.0% by weight, 0.010 to 1.0% by weight, 0.015 to 1.0% by weight, 0.020 to 1.0% by weight, 0.025 to 1.0% by weight, 0.030 to 1.0% by weight, 0.035 to 1.0% by weight, 0.040 to 1.0% by weight, 0.045 to 1.0% by weight, 0.050 to 1.0% by weight, 0.055 to 1.0% by weight, 0.060 to 1.0% by weight, 0.065 to 1.0% by weight, 0.070 to 1.0% by weight, 0.075 to 1.0% by weight, 0.080 to 1.0% by weight, 0.085 to 1.0% by weight, 0.090 to 1.0% by weight, 0.095 to 1.0% by weight, 0.1 to 1.0% by weight, 0.20 to 1.0% by weight, 0.3 to 1.0% by weight, 0.4 to 1.0% by weight, 0.5 to 1.0% by weight, 0.6 to 1.0% by weight, 0.7 to 1.0% by weight, 0.8 to 1.0% by weight, 0.9 to 1.0% by weight, 0.001 to 0.9% by weight, 0.001 to 0.8% by weight, 0.001 to 0.7% by weight, 0.001 to 0.6% by weight, 0.001 to 0.5% by weight, 0.001 to 0.4% by weight, 0.001 to 0.3% by weight, 0.001 to 0.2% by weight, 0.001 to 0.1% by weight, 0.001 to 0.095% by weight, 0.001 to 0.090% by weight, 0.001 to 0.085% by weight, 0.001 to 0.080% by weight, 0.001 to 0.075% by weight, 0.001 to 0.070% by weight, 0.001 to 0.065% by weight, 0.001 to 0.060% by weight, 0.001 to 0.055% by weight, 0.001 to 0.050% by weight, 0.001 to 0.045% by weight, 0.001 to 0.040% by weight, 0.001 to 0.035% by weight, 0.001 to 0.030% by weight, 0.001 to 0.025% by weight, 0.001 to 0.020% by weight, 0.001 to 0.015% by weight, or 0.005 to 0.010% by weight and an α-hydroxycarboxylic acid (salt) at 0.02 to 1.5% by weight, 0.03 to 1.5% by weight, 0.04 to 1.5% by weight, 0.05 to 1.5% by weight, 0.06 to 1.5% by weight, 0.07 to 1.5% by weight, 0.08 to 1.5% by weight, 0.09 to 1.5% by weight, 0.1 to 1.5% by weight, 0.2 to 1.5% by weight, 0.3 to 1.5% by weight, 0.4 to 1.5% by weight, 0.5 to 1.5% by weight, 0.6 to 1.5% by weight, 0.7 to 1.5% by weight, 0.8 to 1.5% by weight, 0.9 to 1.5% by weight, 1.0 to 1.5% by weight, 1.1 to 1.5% by weight, 1.2 to 1.5% by weight, 1.3 to 1.5% by weight, 1.4 to 1.5% by weight, 0.02 to 1.4% by weight, 0.02 to 1.3% by weight, 0.02 to 1.2% by weight, 0.02 to 1.1% by weight, 0.02 to 1.0% by weight, 0.02 to 0.9% by weight, 0.02 to 0.8% by weight, 0.02 to 0.7% by weight, 0.02 to 0.6% by weight, 0.02 to 0.5% by weight, 0.02 to 0.4% by weight, 0.02 to 0.3% by weight, 0.02 to 0.2% by weight, or 0.02 to 0.1% by weight.

In a particularly preferred embodiment, a preferred combination of concentrations in combining an α-hydroxycarboxylic acid (salt) and a chelating agent is 0.02 to 0.005% by weight of chelating agent added in a polymerization step, 0.01 to 0.09% by weight of chelating agent added in a post-polymerization step, and 0.02 to 1% by weight of α-hydroxycarboxylic acid (salt).

Especially for a chelating agent, the effect can be improved by further ingenuity in the addition upon manufacture. In a preferred embodiment, the chelating agent added in a step of polymerizing is DTPA, and the chelating agent added in a post-polymerization step is also DTPA. The ratio of a chelating agent that is presence in the step of polymerizing and a chelating agent that is present in the post-polymerizing step is 1:1 to 1:18. The amount of chelating agent added in a step of polymerizing is preferably 50 to 200 (mg/kg), and the amount of chelating agent added in a post-polymerization step is preferably 100 to 900 (mg/kg).

In a preferred embodiment, a YI value after a coloration promotion test is 26.5 or less, 26 or less, 25.5 or less, 25 or less, 24.5 or less, 24 or less, 23.5 or less, 23 or less, 22.5 or less, 22 or less, 21.5 or less, 21 or less, 20.5 or less, 20 or less, 19.5 or less, 19 or less, 18.5 or less, 18 or less, 17.5 or less, 17 or less, 16.5 or less, 16 or less, 15.5 or less, 15 or less, 14.5 or less, 14 or less, 13.5 or less, 13 or less, 12.5 or less, 12 or less, 11.5 or less, 11 or less, 10.5 or less, 10 or less, 9.5 or less, 9 or less, 8.5 or less, 8 or less, 7.5 or less, 7 or less, 6.5 or less, 6 or less, 5.5 or less, 5 or less, 4.5 or less, 4 or less, 3.5 or less, 3 or less, 2.5 or less, 2 or less, 1.5 or less, 1 or less, 0.5 or less, or 0. A YI value after a coloration promotion test is more preferably 26.5 or less, particularly preferably 26 or less, and the most preferably 25 or less.

In one preferred embodiment, the water absorbent agent of the present invention preferably has an irregular pulverized shape in view of the nature to be fixed to a hydrophilic fiber such as pulp or the like. An irregular pulverized shape indicates a pulverized product, preferably a pulverized product in aqueous solution polymerization.

In one preferred embodiment, the surface tension is 65 [mN/m] or greater, and more preferably 67 [mN/m] or greater, particularly preferably 70 [mN/m] or greater, and most preferably 72 [mN/m] or greater, with no substantial decrease in surface tension. The upper limit is generally sufficient at 75 [mN/m].

In one preferred embodiment, the neutralization rate is uniform. Although not wishing to be bound by any theory, this is because the water absorbent resin of the present invention is not neutralized after polymerizing an acrylic acid, but is obtained by polymerizing a salt of acrylic acid (e.g., sodium acrylate).

In one aspect, the present invention provides a sanitation article comprising the absorbent core. Although not wishing to be bound by any theory, this is because the sanitation article has diminished discomfort felt by a user even after a water absorbent agent absorbs urine, and a sanitation product with the same appearance as that at the time of the manufacture can be used even after long-term storage of the sanitation article.

(6-5) Preferred Properties of Composition and Agent of the Present Invention

In one aspect, a composition for reducing a molecular weight of a soluble component of a water absorbent agent, comprising an α-hydroxycarboxylic acid (salt) is provided.

In another aspect of the present invention, an agent, a polymerization regulator, a viscosity modifier, or a performance enhancer for reducing the molecular weight of a soluble component of a water absorbent agent, comprising an α-hydroxycarboxylic acid (salt) is provided.

An agent, a polymerization regulator, a viscosity modifier, and a performance enhancer having a function of reducing the molecular weight of a soluble component of a water absorbent agent similar to that of the composition of the present invention and a respective additional unique function are also encompassed by the present invention. Although not wishing to be bound by any theory, this is because the molecular weight of a soluble component of a water absorbent agent can be reduced by providing a composition or the like comprising an α-hydroxycarboxylic acid (salt), resulting in reduction in stickiness that leads to discomfort upon actual use of a sanitation product. The composition, the agent, the polymerization regulator, the viscosity modifier, and the performance enhancer of the present invention are also collectively referred to as "composition or the like".

In one aspect of the present invention, a composition or the like for reducing stickiness of a water absorbent agent after absorbing a liquid, comprising an α-hydroxycarboxylic acid (salt) is provided.

In yet another aspect of the present invention, a composition or the like for reducing a viscosity of a soluble component of a water absorbent agent upon swelling from absorbing a liquid, comprising an α-hydroxycarboxylic acid (salt) is provided.

In one preferred embodiment, the water absorbent resin described in (1-3) is used as water absorbent resin that is the main component of the water absorbent agent in the composition or the like. Further, the water absorbent agent in the composition or the like encompasses the water absorbent agent with the feature described in the method described in (6-1).

In one preferred embodiment, the α-hydroxycarboxylic acid (salt) in the composition or the like uses that described in (6-1).

(6-6) Most Preferred Properties of the Composition and Agent of the Present Invention In one aspect of the present invention, a composition for improving strong urine resistance of a water absorbent agent, comprising an α-hydroxycarboxylic acid (salt) and a chelating agent is provided.

In one aspect of the present invention, a composition for improving resistance to coloration over time of a water absorbent agent, comprising an α-hydroxycarboxylic acid (salt) and a chelating agent is provided.

In one aspect of the present invention, a composition for improving strong urine resistance and resistance to coloration over time of a water absorbent agent, comprising an α-hydroxycarboxylic acid (salt) and a chelating agent is provided.

The present invention can also encompass an agent, performance enhancer, and the like having a function of improving strong urine resistance and/or resistance to coloration over time similar to that of the composition of the present invention and a respective additional unique function. Although not wishing to be bound by any theory, this is because strong urine resistance and/or resistance to coloration over time of a water absorbent agent can be improved by providing a composition, agent, performance enhancer, or the like comprising an α-hydroxycarboxylic acid (salt) and a chelating agent, resulting in reduction in discomfort after absorbing urine or the like in actual use of a sanitation product, and a sanitation product with the same appearance as that at the time of the manufacture can be used even after long-term storage of the sanitation product.

The water absorbent agent in the composition or the like encompasses a water absorbent agent with the features described in the method described in (6-2) and the water absorbent agent in (6-4). The α-hydroxycarboxylic acid (salt) and the chelating agent in the composition encompass the α-hydroxycarboxylic acid (salt) and the chelating agent used in the method described in (6-2) and the water absorbent agent in (6-4), respectively.

(6-7) Use for Reducing the Molecular Weight of Soluble Component of the Water Absorbent Agent of the Present Invention In one aspect of the present invention, use of an α-hydroxycarboxylic acid (salt) for reducing a molecular weight of a soluble component of a water absorbent agent is provided.

In another aspect of the present invention, use of an α-hydroxycarboxylic acid (salt) for reducing stickiness of a water absorbent agent after absorbing a liquid is provided.

In yet another aspect of the present invention, use of an α-hydroxycarboxylic acid (salt) for reducing a viscosity of a soluble component of a water absorbent agent upon swelling from absorbing a liquid is provided.

In one preferred embodiment, the water absorbent resin described in (1-3) is used as the water absorbent resin that is the main component of the water absorbent agent in the composition or the like.

In one preferred embodiment, an α-hydroxycarboxylic acid (salt) described in (6-1) is used as the α-hydroxycarboxylic acid (salt) in the composition or the like.

(6-8) Use for Improving Strong Urine Resistance and/or Resistance to Coloration Over Time of the Water Absorbent Agent of the Present Invention In one aspect of the present invention, use of an α-hydroxycarboxylic acid (salt) and a chelating agent for improving strong urine resistance of a water absorbent agent is provided.

In one aspect of the present invention, use of an α-hydroxycarboxylic acid (salt) and a chelating agent for improving resistance to coloration over time of a water absorbent agent is provided.

In one aspect of the present invention, use of an α-hydroxycarboxylic acid (salt) and a chelating agent for improving strong urine resistance and resistance to coloration over time of a water absorbent agent is provided.

Although not wishing to be bound by any theory, this is because combined use of an α-hydroxycarboxylic acid (salt) and a chelating agent has better resistance to coloration over time than adding only one of the two and solves the problem of worsening urine resistance.

The water absorbent agent in the use encompasses a water absorbent agent having the feature described in the method described in (6-2) and the water absorbent agent in (6-4). The α-hydroxycarboxylic acid (salt) and the chelating agent in the use encompass the α-hydroxycarboxylic acid (salt) and the chelating agent used in the method described in (6-2) and the water absorbent agent in (6-4), respectively.

(6-9) Method of Reducing Molecular Weight of Soluble Component of the Water Absorbent Agent of the Present Invention In one aspect of the present invention, a method of reducing a molecular weight of a soluble component of a water absorbent agent, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying is provided.

In another aspect of the present invention, a method of reducing stickiness of a water absorbent agent after absorbing a liquid, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying is provided.

In yet another aspect of the present invention, a method of reducing a viscosity of a soluble component of a water absorbent agent upon swelling after absorbing a liquid, the method comprising a step of manufacturing the water absorbent agent with a centrifuge retention capacity (CRC) of 30 g/g or greater by polymerizing an aqueous monomer solution comprising an acrylic acid (salt) that can form a water absorbent agent by polymerization, drying hydrogel obtained by polymerizing, and surface crosslinking water absorbent resin powder obtained by drying, wherein the method comprises a step of adding an α-hydroxycarboxylic acid (salt) before the drying is provided.

The water absorbent agent in the method encompasses water absorbent agents with the feature described in the method described in (6-1).

In one preferred embodiment, the α-hydroxycarboxylic acid (salt) described in (6-1) is used as the α-hydroxycarboxylic acid (salt) in the composition or the like.

(6-10) Method for Improving Strong Urine Resistance and/or Resistance to Coloration Over Time of the Water Absorbent Agent of the Present Invention In one aspect of the present invention, a method for improving strong urine resistance of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less; and a YI value after a coloration promotion test of 26 or less is provided, In one aspect of the present invention, a method of improving resistance to coloration over time of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component extracted after adding 1 g of the water absorbent agent to 25 ml of degradation solution comprised of physiological saline (aqueous 0.94 sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less: and a YI value after a coloration promotion test of 26 or less is provided.

In one aspect of the present invention, a method of improving strong urine resistance and resistance to coloration over time of a water absorbent agent, the method comprising a step of manufacturing the water absorbent agent by polymerizing an aqueous monomer solution comprising an acrylic acid (salt) that can form a water absorbent agent by polymerization in the presence of an α-hydroxycarboxylic acid (salt), drying hydrogel obtained by polymerizing, and surface crosslinking water absorbent resin powder obtained by drying, the method comprising a step of adding a chelating agent after the polymerizing, wherein the water absorbent agent has features of: a Fe/L-as degradable soluble component extracted after adding 1 g of the water absorbent agent to 25 ml of degradation solution comprised of physiological saline (aqueous 0.9% sodium chloride solution) comprising 200 ppm of L-ascorbic acid and 0.4 ppm of divalent iron ion and leaving the solution standing for 16 hours at 37° C., and then adding physiological saline so that a total amount of the solution is 200 g and stirring the solution for 10 minutes, of 35% by weight or less; and a YI value after a coloration promotion test of 26 or less is provided.

Although not wishing to be bound by any theory, this is because an addition of an α-hydroxycarboxylic acid (salt) in a polymerization step in the above method and an addition of a chelating agent in a post-polymerization step improves resistance to coloration over time more than when adding only one of the two and further improves the negative impact to urine resistance.

The water absorbent agent in the method encompasses water absorbent agents having the feature described in the method described in (6-2) and the water absorbent agent in (6-4). The α-hydroxycarboxylic acid (salt) and the chelating agent in the method encompass the α-hydroxycarboxylic acid (salt) and the chelating agent used in the method described in (6-2) and the water absorbent agent in (6-4), respectively.

Reference literatures such as scientific literatures, patents, and patent applications cited herein are incorporated herein by reference to the same extent that the entirety of each document is specifically described.

The present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments and Examples that are specifically described herein and is limited only by the scope of claims.

EXAMPLES

The present invention is explained in more detail with the following Examples/Comparative Examples, but the interpretation of the present invention is not limited thereto. In addition, Examples obtained by appropriately combining the technical means disclosed in each Example are encompassed within the scope of the present invention.

The electronic equipment used in the Examples and comparative Examples (including physical measurements of a water absorbent resin) used a 200 V or 100 V power source, unless specifically noted otherwise. Various physical properties of the water absorbent agent of the invention were measured under the conditions with a room temperature (20 to 25° C.) and relative humidity of 50% RH, unless specifically noted otherwise.

Further, "liter" may be denoted as "l" or "L", and "% by weight" as "wt %" where convenient. Furthermore, the detection limit or lower, upon measurement of a trace amount of a component, is denoted as "N. D" (Not Detected).

[Measurement of Physical Properties of Water Absorbent Agent]

(a) Centrifuge Retention Capacity (CRC)

Centrifuge retention capacity (CRC) of the water absorbent agent of the present invention, i.e., absorption against no pressure, was measured in accordance with EDANA (ERT441.2-02). Specifically, CRC was obtained as the fluid retention capacity (unit; g/g) after placing 0.2 g of water absorbent resin in a non-woven fabric bag and then immersing the water absorbent resin in an overexcessive amount of aqueous 0.9% by weight sodium chloride solution for 30 minutes to allow the resin to freely swell, and then draining with a centrifuge (250 G).

(b) Amount of Water Soluble Polymer and Soluble Component Ratio

Hereinafter, the amount of water soluble polymer may be abbreviated as "amount of water-soluble component" or "amount of soluble component". A water soluble polymer is also referred to as "water-soluble component" or "soluble component". A "soluble component ratio" is the ratio (% by weight) of soluble component in a water absorbent agent. "Soluble component ratio" may also be denoted, with % by weight as the unit, as "Ext", "water-soluble component", "soluble component", "amount of water-soluble component" or "amount of soluble component".

184.3 g of aqueous 0.90% by mass aqueous sodium chloride solution was measured out and placed in a plastic container with a lid having a 250 ml capacity. 1.00 g of water absorbing polymer was added to the aqueous solution and the solution was stirred for 16 hours to extract a soluble component in the resin. 50.0 g of filtrate obtained by filtering the extract using one sheet of filter paper (ADVANTEC Toyo Kaisha, Ltd., product name: (JIS P 3801, No. 2), thickness 0.26 mm, retained particle size 5 μm) was measured out as a measured solution.

First, titration was performed on only 184.3 g of physiological saline (aqueous 0.90% by mass sodium chloride solution) with 0.1 N of aqueous NaOH solution up to pH of 10, and then with 0.1 N of aqueous HCl solution up to pH of 2.7 to obtain a blank titration amount ([bNaOH]ml, [bHCl]ml). The same titration operation was performed for the measured solution to find the titration amount ([NaOH] ml, [HCl]ml). For example, for a particulate water absorbent agent consisting of a known amount of acrylic acid and a salt thereof, the soluble component ratio in a water absorbing polymer can be calculated by the following formula (4) based on the average molecular weight of the monomer and the titration amount obtained by the above operation. The main component of the extracted soluble component is an extracted water soluble polymer. If the average molecular weight of a monomer is unknown, the average molecular weight of a monomer can be calculated using the neutralization rate found by titration. The neutralization rate is calculated by the following formula (5).

$$\text{Soluble component ratio (\% by mass)} = 0.1 \times (\text{average molecular weight of monomer}) \times 184.3 \times 100 \times ([\text{HCl}] - [b\text{HCl}])/1000/1.0/50.0 \quad \text{Formula (4)}:$$

$$\text{Neutralization rate (mol \%)} = (1 - ([\text{NaOH}] - [b\text{NaOH}])/([\text{HCl}] - [b\text{HCl}])) \times 100 \quad \text{Formula (5)}:$$

When the soluble component ratio for high water content, e.g., hydrogel crosslinked polymer, is measured, the amount of solid component of a water absorbing polymer can be calculated from the water content, and the amount of a given hydrogel crosslinked polymer is used for measurement.

(c) Moisture Absorption Blocking Ratio

About 2 g of water absorbent resin powder/water absorbent agent was uniformly dispersed in an aluminum cup with a diameter of 52 mm, and then left standing for 1 hour in a thermos hydrostat adjusted to a temperature of 25° C. and a relative humidity of 90±5% RH (ESPEC CORP.; MODEL: SH-641).

The water absorbent resin powder/water absorbent agent in the aluminum cup was then carefully transferred onto a JIS standard sieve (The IIDA TESTING SIEVE/inner diameter 80 mm) with an opening of 2000 μm (8.6 mesh), and classified for 5 seconds under the conditions with a temperature of 20 to 25° C. and a relative humidity of 50% RH using a ro-tap sieve shaker (SIEVE FACTORY IIDA CO., LTD; ES-65 sieve shaker/number of rotations: 230 rpm, number of impacts, 130 rpm).

Next, the mass of the residual water absorbent resin powder/water absorbent agent on the JIS standard sieve (mass W7 [g]) and the water absorbent resin powder/water absorbent agent (mass W8 [g]) passing through the JIS sieve was measured to calculate the moisture absorption fluidity (moisture absorption blocking ratio) according to the following formula (6). A lower value of moisture absorption blocking ratio indicates better moisture absorption fluidity.

$$\text{Moisture absorption blocking ratio [\% by mass]} = (W7/(W7+W8)) \times 100 \quad \text{Formula (6)}:$$

(d) Intrinsic viscosity (IV) and weight average molecular weight (Mw) of water-soluble component of water absorbent agent <Weight Average Molecular Weight (Mw) of Water-Soluble Component>

(Sample Preparation)

The filtrate obtained in the measurement of water-soluble component ratio was used. When the sample concentration was high, a GPC solution was appropriately used for dilution so that the concentration of the polymer component was about 0.5 mg/mL. The resulting solution was diluted 4-fold with the solvent shown below and passed through a filter (GL Sciences Inc., GL Chromatodisc, water based 25A, pore diameter 0.2 μm). This solution was measured under the following measurement conditions.

(GPC Measuring Conditions)

Viscotech's TDA302® was used for the measurement. This is an apparatus comprised of size-exclusion chromatography, refractive index detector, light scatter detector, and a capillary viscometer.

The measurement apparatus and measurement conditions were the following.
Pump/autosampler: Viscotech GPCmax
Guard column: OHpak SB-G (Showa Denko K. K.)
Column: two OHpak SB-806MHQ (Showa Denko K. K.) connected in series were used
Detector: Viscotech TDA302 (system temperature maintained at 30° C.)
Solvent: 60 mM sodium dihydrogenphosphate dihydrate/20 mM disodium hydrogenphosphate 12 hydrate/sodium azide 400 ppm aqueous solution (pH 6.35 to 6.38)
Flow rate: 0.5 mL/min
Injection amount: 100 μl Pure water used in the measurement was pure water from which impurities were thoroughly removed. Further, measurement was conducted under a stable baseline of detection values by having sufficient amount of solvent flow in the apparatus. In particular, measurement was conducted without a noise peak in the light scatter detector.

The apparatus was calibrated using polyoxyethylene glycol (weight average molecular weight (Mw) 21966, molecular weight distribution (Mw/Mn=1.0), differential refractive index (dn/dc)=0.132, solvent refractive index 1.33) as a reference sample.

When the particulate water absorbent agent was obtained by polymerizing a monomer comprising acrylic acid and/or a salt thereof at 99 mol % or greater, measurement was performed with a differential refractive index (dn/dc) of a polymer subjected to analysis of 0.12 and solvent refractive index of 1.33. The measurement result chart was reviewed, and measurement was taken again when peaks of light scatter intensity results contained a large amount of noise.

Data for refractive index, light scatter intensity, and viscosity was collected and analyzed with Viscotek OmniSEC 4.6.20 software. The weight average molecular weight (Mw) and intrinsic viscosity (IV) were calculated with data obtained from a viscometer (DP), refractive index (RI) and light scatter intensity (7° angle) LALS.

(e) Soluble Component Molecular Weight Reduction Ratio (%)

The reduction ratio of the weight average molecular weight of a water-soluble component when an α-hydroxycarboxylic acid was added to the weight average molecular weight of a water-soluble component when an α-hydroxycarboxylic acid was not added was used as the soluble component molecular weight reduction ratio. The soluble component molecular weight reduction ratio (%) was found according to the following formula (7).

[Numeral 1]

$$\text{Soluble component molecular weight reduction ratio (\%)} = (1-(\text{weight average molecular weight of a water-soluble component when α-hydroxycarboxylic acid was added})/(\text{weight average molecular weight of a water-soluble component when α-hydroxycarboxylic acid was not added}))\times 100(\%) \quad \text{Formula (7):}$$

(f) Tactile Sensation Evaluation

A sheet was made in a web of 120 mm×400 mm using a batch air sheet-making apparatus with 40 g of wood pulverized pulp and 60 g of water absorbent agent on a wire screen of 400 mesh (opening of 38 μm) having water absorbing paper placed thereon. The basis weight was adjusted by the sheet-making time. Next, the web was pressed under pressure to obtain an absorbent core. A paper diaper model absorbent core was prepared from the absorbent core comprising a polyethylene sheet as a liquid impermeable back sheet and side gather and water absorbing paper as a liquid permeable top sheet.

120 mm×400 mm SUS mesh (opening of 850 μm) was placed on the paper diaper model absorbent core, and an acrylic plate comprising a cylinder with a diameter of 60 mm and a height of 8 cm was placed in the center, and a 20 kg weight was placed on top of the acrylic plate to uniformly apply the load on the entire model absorbent core. 0.9% physiological saline was introduced at the same amount as the centrifuge retention capacity of the water absorbent agent from the cylinder. After confirming that the entire amount of physiological saline was taken up by the model absorbent core, the model absorbent core was placed in Unipack (size L, 480 mm×340 mm, SEISANNIPPONSHA LTD.) and retained at 40° C. for 6 hours.

The model absorbent core was taken out to evaluate the tactile sensation by the following 5 levels when touching from the top sheet side. The evaluation results of 10 panelists were averaged as the tactile sensation evaluation result. The absorbent core on which the evaluation is based is a model absorbent core prepared using a water absorbent agent free of α-hydroxycarboxylic acid prepared to have the same CRC by the same method as the water absorbent agent comprising an α-hydroxycarboxylic acid subjected to evaluation.

<Tactile Sensation Evaluation>
5: Stickiness is felt significantly
4: Stickiness is felt somewhat
3: Standard
2: Stickiness is hardly felt
1: No stickiness (g) Measurement Method of α-Hydroxycarboxylic Acid Content in Water Absorbent Agent A method of quantifying an α-hydroxycarboxylic acid of a water absorbent agent is not particularly limited. For example, the content can be quantified by extracting a soluble component from the water absorbent agent and analyzing the solution using high performance liquid chromatography. Specifically, the content can be quantified by the following method.

(Extraction of Soluble Component)

The supernatant of a solution prepared by adding 1.0 g of water absorbent resin to 200 mL of aqueous 0.9% by weight sodium chloride solution and stirring the solution for 1 hour at 500 rpm was filtered using a syringe filter (GL Sciences Inc., water based <type A>, model number 25A, pore diameter 0.45 m) as an extraction solution.

(Quantitative Analysis by High Performance Liquid Chromatography)

For example, the following can be used as the configuration of high performance chromatography for quantifying α-hydroxycarboxylic acids.
Pump: L-7110 (Hitachi High-Tech Science Corporation), flow rate 1.0 mL/min
Autosampler: L-7200 (Hitachi High-Tech Science Corporation), Injection amount 50 μL
Column oven: L-7300 (Hitachi High-Tech Science Corporation), temperature setting 30° C.
Differential refraction detector: L-7490 (Hitachi High-Tech Science Corporation)
Column: Shim-pack SCR-101H (Shimadzu GLC Ltd.)
Guard column: Shim-pack SCR (H) (Shimadzu GLC Ltd.)
Mobile phase: aqueous 85% phosphoric acid solution First, the α-hydroxycarboxylic acid to be quantified is dissolved into an aqueous 0.9% by weight sodium chloride solution to prepare an α-hydroxycarboxylic acid solution of any concentration. The solution is analyzed using high performance liquid chromatography with the above configuration. Calibration curves are drawn from the relationship between the concentration of α-hydroxycarboxylic acid and resulting chromatogram peak area.

Subsequently, a solution extracted from water absorbent resin is analyzed with high performance liquid chromatography, and the amount of α-hydroxycarboxylic acid is calculated from the relationship between the resulting chromatogram peak area and calibration curves. However, the extraction efficiency from water absorbent resin is assumed as 90%.

The quantification results are described in the following Examples.

(h) Absorption Against Pressure (AAP)

The absorption against pressure (AAP) of the water absorbent resin of the present invention was measured in accordance with EDANA (ERT442.2-02).

(1) Evaluation of Coloration of Water Absorbent Agent (yellowness/YI value)

Evaluation of coloration of water absorbent agent used Nippon Denshoku Industries' spectrocolorimeter SZ-Σ80COLOR MEASURING SYSTEM. 5 g of water absorbent agent was loaded on the furnished sample stage (about 60% loaded on the furnished sample stage) under set conditions (reflection measurement/attached powder·paste sample stage (inner diameter 30 mm, height 12 mm/powder·paste standard round white plate No. 2/30φ projector pipe)), and the surface color (YI value (Yellow Index)) was measured with the above spectrocolorimeter under the conditions of room temperature (20 to 25° C.) and humidity of 50 RH %. WB (Hunter color) and object colors (L, a, b) in other scales can also be simultaneously measured by the same measurement method of the same apparatus. A large L/WB or small a/b indicates lower coloration closer to substantially white.

(Coloration Promotion Test)

Subsequently, 5 g of water absorbent agent was loaded onto the paste sample stage. The paste sample stage loaded with the water absorbent agent was exposed to a thermos hydrostat (ESPEC CORP., product name: Bench-Top Type Temperature (& Humidity) Chamber, MODEL: SH-641) adjusted to an atmosphere with a temperature of 70±1° C. and a relative humidity of 65±1% for 7 days. After exposure, the surface color (YI value (Yellow Index)) after the coloration promotion test was measured with the spectrocolorimeter. In the present application (e.g., Examples), this may be denoted as coloration over time YI.

(j) Amount of Fe/L-as Degradable Soluble Component

The amount of Fe/L-as degradable soluble component of the present invention is measured in accordance with the following method.

Specifically, a solution comprised of physiological saline (aqueous 0.9% sodium chloride solution) comprising 200 ppm of L-ascorbic acid and 0.4 ppm of divalent iron ion is prepared as a degradation test solution. As a specific example, 2 g of iron(II) sulfate heptahydrate is dissolved in 1000 g of physiological saline to prepare an aqueous solution comprising 400 ppm iron ions. 1 g of the aqueous solution comprising 400 ppm iron ions and 0.2 g of L-ascorbic acid are dissolved in physiological saline so that the total amount is 1000 g.

Next, 25 ml of the degradation test solution is placed in a polypropylene container with a lid having a capacity of 120 ml. 1 g of water absorbent agent is added thereto, and swellable gel is allowed to swell 25-fold. At this time, the lid of the container is closed and sealed and the swellable gel is left standing for 16 hours under the atmosphere of 37° C. A stirrer tip (length of 35 mm x outer diameter of 8 mm) is then introduced. The gel is stirred for 10 minutes to extract a Fe/L-as degradable soluble component. A measuring method that is the same as the method of measuring the amount of soluble component (in accordance with paragraphs [0134] to [0146] in Japanese Laid-Open Publication No. 2006-055833 or EDANA (ERT470.2-02) is performed thereafter to find the amount of Fe/L-as degradable soluble component (% by weight).

Since the amount of Fe/L-as degradable soluble component is affected by the water content, evaluation uses a value corrected for water content in the present invention.

(k) Measurement of Surface Tension 50 ml of physiological saline adjusted to 20° C. was placed in a thoroughly cleaned 100 ml beaker. First, the surface tension of physiological saline was measured using a tensiometer (KRUSS' K11 automatic tensiometer). In this measurement, the value of surface tension must be within the range of 71 to 75 [mN/m].

Next, a thoroughly washed 25 mm long fluorine resin rotor and 0.5 g of water absorbent agent were placed in the beaker comprising physiological saline adjusted to 20° C. after measuring the surface tension, and the content was stirred for 4 minutes under the condition of 500 rpm. After 4 minutes, stirring was discontinued. After precipitation of water containing water absorbent agent, the surface tension of the supernatant was measured again by the same operation. The present invention employed a plate method using a platinum plate. The plate was used after thoroughly washing with deionized water and heating and cleaning with a gas burner prior to each measurement.

Commercially available raw material compounds, reaction reagents and solvents were used (e.g., those sold by Nippon Shokubai) were used as the raw material compounds, reaction reagents and solvents used in the Examples and Comparative Examples, unless specifically noted otherwise.

Comparative Example 1

425.2 g of acrylic acid, 4499.5 g of aqueous 37% by mass sodium acrylate solution, 526.1 g of deionized water (ion exchange water), and 7.41 g (0.06 mol % relative to carboxyl group containing unsaturated monomer) of polyethylene glycol diacrylate (average molecular weight 523) were dissolved in a reactor, which consists of a double arm jacketed stainless steel kneader with two sigma blades having an internal capacity of 10 L and a lid, to prepare an aqueous monomer solution (a). This aqueous monomer solution (a) was then deaerated for 20 minutes under a nitrogen gas atmosphere.

When 14.16 g of aqueous 20% by mass sodium persulfate solution and 23.6 g of aqueous 0.1% by mass L-ascorbic acid solution were subsequently added, while stirring, to the aqueous monomer solution (a), polymerization was initiated after about 20 seconds. After 2 minutes from initiation of polymerization, 5.19 g of aqueous 1.0% by mass diethylenetriaminepentaacetic acid trisodium salt solution (diethylenetriaminepentaacetic acid trisodium salt corresponding to 0.01% by mass relative to carboxyl group containing unsaturated monomer) was added to the polymerization solution. While polymerization was in progress in the polymerization solution when the aqueous diethylenetriaminepentaacetic acid trisodium salt solution as added, there were many liquid substances. Polymerization was performed at 25° C. or higher and 90° C. or lower while grinding the generated gel. After 34 minutes from the initiation of polymerization, a crosslinked hydrogel polymer (1) (hereinafter, denoted as hydrogel) was retrieved. The resulting hydrogel was fragmented into particles with a diameter of about 5 mm or less.

The fragmented hydrogel-like polymer was spread on a mesh with a mesh size of 50 and dried with hot air for 45 minutes at 185° C., The dried product was pulverized using a roll mill (WML roll mill/Inokuchi Giken) and sorted using a JIS sieve with an opening of 850 µm, 600 µm, 500 µm, 300 µm, and 150 µm and compounded to obtain a comparative pulverized water absorbent resin (1) with an irregular pulverized shape having a mass average particle diameter (D50) of 349 µm and logarithmic standard deviation (σζ) of particle size distribution of 0.35. The centrifuge retention capacity (CRC) of the comparative water absorbent resin (1) was 31.8 (g/g).

A surface crosslinking agent solution consisting of 0.4 parts by weight of 1,4-butanediol, 0.6 parts by weight of propylene glycol, and 3.0 parts by weight of deionized water (ion exchange water) was added to and homogeneously mixed with 100 parts by weight of comparative water absorbent resin (1). The mixture was then heated for 40 minutes at 210° C. for surface crosslinking.

After the heating treatment, the mixture was crushed until the mixture passed through a JIS standard sieve with an opening of 850 µm to obtain comparative water absorbent resin particles (1).

An aqueous solution consisting of 0.03 parts by weight of diethylenetriaminepentaacetic acid trisodium (DTPA·3Na) and 1.0 part by weight of deionized water (ion exchange water) was added to and homogenously mixed with the resulting comparative water absorbent resin particles (1) for granulation. After heating for 45 minutes at 60° C. under windless conditions, the particles were crushed until they passed through a JIS standard sieve with an opening of 850 µm to obtain granulated comparative water absorbent resin particles (1).

0.3 parts by weight of silica (product name Reolosil QS-20, Tokuyama) was mixed with 100 parts by mass of the granulated comparative water absorbent resin particles (1). This was performed by placing 30 g of comparative water absorbent resin particles with silica in a mayonnaise jar with a capacity of 225 mL and shaking the jar with a paint shaker (Toyo Seiki) for 3 minute to obtain comparative water absorbent agent (1). The CRC, molecular weight of soluble component, and intrinsic viscosity of soluble component of the resulting comparative water absorbent agent (1) are shown in Table 1.

Comparative Example 2

The same treatment was applied as Comparative Example 1, except for the amount of polyethylene glycol diacrylate used being 0.093 mol % relative to the carboxyl group containing unsaturated monomer and simultaneously adding 10.75 g (malic acid was 0.165 mol % relative to carboxyl group containing unsaturated monomer) of aqueous 50% malic acid solution (DL-malic acid, 50% by weight aqueous solution, Fuso Chemical Co., Ltd., Food additive grade) when adding an aqueous diethylenetriaminepentaacetic acid trisodium salt solution during polymerization in Comparative Example 1, to obtain comparative water absorbent agent (2). The CRC, molecular weight of soluble component, and intrinsic viscosity of soluble component of the comparative water absorbent agent (2) are shown in Table 1. The soluble component molecular weight reduction ratio (%) and results of tactile sensation evaluation of the comparative water absorbent agents (1) and (2) are shown in Table 2.

Comparative Example 3

An aqueous monomer solution (b') was prepared by introducing and mixing 441.62 g of acrylic acid, 1.763 g (0.055 mol % relative to carboxyl group containing unsaturated monomer) of polyethylene glycol diacrylate (molecular weight 523) as an internal crosslinking agent, 2.70 g (0.005% by weight relative to carboxyl group containing unsaturated monomer) of aqueous 1.0% by weight diethylenetriaminepentaacetic acid trisodium (DTPA·3Na) solution, 181.96 g of aqueous 48.5% by weight sodium hydroxide solution, and 363.9 g of deionized water (ion exchange water) in a polypropylene container with a capacity of 2 liters.

Next, the aqueous monomer solution (b') was cooled while stirring. When the solution temperature reached 39.5° C., 187.01 g of aqueous 48.5% by weight sodium hydroxide solution adjusted to 40° C. was added and mixed to prepare an aqueous monomer solution (b). The temperature of the aqueous monomer solution (b) at this time rose to 76.9° C. due to the second stage of heat of neutralization immediately after the preparation. Deposits were observed immediately after starting to mix the aqueous 48.5% by weight sodium hydroxide solution, but the deposits gradually dissolved to yield a transparent and homogeneous solution.

Next, after adding 21.01 g of aqueous 3.5% by weight sodium persulfate solution to the aqueous monomer solution (b) being stirred, the mixture was immediately poured into a stainless steel vat (bottom surface 340×340 mm, height 25 mm, inner surface: Teflon(registered trademark) coating) in an open air system. The time from the start of second stage of neutralization until pouring the aqueous monomer solution (b) into the vat was 55 seconds. The vat was heated until the surface temperature was 40° C. using a hot plate (NEO HOTPLATE HI-1000/Iuchi Seieido).

The polymerization reaction started 60 seconds after the aqueous monomer solution (b) was poured into the vat. The polymerization reaction progressed, swelling and bubbling in all directions while generating water vapor. The solution then contracted to a size that was slightly larger than the vat. The crosslinked hydrogel polymer (hereinafter, referred to as "hydrogel") (3) was retrieved after 3 minutes from the start of the polymerization reaction. The series of operations were performed in an open air system.

The hydrogel (3) obtained in the polymerization reaction was ground using a meat chopper (HL-3225N, plate pour diameter: 10.0 mm/Remacom) to prepare particular hydrogel (3).

The amount of the hydrogel (3) supplied was 360 g/min. Gel was ground while adding deionized water adjusted to 90° C. at 50 g/min, simultaneously with supplying the hydrogel (3).

The fragmented hydrogel (3) was spread on a mesh with a mesh size of 50 and dried with hot air for 30 minutes at 190° C. The dried product was pulverized using a roll mill (WML roll mill/Inokuchi Giken) and sorted using a JIS sieve with an opening of 850 µm, 600 µm, 500 µm, 300 µm, and 150 µm and compounded to obtain a comparative ground water absorbent resin (3) with an irregular pulverized shape having a mass average particle diameter (D50) of 349 µm and logarithmic standard deviation ($\sigma\zeta$) of particle size distribution of 0.35. The centrifuge retention capacity (CRC) of the comparative water absorbent resin (3) was 38.6 (g/g).

A surface crosslinking agent solution consisting of 0.27 parts by weight of ethylene carbonate, 0.45 parts by weight of propylene glycol, and 1.8 parts by weight of deionized water (ion exchange water) was added to and homogeneously mixed with 100 parts by weight of comparative water absorbent resin (3). The mixture was then heated for 40 minutes at 200° C. for surface crosslinking.

After the heating treatment, the mixture was crushed until it passed through the JIS standard sieve with an opening of 850 µm to obtain comparative water absorbent resin particles (3).

An aqueous solution consisting of 0.03 parts by weight of diethylenetriaminepentaacetic acid trisodium (DTPA·3Na) and 1.0 part by weight of deionized water (ion exchange water) was added to and homogenously mixed with the resulting comparative water absorbent resin particles (3) for granulation. After heating for 45 minutes at 60° C. under windless conditions, the particles were crushed until they passed through a JIS standard sieve with an opening of 850 µm to obtain granulated comparative water absorbent resin particles (3).

0.3 parts by weight of silica (product name Reolosil QS-20, Tokuyama) was mixed with 100 parts by mass of the granulated comparative water absorbent resin particles (3). This was performed by placing 30 g of comparative water absorbent resin particles with silica in a mayonnaise jar with a capacity of 225 mL and shaking the jar with a paint shaker (Toyo Seiki) for 3 minute to obtain comparative water absorbent agent (3). The CRC, molecular weight of soluble component, and intrinsic viscosity of soluble component of the comparative water absorbent agent (3) are shown in Table 1.

Example 1

The same treatment was applied as Comparative Example 3, except for the amount of polyethylene glycol diacrylate used being 2.404 g (0.075 mol % relative to carboxyl group containing unsaturated monomer) and adding 10.8 g (malic acid was 0.658 mol % relative to carboxyl group containing unsaturated monomer) of aqueous 50% malic acid solution (DL-malic acid, 50% by weight aqueous solution, Fuso Chemical Co., Ltd., Food additive grade) to the aqueous monomer solution (b') in Comparative Example 3, to obtain water absorbent agent (1). The CRC, molecular weight of soluble component, and intrinsic viscosity of soluble component of the water absorbent agent (1) are shown in Table 1. Further, the moisture absorption blocking ratio of the water absorbent agent (1) was 0%.

Example 2

The same treatment was applied as Comparative Example 3, except for the amount of polyethylene glycol diacrylate used being 2.244 g (0.070 mol % relative to carboxyl group containing unsaturated monomer) and adding 5.4 g (sodium lactate was 0.394 mol % relative to carboxyl group containing unsaturated monomer) of aqueous 50% sodium lactate solution (sodium lactate, Purac) to the aqueous monomer solution (b') in Comparative Example 3, to obtain water absorbent agent (2). The CRC, molecular weight of soluble component, and intrinsic viscosity of soluble component of the water absorbent agent (2) are shown in Table 1.

Example 3

The same treatment was applied as Example 1, except for the amount of polyethylene glycol diacrylate used being 2.18 g (0.068 mol % relative to carboxyl group containing unsaturated monomer), the amount of malic acid used being 0.329 mol % relative to carboxyl group containing unsaturated monomer, and changing silica to hydrotalcite (product name DHT-6, Kyowa Chemical Industry Co., Ltd.) in Example 1, to obtain water absorbent agent (3). The CRC, molecular weight of soluble component, and intrinsic viscosity of soluble component of the water absorbent agent (3) are shown in Table 1. The soluble component molecular weight reduction rate and tactile sensation evaluation results of comparative water absorbent agent (3) and water absorbent agents (1), (2), and (3) are shown in Table 3.

Comparative Example 4

The same treatment was applied as Comparative Example 3, except for the amount of polyethylene glycol diacrylate used being 1.122 g (0.035 mol % relative to carboxyl group containing unsaturated monomer) and the surface crosslinking agent solution being 0.024 part by weight of diethylene glycol diglycidyl ether (product name: Denacol EX-810, Nagase ChemteX Corporation), 0.31 parts by weight of ethylene carbonate, 0.52 parts by weight of propylene glycol, and 2.08 parts by weight of deionized water (ion exchange water), and changing the heating temperature to 195° C. in Comparative Example 3, to obtain comparative water absorbent agent (4). The CRC, molecular weight of soluble component, and intrinsic viscosity of soluble component of the comparative water absorbent agent (4) are shown in Table 1.

Example 4

The same treatment was applied as Comparative Example 4, except for the amount of polyethylene glycol diacrylate used being 1.506 g (0.047 mol % relative to carboxyl group containing unsaturated monomer) and adding 5.4 g (malic acid was 0.329 mol % relative to carboxyl group containing unsaturated monomer) of aqueous 50% malic acid solution (DL-malic acid, 50% by weight aqueous solution, Fuso Chemical Co., Ltd., Food additive grade) to the aqueous monomer solution (b') in Comparative Example 4, to obtain water absorbent agent (4). The CRC, molecular weight of soluble component, and intrinsic viscosity of soluble component of the water absorbent agent (4) are shown in Table 1.

Example 5

The same treatment was applied as Comparative Example 4, except for the amount of polyethylene glycol diacrylate used being 1.442 g (0.045 mol % relative to carboxyl group containing unsaturated monomer) and adding 4.32 g (sodium lactate was 0.315 mol % relative to carboxyl group containing unsaturated monomer) of aqueous 50% sodium lactate solution (sodium lactate, Purac) to the aqueous monomer solution (b') in Comparative Example 4, to obtain water absorbent agent (5). The CRC, molecular weight of soluble component, and intrinsic viscosity of soluble component of the water absorbent agent (5) are shown in Table 1.

Example 6

The same treatment was applied as Comparative Example 4, except for the amount of polyethylene glycol diacrylate used being 1.442 g (0.045 mol % relative to carboxyl group containing unsaturated monomer) and changing the deionized water supplied upon gel grinding to an aqueous 4.32% sodium lactate solution (50% sodium lactate, Purac, was used by adjusting the concentration with ion exchange water) (sodium lactate was 0.473 mol % relative to carboxyl group containing unsaturated monomer) in Comparative Example 4, to obtain water absorbent agent (6). The CRC, molecular weight of soluble component, and intrinsic viscosity of soluble component of the water absorbent agent (6) are shown in Table 1.

Example 7

The same treatment was applied as Example 4, except for the amount of polyethylene glycol diaorylate used being 1.442 g (0.045 mol % relative to carboxyl group containing unsaturated monomer) and changing the silica to tricalcium phosphate (Wako Pure Chemical Industries, Ltd., CAS No. 7758-87-4) in Example 4, to obtain water absorbent agent (7). The CRC, molecular weight of soluble component, and intrinsic viscosity of soluble component of the water absorbent agent (7) are shown in Table 1. The soluble component molecular weight reduction rate and tactile sensation evaluation results of comparative water absorbent agent (4) and water absorbent agents (4) to (7) are shown in Table 4.

Comparative Example 5

The same treatment was applied as Comparative Example 3, except for the amount of polyethylene glycol diacrylate used being 0.801 g (0.025 mol % relative to carboxyl group containing unsaturated monomer) and the surface crosslinking agent solution being 0.017 part by weight of diethylene glycol diglycidyl ether (product name: Denacol EX-810, Nagase ChemteX Corporation), 0.22 parts by weight of ethylene carbonate, 0.36 parts by weight of propylene glycol, and 1.46 parts by weight of deionized water (ion exchange water), and changing the heating temperature to 190° C. in Comparative Example 3, to obtain comparative water absorbent agent (5). The CRC, molecular weight of soluble component, and intrinsic viscosity of soluble component of the comparative water absorbent agent (5) are shown in Table 1.

Example 8

The same treatment was applied as Comparative Example 5, except for the amount of polyethylene glycol diacrylate used being 1.026 g (0.032 mol % relative to carboxyl group containing unsaturated monomer) and adding 2.70 g (malic acid was 0.165 mol % relative to carboxyl group containing unsaturated monomer) of aqueous 50% malic acid solution (DL-malio acid, 50% by weight aqueous solution, Fuso Chemical Co., Ltd., Food additive grade) to the aqueous monomer solution (b') in Comparative Example 5, to obtain water absorbent agent (8). The CRC, molecular weight of soluble component, and intrinsic viscosity of soluble component of the water absorbent agent (8) are shown in Table 1.

Example 9

The same treatment was applied as Comparative Example 5, except for the amount of polyethylene glycol diacrylate used being 1.058 g (0.033 mol % relative to carboxyl group containing unsaturated monomer) and changing the deionized water supplied upon gel grinding to aqueous 3.60% malic acid solution (DL-malic acid, 50% by weight aqueous solution, Fuso Chemical Co., Ltd., Food additive grade, was used by adjusting the concentration with ion exchange water) (malic acid was 0.329 mol % relative to carboxyl group containing unsaturated monomer) in Comparative Example 5, to obtain water absorbent agent (9). The CRC, molecular weight of soluble component, and intrinsic viscosity of soluble component of the water absorbent agent (9) are shown in Table 1. The soluble component molecular weight reduction rate and tactile sensation evaluation results of comparative water absorbent agent (5), water absorbent agent (8), and water absorbent agent (9) are shown in Table 5.

Comparative Example 6

436.4 g of acrylic acid, 4617.9 g of aqueous 37% by mass sodium acrylate solution, 402.5 g of deionized water (ion exchange water), and 4.43 g (0.035 mol % relative to carboxyl group containing unsaturated monomer) of polyethylene glycol diacrylate (average molecular weight 523) were dissolved in a reactor, which consists of a double arm jacketed stainless steel kneader with two sigma blades having an internal capacity of 10 L and a lid, to prepare an aqueous monomer solution (c). This aqueous monomer solution (c) was then deaerated for 20 minutes under a nitrogen gas atmosphere.

When 14.53 g of aqueous 20% by mass sodium persulfate solution and 24.22 g of aqueous 0.1% by mass L-ascorbic acid solution were subsequently added, while stirring, to the aqueous monomer solution (c), polymerization was initiated after about 20 seconds. Polymerization was performed at 25° C. or higher and 90° C. or lower while grinding the generated gel. After 30 minutes from the initiation of polymerization, a crosslinked hydrogel polymer (6) (hereinafter, denoted as hydrogel) was retrieved. The resulting hydrogel (6) was fragmented into particles with a diameter of about 5 mm or less.

The fragmented hydrogel-like polymer (6) was spread on a mesh with a mesh size of 50 and dried with hot air for 45 minutes at 185° C. The dried product was pulverized using a roll mill (WML roll mill/Inokuchi Giken) and sorted using a JIS sieve with an opening of 850 μm, 600 μm, 500 μm, 300 μm, and 150 μm and compounded to obtain a comparative pulverized water absorbent resin (6) with an irregular pulverized shape having a mass average particle diameter (D50) of 349 μm and logarithmic standard deviation (σζ) of particle size distribution of 0.35. The centrifuge retention capacity (CRC) of the comparative water absorbent resin (6) was 46.6 (g/g).

A surface crosslinking agent solution consisting of 0.024 part by weight of diethylene glycol diglycidyl ether (product name: Denacol EX-810, Nagase ChemteX Corporation), 0.31 parts by weight of ethylene carbonate, 0.52 parts by weight of propylene glycol, and 2.08 parts by weight of deionized water (ion exchange water) was added to and homogeneously mixed with 100 part by weight of comparative water absorbent resin (6). The mixture was then heated for 40 minutes at 195° C. for surface crosslinking.

After the heating treatment, the mixture was crushed until it passed through the JIS standard sieve with an opening of 850 μm to obtain comparative water absorbent resin particles (6).

An aqueous solution consisting of 0.03 parts by weight of diethylenetriaminepentaacetic acid trisodium (DTPA·3Na) and 1.0 part by weight of deionized water (ion exchange water) was added to and homogenously mixed the resulting comparative water absorbent resin particles (6) for granulation. After heating for 45 minutes at 60° C. under windless conditions, the particles were crushed until they passed through a JIS standard sieve with an opening of 850 μm to obtain granulated comparative water absorbent resin particles (6).

0.3 parts by weight of silica (product name Reolosil QS-20, Tokuyama) was mixed with 100 parts by mass of the granulated comparative water absorbent resin particles (6). This was performed by placing 30 g of comparative water absorbent resin particles with silica in a mayonnaise jar with a capacity of 225 mL and shaking the jar with a paint shaker (Toyo Seiki) for 3 minute to obtain comparative water absorbent agent (6). The CRC, molecular weight of soluble component, and intrinsic viscosity of soluble component of the comparative water absorbent agent (6) are shown in Table 1.

Example 10

The same treatment was applied as Comparative Example 6, except for the amount of polyethylene glycol diacrylate used being 5.19 g (0.041 mol % relative to carboxyl group containing unsaturated monomer) and adding 10.59 g (malic acid was 0.165 mol % relative to carboxyl group containing unsaturated monomer) of aqueous 50% malic acid solution (DL-malic acid, 50% by weight aqueous solution, Fuso Chemical Co., Ltd., Food additive grade) after 2 minutes from initiation of polymerization in Comparative Example 6, to obtain water absorbent agent (10). The CRC, molecular weight of soluble component, and intrinsic viscosity of soluble component of the water absorbent agent (10) are shown in Table 1.

Example 11

In Comparative Example 6, 5.07 g (0.04 mol % relative to carboxyl group containing unsaturated monomer) of polyethylene glycol diacrylate was used. After 20 minutes from the initiation of polymerization, hydrogel (6) was retrieved from the polymerizer. The resulting hydrogel (6) was ground using a meat chopper (HL-3225N, plate pour diameter: 12.0 mm/Remacom) to prepare particular hydrogel. The amount of the hydrogel (6) supplied was 360 g/min. Gel was grinding while adding an aqueous 3.6% malic acid solution (DL-malic acid, 50% by weight aqueous solution, Fuso Chemical Co., Ltd., Food additive grade, was used by adjusting the concentration with ion exchange water) at 50 g/min, simultaneously with supplying the hydrogel (6), to obtain hydrogel particle. Other than the above, the same treatment was applied as Comparative Example 6 to obtain absorbent (11). The CRC, molecular weight of soluble component, and intrinsic viscosity of soluble component of the water absorbent agent (11) are shown in Table 1. The soluble component molecular weight reduction rate and tactile sensation evaluation results of comparative water absorbent agent 6, water absorbent agent 10, and water absorbent agent 11 are shown in Table 6.

Comparative Example 7

The same treatment was applied as Comparative Example 6, except for the amount of polyethylene glycol diacrylate used being 2.53 g (0.020 mol % relative to carboxyl group containing unsaturated monomer) in Comparative Example 6, to obtain comparative water absorbent agent (7). The CRC, molecular weight of soluble component, and intrinsic viscosity of soluble component of the comparative water absorbent agent (7) are shown in Table 1.

Example 12

The same treatment was applied as Comparative Example 7, except for the amount of polyethylene glycol diacrylate used being 3.17 g (0.025 mol % relative to carboxyl group containing unsaturated monomer) and adding 6.46 g (sodium lactate was 0.119 mol % relative to carboxyl group containing unsaturated monomer) of aqueous 50% sodium lactate solution (sodium lactate, Purac) after 2 minutes from the initiation of polymerization in Comparative Example 7, to obtain water absorbent agent (12). The CRC, molecular weight of soluble component, and intrinsic viscosity of soluble component of the water absorbent agent (12) are shown in Table 1. The soluble component molecular weight reduction rate and tactile sensation evaluation results of comparative water absorbent agent 7 and water absorbent agent (12) are shown in Table 7.

Comparative Example 8

An aqueous monomer solution (d') was prepared by introducing and mixing 174.57 g of acrylic acid, 1847.12 g of aqueous 37% by mass sodium acrylate solution, 2.38 g (0.047 mol % relative to carboxyl group containing unsaturated monomer) of polyethylene glycol diacrylate (molecular weight 523) as an internal crosslinking agent, and 170.02 g of deionized water (ion exchange water) in a polypropylene container with a capacity of 3 liters.

Next, the aqueous monomer solution (d') was supplied and mixed in a reaction vessel consisting of a lid comprising a thermometer, nitrogen gas introducing tube, and a ventilation bore and a vat with a 300 mm×220 mm bottom surface and a depth of 60 mm, and comprising a black light fluorescence lamp on the top. The aqueous monomer solution (d') was immersed in a 40° C. water bath to the height of 10 mm from the bottom. Nitrogen gas was introduced to the aqueous solution and deaerated for 20 minutes. After confirming that the solution reached 40° C., 5.81 g of aqueous 20% by weight sodium persulfate solution and 0.1 g of diphenyl(2,4,6-trimethylbenzoyl)phosphinoxide were added under nitrogen gas flow atmosphere, simultaneously with light irradiation. The solution was stirred and mixed. The monomer concentration was 40% by weight. After initiation of polymerization, the polymerization system was not stirred but the reaction vessel continued to be immersed in the 40° C. water bath and cooled. A polymerization reaction was then performed for 20 minutes with the temperature of the water bath at 80° C. to obtain hydrogel.

The hydrogel (8) obtained in the polymerization reaction was ground using a meat chopper (HL-3225N, plate pour diameter: 10.0 mm/Remacom) to prepare particular hydrogel (8).

The amount of the hydrogel (8) supplied was 360 g/min. Gel was ground while adding deionized water adjusted to 90° C. at 50 g/min, simultaneously with supplying the hydrogel (8).

The gel was dried with hot air for 30 minutes at 190° C., and then pulverized using a roll mill (Inokuchi Giken) and sorted using a sieve with an opening of 850 μm, 600 μm, 500 μm, 300 μm, and 150 μm and compounded to obtain a comparative pulverized water absorbent resin (8) with an irregular pulverized shape having a mass average particle diameter (D50) of 349 μm and logarithmic standard deviation (σζ) of particle size distribution of 0.35. The centrifuge retention capacity (CRC) of the comparative water absorbent resin (8) was 48.0 (g/g).

A surface crosslinking agent solution consisting of 0.18 parts by weight of 1,3-propanediol, 4.0 parts by weight of methanol, and 3.2 parts by weight of deionized water (ion exchange water) was added to and homogeneously mixed with 100 parts by weight of comparative water absorbent resin (8). The mixture was then heated for 40 minutes at 190° C. for surface crosslinking.

After the heating treatment, the mixture was crushed until it passed through the JIS standard sieve with an opening of 850 μm to obtain comparative water absorbent resin particles (8).

An aqueous solution consisting of 0.03 parts by weight of diethylenetriaminepentaacetic acid trisodium (DTPA·3Na) and 1.0 part by weight of deionized water (ion exchange water) was added to and homogenously mixed with the resulting comparative water absorbent resin particles (8) for granulation. After heating for 45 minutes at 60° C. under windless conditions, the particles were crushed until they passed through a JIS standard sieve with an opening of 850 μm to obtain granulated comparative water absorbent resin particles (8).

0.3 parts by weight of silica (product name Reolosil QS-20, Tokuyama) was mixed with 100 parts by mass of the granulated comparative water absorbent resin particles (8). This was performed by placing 30 g of comparative water absorbent resin particles with silica in a mayonnaise jar with a capacity of 225 mL and shaking the jar with a paint shaker (Toyo Seiki) for 3 minute to obtain comparative water absorbent agent (8). The CRC, molecular weight of soluble component, and intrinsic viscosity of soluble component of the comparative water absorbent agent (8) are shown in Table 1.

Example 13

The same treatment was applied as Comparative Example 8, except for the amount of polyethylene glycol diacrylate used being 3.29 g (0.065 mol % relative to carboxyl group containing unsaturated monomer) and adding 8.58 g (malic acid was 0.329 mol % relative to carboxyl group containing unsaturated monomer) of aqueous 50% malic acid solution (DL-malic acid, 50% by weight aqueous solution, Fuso Chemical Co., Ltd., Food additive grade) to the aqueous monomer solution (d') in Comparative Example 8, to obtain water absorbent agent (13). The CRC, molecular weight of soluble component, and intrinsic viscosity of soluble component of the water absorbent agent (13) are shown in Table 1.

Example 14

The same treatment was applied as Comparative Example 8, except for the amount of polyethylene glycol diacrylate used being 3.29 g (0.065 mol % relative to carboxyl group containing unsaturated monomer) and changing the deionized water supplied upon gel grinding to aqueous 7.20% malic acid solution (DL-malic acid, 50% by weight aqueous solution, Fuso Chemical Co., Ltd., Food additive grade, was used by adjusting the concentration with ion exchange water) (malic acid was 0.658 mol % relative to carboxyl group containing unsaturated monomer) in Comparative Example 8, to obtain water absorbent agent (14). The CRC, molecular weight of soluble component, and intrinsic viscosity of soluble component of the water absorbent agent (14) are shown in Table 1. The soluble component molecular weight reduction rate and tactile sensation evaluation results of comparative water absorbent agent (8), water absorbent agent (13), and water absorbent agent (14) are shown in Table 8.

Comparative Example 9

The same treatment was applied as Comparative Example 8, except for the amount of polyethylene glycol diacrylate used being 4.05 g (0.08 mol % relative to carboxyl group containing unsaturated monomer) and changing 0.1 g of diphenyl(2,4,6-trimethylbenzoyl)phosphinoxide to 0.1 g of IRGACURE 819 in Comparative Example 8, to obtain comparative water absorbent agent (9). The CRC, molecular weight of soluble component, and intrinsic viscosity of soluble component of the comparative water absorbent agent (9) are shown in Table 1.

Example 15

The same treatment was applied as Comparative Example 8, except for the amount of polyethylene glycol diacrylate used being 5.07 g (0.1 mol % relative to carboxyl group containing unsaturated monomer) and adding 10.3 g (sodium lactate was 0.473 mol % relative to carboxyl group containing unsaturated monomer) of aqueous 50% sodium lactate solution (sodium lactate, Purac) to the aqueous monomer solution (d') in Comparative Example 9, to obtain water absorbent agent (15). The CRC, molecular weight of soluble component, and intrinsic viscosity of soluble component of the water absorbent agent (15) are shown in Table 1. The soluble component molecular weight reduction rate and tactile sensation evaluation results of comparative water absorbent agent (9) and water absorbent agent (15) are shown in Table 9.

Comparative Example 10

The same treatment was applied as Comparative Example 4, except for the amount of polyethylene glycol diacrylate used being 0.930 g (0.029 mol % relative to carboxyl group containing unsaturated monomer), the heating temperature being 180° C., and not adding diethylenetriaminepentaacetic acid trisodium to water absorbent resin particles upon granulation in Comparative Example 4, to obtain comparative water absorbent agent (10). The CRC, molecular weight of soluble component, and intrinsic viscosity of soluble component of the comparative water absorbent agent (10) are shown in Table 1.

Example 16

The same treatment was applied as Comparative Example 10, except for the amount of polyethylene glycol diacrylate used being 1.026 g (0.032 mol % relative to carboxyl group containing unsaturated monomer) and adding 1.08 g (malic acid was 0.066 mol % relative to carboxyl group containing unsaturated monomer) of aqueous 50% malic acid solution (DL-malic acid, 50% by weight aqueous solution, Fuso Chemical Co., Ltd., Food additive grade) to the aqueous monomer solution (b') in Comparative Example 10, to obtain water absorbent agent (16). The CRC, molecular weight of soluble component, and intrinsic viscosity of soluble component of water absorbent agent (16) are shown in Table 1. Further, the soluble component molecular weight reduction rate and tactile sensation evaluation results of comparative water absorbent agent (10) and water absorbent agent (16) are shown in Table 10. The YI value, Fe/L-as degradable soluble component, CRC and AAP of water absorbent agent (16) are shown in Table 14.

Example 17

The same treatment was applied as Comparative Example 4, except for adding 0.05 g (malic acid was 0.003 mol % relative to carboxyl group containing unsaturated monomer) of aqueous 50% malic acid solution (DL-malic acid, 50% by weight aqueous solution, Fuso Chemical Co., Ltd., Food additive grade) to the aqueous monomer solution (b') and changing the heating temperature to 180° C. in Comparative Example 4, to obtain water absorbent agent (17). The CRC, molecular weight of soluble component, and intrinsic viscosity of soluble component of water absorbent agent (17) are shown in Table 1. The YI value, Fe/L-as degradable soluble component, CRC and AAP of water absorbent agent (17) are shown in Table 14.

Example 18

The same treatment was applied as Comparative Example 4, except for the amount of polyethylene glycol diacrylate used being 2.564 g (0.080 mol % relative to carboxyl group containing unsaturated monomer), not adding an aqueous diethylenetriaminepentaacetic acid trisodium (DTPA 3Na) solution to the aqueous monomer solution (b'), adding 10.8 g (malic acid was 0.658 mol % relative to carboxyl group containing unsaturated monomer) of aqueous 50% malic acid solution (DL-malic acid, 50% by weight aqueous solution, Fuso Chemical Co., Ltd., Food additive grade), changing the heating temperature to 180° C., and not adding diethylenetriaminepentaacetic acid trisodium in Comparative Example 4, to obtain water absorbent agent (18). The CRC, molecular weight of soluble component, and intrinsic viscosity of soluble component of water absorbent agent (18) are shown in Table 1. Further, the malic acid content of water absorbent agent (18) was 0.98% by weight relative to the water absorbent agent. The YI value, Fe/L-as degradable soluble component, CRC and AAP of water absorbent agent (18) are shown in Table 14.

Comparative Example 11

An aqueous monomer solution (e') consisting of 300 parts by weight of acrylic acid, 100 parts by weight of aqueous 48% by weight sodium hydroxide solution, 0.61 parts by weight of polyethylene glycol diacrylate (average n of 9, average molecular weight of 523), 18.4 parts by weight of aqueous 0.1% by weight diethylenetriaminepentaacetic acid trisodium solution, and 336.5 parts by weight of deionized water was prepared.

After the aqueous monomer solution (e') adjusted to 38° C. was continuously supplied with a constant volume pump, 150.6 parts by weight of aqueous 48% by weight sodium hydroxide solution was further mixed successively in a static mixer to obtain aqueous monomer solution (e). The liquid temperature of the aqueous monomer solution (e) rose to 83° C. from the heat of neutralization.

Furthermore, 14.6 parts by weight of aqueous 4% by weight sodium persulfate solution was successively mixed with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (11). The resulting belt-shaped hydrogel (11) was successively out at equidistance in the width direction to the direction of progress of the polymerization belt so that the gel is out in a length of 300 mm to obtain hydrogel (11). The hydrogel (11) had CRC of 36.0 [g/g] and resin solid component of 48.1% by weight.

The hydrogel (11) obtained above was supplied to a screw extruder and ground. As the screw extruder, a meat chopper with a screw axel outer diameter of 86 mm comprising a perforated plate with a diameter of 100 mm, pour size of 8 mm, 54 pores, porosity of 36.1%, and a thickness of 10 mm at the tip was used. The hydrogel (11) was supplied at 4640 [g/min] and water vapor was simultaneously supplied at 83 [g/min] while the number of rotations of the screw axel of the meat chopper was 130 rpm. The temperature of the hydrogel (11) before gel grinding was 80° C., and the temperature of the ground gel after gel grinding, i.e., hydrogel particle (11), rose to 84° C.

The hydrogel particle (11) obtained in the gel grinding step had a resin solid component of 47.5% by weight, weight average particle diameter (D50) of 820 μm, and logarithmic standard deviation (σζ) of particle size distribution of 0.94.

Next, the hydrogel particle (11) was dispersed on a ventilation plate within one minute after the end of gel grinding (the temperature of the hydrogel particle (11) at this time was 80° C.) and dried for 30 minutes at 185° C. to obtain a dried polymer (11). The average wind speed of hot air was 1.0 [m/s] in the vertical direction with respect to the direction of progress of the ventilation belt. The wind speed of hot air was measured with Kanomax Japan Inc's constant temperature thermal anemometer, Anemomaster 6162.

Next, the entire amount of the dried polymer (11) obtained in the drying step was supplied to a three stage roll mill and pulverized (pulverizing step), and then classified with a JIS standard sieve with an opening of 710 μm and 175 μm to obtain pulverized comparative water absorbent resin (11) with an irregular pulverized shape. The comparative water absorbent resin (11) had a weight average particle diameter (D50) of 355 μm, logarithmic standard deviation (σζ) of particle size distribution of 0.32, CRC of 48.3 [g/g], and 0.4% by weight of 150 μm passing particles (ratio of particles passing through a sieve with an opening of 150 μm).

Next, to 100 parts by weight of the comparative water absorbent resin (11), (covalently bonding) surface crosslinking agent solution consisting of 0.025 parts by weight of ethylene glycol diglycidyl ether, 0.4 parts by weight of 1,4-butanediol, 0.6 parts by weight of propylene glycol, and 3.0 parts by weight of deionized water was homogenously mixed, and heated for about 30 minutes at 190° C. so that the CRC of the resulting comparative water absorbent resin particles (11) would be 38 to 39 g/g. The particles were then cooled, and the paint shaker test was conducted, and the damage equivalent to that in a manufacturing process was applied. An aqueous solution consisting of 1 parts by weight of water, and 0.01 parts by weight of diethylenetriaminepentaacetic acid trisodium was then homogenously mixed with 100 parts by weight of the comparative water absorbent resin particles (11). After drying for 1 hour at 60° C., the mixture was passed through a JIS standard sieve with an opening of 710 µm, and 0.4 parts by weight of silicon dioxide (product name: AEROSIL 200, Nippon Aerosil) was homogeneously added. The comparative water absorbent agent (11) was obtained in this manner. The CRC, molecular weight of soluble component, and intrinsic viscosity of soluble component of the comparative water absorbent agent (11) are shown in Table 1.

Example 19

The same treatment was applied as Comparative Example 11, except for the amount of polyethylene glycol diacrylate used being 0.78 parts by weight and adding 2.2 parts by weight of liquid malic acid (DL-malic acid, 50% by weight aqueous solution, Fuso Chemical Co., Ltd., Food additive grade) to the aqueous monomer solution (e') in Comparative Example 11, to obtain water absorbent agent (19). The CRC, molecular weight of soluble component, and intrinsic viscosity of soluble component of the water absorbent agent (19) are shown in Table 1. Further, the malic acid content of the water absorbent agent (19) was 0.29% by weight relative to the water absorbent agent.

Comparative Example 12

An aqueous monomer solution (f') consisting of 300 parts by weight of acrylic acid, 100 parts by weight of aqueous 48% by weight sodium hydroxide solution, 0.61 parts by weight of polyethylene glycol diacrylate (average n of 9, average molecular weight of 523), 18.4 parts by weight of aqueous 0.1% by weight diethylenetriaminepentaacetic acid trisodium solution, and 360.2 parts by weight of deionized water was prepared.

After the aqueous monomer solution (f') adjusted to 38° C. was continuously supplied with a constant volume pump, 150.6 parts by weight of aqueous 48% by weight sodium hydroxide solution was further mixed successively in a static mixer to obtain aqueous monomer solution (f). The liquid temperature of the aqueous monomer solution (f) rose to 81° C. from the heat of neutralization.

Furthermore, 14.6 parts by weight of aqueous 4% by weight sodium persulfate solution was successively mixed with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (12). The resulting belt-shaped hydrogel (12) was successively cut at equidistance in the width direction to the direction of progress of the polymerization belt so that the gel is cut in a length of 300 mm to obtain hydrogel (12). The hydrogel (12) had CRC of 36.7 [g/g] and resin solid component of 47.2% by weight.

The hydrogel (12) obtained above was supplied to a screw extruder and ground. As the screw extruder, a meat chopper with a screw axel outer diameter of 86 mm comprising a perforated plate with a diameter of 100 mm, pour size of 6.4 mm, 83 pores, and a thickness of 10 mm at the tip was used. The hydrogel (12) was supplied at 4640 [g/min] and water vapor was simultaneously supplied at 83 [g/min] while the number of rotations of the screw axel of the meat chopper was 130 rpm. The temperature of the hydrogel (12) before gel grinding was 80° C., and the temperature of the ground gel after gel grinding, i.e., hydrogel particle (12), rose to 84° C.

The hydrogel particle (12) obtained in the gel grinding step had a resin solid component of 47.5% by weight, weight average particle diameter (D50) of 820 µm, and logarithmic standard deviation (σζ) of particle size distribution of 0.94.

Next, the hydrogel particle (12) was dispersed on a ventilation plate within one minute after the end of gel grinding (the temperature of the hydrogel particle (12) at this time was 80° C.) and dried for 30 minutes at 185° C. to obtain a dried polymer (12). The average wind speed of hot air was 1.0 [m/s] in the vertical direction with respect to the direction of progress of the ventilation belt. The wind speed of hot air was measured with Kanomax Japan Inc's constant temperature thermal anemometer, Anemomaster 6162.

Next, the entire amount of the dried polymer (12) obtained in the drying step was supplied to a three stage roll mill and pulverized (pulverizing step), and then classified with a JIS standard sieve with an opening of 710 µm and 175 µm to obtain pulverized comparative water absorbent resin (12) with an irregular pulverized shape. The comparative water absorbent resin (12) had a weight average particle diameter (D50) of 366 µm, logarithmic standard deviation (σζ) of particle size distribution of 0.32, CRC of 49.4 [g/g], and 0.4% by weight of 150 µm passing particles (ratio of particles passing through a sieve with an opening of 150 µm).

Next, to 100 parts by weight of the comparative water absorbent resin (12), (covalently bonding) surface crosslinking agent solution consisting of 0.025 parts by weight of ethylene glycol diglycidyl ether, 0.4 parts by weight of 1,4-butanediol, 0.6 parts by weight of propylene glycol, and 3.0 parts by weight of deionized water was homogenously mixed, and heated for about 30 minutes at 190° C. so that the CRC of the resulting comparative water absorbent resin particles (12) would be 38 to 39 g/g. The particles were then cooled, and the paint shaker test was conducted, and the damage equivalent to that in a manufacturing process was applied. An aqueous solution consisting of 1 part by weight of water, and 0.01 parts by weight of diethylenetriaminepentaacetic acid trisodium was then homogenously mixed with 100 parts by weight of the comparative water absorbent resin particles (12). After drying for 1 hour at 60° C., the mixture was passed through a JIS standard sieve with an opening of 710 µm, and 0.4 parts by weight of silicon dioxide (product name: AEROSIL 200, Nippon Aerosil) was homogeneously added. The comparative water absorbent agent (12) was obtained in this manner. The CRC, molecular weight of soluble component, and intrinsic viscosity of soluble component of the comparative water absorbent agent (12) are shown in Table 1.

Example 20

The same treatment was applied as Comparative Example 12, except for adding 1.8 parts by weight of DL-malic acid (powder, Fuso Chemical Co., Ltd., Food additive grade) to the aqueous monomer solution (e') in Comparative Example 12, to obtain water absorbent agent (20). The CRC, molecular weight of soluble component, and intrinsic viscosity of soluble component of the water absorbent agent (20) are shown in Table 1. Further, the malic acid content of the water absorbent agent (20) was 0.49% by weight relative to the water absorbent agent.

Comparative Example 13

The same treatment was applied as Comparative Example 3, except for the amount of polyethylene glycol diacrylate used being 2.56 parts by weight (0.08 mol % relative to carboxyl group containing unsaturated monomer) and changing the amount of deionized water to 1511 g in Comparative Example 3, to obtain water absorbent agent comparative water absorbent agent (13). The CRC, molecular weight of soluble component, and intrinsic viscosity of soluble component of the water absorbent agent (13) are shown in Table 1.

Example 21

The same treatment was applied as Comparative Example 3, except for the amount of polyethylene glycol diacrylate used being 3.85 g (0.12 mol % relative to carboxyl group containing unsaturated monomer), the amount of deionizing water being 1510 g, and adding 10.81 g (malic acid was 0.658 mol % relative to carboxyl group containing unsaturated monomer) of liquid malic acid (DL-malic acid, 50% by weight aqueous solution, Fuso Chemical Co., Ltd., Food additive grade) to the aqueous monomer solution (b') in Comparative Example 3, to obtain water absorbent agent (21). The CRC, molecular weight of soluble component, and intrinsic viscosity of soluble component of the water absorbent agent (21) are shown in Table 1. The soluble component molecular weight reduction rate and tactile sensation evaluation results of comparative water absorbent agent (13) and water absorbent agent (21) are shown in Table 13.

TABLE 1

| | Polymerization | | | | | | Gel grinding | | | Absorbent evaluation result | | |
|---|---|---|---|---|---|---|---|---|---|---|---|---|
| | Monomer concentration (wt %) | Amount of internal cross-linking agent added (mol %) | Additive | Amount added (wt %) | Amount added (mol %) | Additive | Amount added (wt %) | Additive | Amount added (wt %) | Amount added (mol %) | CRC (g/g) | Molecular weight of soluble component (Daltons) | intrinsic viscosity (dl/g) |
| Comparative Example 1 | 38 | 0.06 | — | 0 | 0 | DTPA·3Na | 0.01 | — | — | — | 27.2 | 196329 | 1.42 |
| Comparative Example 2 | 38 | 0.093 | Malic acid | 0.25 | 0.165 | DTPA·3Na | 0.01 | — | — | — | 26.6 | 147432 | 1.12 |
| Comparative Example 3 | 45 | 0.055 | — | 0 | 0 | DTPA·3Na | 0.005 | — | — | — | 31.1 | 420247 | 2.85 |
| Comparative Example 4 | 45 | 0.035 | — | 0 | 0 | DTPA·3Na | 0.005 | — | — | — | 38 | 559057 | 3.71 |
| Comparative Example 5 | 45 | 0.025 | — | 0 | 0 | DTPA·3Na | 0.005 | — | — | — | 41.6 | 649366 | 4.41 |
| Comparative Example 6 | 39 | 0.035 | — | 0 | 0 | — | 0 | — | — | — | 37.4 | 453614 | 3.06 |
| Comparative Example 7 | 39 | 0.02 | — | 0 | 0 | — | — | — | — | — | 48.6 | 664786 | 4.45 |
| Comparative Example 8 | 40 | 0.047 | — | 0 | 0 | — | — | — | — | — | 38.5 | 451746 | 3.01 |
| Comparative Example 9 | 40 | 0.08 | — | 0 | 0 | — | — | — | — | — | 31.5 | 303703 | 2.31 |
| Example 1 | 45 | 0.075 | Malic acid | 1 | 0.658 | DTPA·3Na | 0.005 | — | — | — | 31.8 | 358722 | 2.46 |
| Example 2 | 45 | 0.07 | Na lactate | 0.5 | 0.394 | DTPA·3Na | 0.005 | — | — | — | 31 | 377956 | 2.60 |
| Example 3 | 45 | 0.068 | Malic acid | 0.5 | 0.329 | DTPA·3Na | 0.005 | — | — | — | 30.90 | 379246 | 2.56 |
| Example 4 | 45 | 0.047 | Malic acid | 0.5 | 3.329 | DTPA·3Na | 0.005 | — | — | — | 38.2 | 479613 | 3.23 |
| Example 5 | 45 | 0.045 | Na lactate | 0.4 | 0.315 | DTPA·3Na | 0.005 | — | — | — | 38.5 | 488454 | 3.29 |
| Example 6 | 45 | 0.045 | — | 0 | 0 | DTPA·3Na | 0.005 | Na lactate | 0.6 | 0.473 | 37.9 | 494544 | 3.31 |
| Example 7 | 45 | 0.045 | Malic acid | 0.5 | 0.329 | DTPA·3Na | 0.005 | — | — | — | 38.4 | 492392 | 3.31 |

TABLE 1-continued

| | Polymerization | | | | | | Gel grinding | | | Absorbent evaluation result | | |
|---|---|---|---|---|---|---|---|---|---|---|---|---|
| | Monomer concentration (wt %) | Amount of internal cross-linking agent added (mol %) | Additive | Amount added (wt %) | Amount added (mol %) | Additive | Amount added (wt %) | Additive | Amount added (wt %) | Amount added (mol %) | CRC (g/g) | Molecular weight of soluble component (Daltons) | intrinsic viscosity (dl/g) |
| Example 8 | 45 | 0.032 | Malic acid | 0.25 | 0.165 | DTPA•3Na | 0.005 | — | — | — | 41.4 | 578294 | 3.87 |
| Example 9 | 45 | 0.033 | — | 0 | 0 | DTPA•3Na | 0.005 | Malic acid | 0.5 | 0.329 | 42 | 567749 | 3.80 |
| Example 10 | 39 | 0.041 | Malic acid | 0.25 | 0.165 | — | — | — | — | — | 38 | 407150 | 2.75 |
| Example 11 | 39 | 0.04 | — | — | — | — | — | Malic acid | 0.5 | 0.329 | 37.6 | 414075 | 2.79 |
| Example 12 | 39 | 0.025 | Na lactate | 0.15 | 0.119 | — | — | — | — | — | 49.1 | 570811 | 3.78 |
| Example 13 | 40 | 0.065 | Malic acid | 0.5 | 0.329 | — | — | — | — | — | 37.4 | 372389 | 2.52 |
| Example 14 | 40 | 0.065 | — | — | — | — | — | Malic acid | 1 | 0.658 | 38.8 | 344806 | 2.38 |
| Example 15 | 40 | 0.1 | Na lactate | 0.6 | 0.473 | — | — | — | — | — | 32.4 | 218974 | 1.52 |
| Comparative Example 10 | 45 | 0.029 | — | — | — | DTPA•3Na | 0.005 | — | — | — | 39.7 | 611247 | 3.84 |
| Example 16 | 45 | 0.032 | Malic acid | 0.1 | 0.066 | DTPA•3Na | 0.005 | — | — | — | 39.2 | 564235 | 3.55 |
| Example 17 | 45 | 0.035 | Malic acid | 0.005 | 0.003 | DTPA•3Na | 0.005 | — | — | — | 37.2 | 547877 | 3.46 |
| Example 18 | 45 | 0.08 | Malic acid | 1 | 0.658 | — | — | — | — | — | 31.2 | 349632 | 2.27 |
| Comparative Example 11 | 40 | 0.028 | — | — | — | DTPA•3Na | 0.005 | — | — | — | 38.6 | 454689 | 2.90 |
| Example 19 | 40 | 0.036 | Malic acid | 0.3 | 0.197 | DTPA•3Na | 0.005 | — | — | — | 38.5 | 408263 | 2.62 |
| Comparative Example 12 | 39 | 0.028 | — | — | — | DTPA•3Na | 0.005 | — | — | — | 39.5 | 526394 | 3.33 |
| Example 20 | 39 | 0.04 | Malic acid | 0.5 | 0.329 | DTPA•3Na | 0.005 | — | — | — | 39.4 | 456253 | 2.91 |
| Comparative Example 13 | 23 | 0.08 | — | — | — | DTPA•3Na | 0.005 | — | — | — | 37.3 | 262384 | 1.74 |
| Example 21 | 23 | 0.12 | Malic acid | 1 | 0.658 | DTPA•3Na | 0.005 | — | — | — | 38.1 | 203860 | 1.33 |

TABLE 2

| | Polymerization | | Water absorbent agent evaluation result | | | |
|---|---|---|---|---|---|---|
| | Additive | Amount added (mol %) | CRC (g/g) | Molecular weight of soluble component (Daltons) | Soluble component molecular weight reduction ratio (%) | Tactile sensation evaluation |
| Comparative Example 1 | — | 0 | 27.2 | 196329 | — | 3 |
| Comparative Example 2 | Malic acid | 0.165 | 26.6 | 187432 | 4.5 | 2.9 |

TABLE 3

| | Polymerization | | | | Water absorbent agent evaluation result | | |
|---|---|---|---|---|---|---|---|
| | Additive | Amount added (wt %) | Amount added (mol %) | CRC (g/g) | Molecular weight of soluble component (Daltons) | Soluble component molecular weight reduction ratio (%) | Tactile sensation evaluation |
| Comparative Example 3 | DTPA•3Na | 0.005 | | 31.1 | 420247 | — | 3.0 |
| Example 1 | Malic acid | 1 | 0.658 | 31.8 | 358722 | 14.6 | 1.9 |
| | DTPA•3Na | 0.005 | 0.001 | | | | |
| Example 2 | Sodium lactate | 0.5 | 0.394 | 31 | 377956 | 10.1 | 2.2 |
| | DTPA•3Na | 0.005 | 0.001 | | | | |
| Example 3 | Malic acid | 0.5 | 0.329 | 30.9 | 379246 | 9.8 | 2.4 |
| | DTPA•3Na | 0.005 | 0.001 | | | | |
| Example 18 | Malic acid | 1 | 0.079 | 31.2 | 349632 | 16.8 | 1.6 |

TABLE 4

| | Polymerization | | | Gel grinding | | | | Water absorbent agent evaluation result | | |
|---|---|---|---|---|---|---|---|---|---|---|
| | Additive | Amount added (wt %) | Amount added (mol %) | Additive | Amount added (wt %) | Amount added (mol %) | CRC (g/g) | Molecular weight of soluble component (Daltons) | Soluble component molecular weight reduction ratio (%) | Tactile sensation evaluation |
| Comparative Example 4 | DTPA•3Na | 0.005 | | — | — | — | 38 | 559057 | — | 3.0 |
| Example 4 | Malic acid | 0.5 | 0.329 | — | — | — | 38.2 | 479613 | 14.2 | 1.4 |
| | DTPA•3Na | 0.005 | 0.001 | | | | | | | |
| Example 5 | Na lactate | 0.4 | 0.315 | — | — | — | 38.5 | 488454 | 12.6 | 1.7 |
| | DTPA•3Na | 0.005 | 0.001 | | | | | | | |
| Example 6 | DTPA•3Na | 0.005 | 0.001 | Na lactate | 0.6 | 0.473 | 37.9 | 494544 | 11.5 | 2.0 |
| Example 7 | Malic acid | 0.5 | 0.329 | — | — | — | 38.4 | 492392 | 11.9 | 2.1 |
| | DTPA•3Na | 0.005 | 0.001 | | | | | | | |
| Example 17 | Malic acid | 0.005 | 0.079 | — | — | — | 37.2 | 547877 | 2.0 | 2.6 |
| | DTPA•3Na | 0.005 | 0.003 | | | | | | | |

TABLE 5

| | Polymerization | | | Gel grinding | | | | Water absorbent agent evaluation result | | |
|---|---|---|---|---|---|---|---|---|---|---|
| | Additive | Amount added (wt %) | Amount added (mol %) | Additive | Amount added (wt %) | Amount added (mol %) | CRC (g/g) | Molecular weight of soluble component (Daltons) | Soluble component molecular weight reduction ratio (%) | Tactile sensation evaluation |
| Comparative Example 5 | — | — | — | — | — | — | 41.6 | 649366 | — | 3.0 |
| Example 8 | Malic acid | 0.25 | 0.165 | — | — | — | 41.4 | 578296 | 10.9 | 2.1 |
| Example 9 | — | — | — | Malic acid | 0.5 | 0.329 | 42.0 | 567749 | 12.6 | 1.9 |

TABLE 6

| | Polymerization | | | Gel grinding | | | Water absorbent agent evaluation result | | |
|---|---|---|---|---|---|---|---|---|---|
| | | | | | | | | Soluble component | |
| | | | | | | | Molecular weight of | molecular | |
| | Additive | Amount added (wt %) | Amount added (mol %) | Additive | Amount added (wt %) | Amount added (mol %) | CRC (g/g) | soluble component (Daltons) | weight reduction ratio (%) | Tactile sensation evaluation |
| Comparative Example 6 | — | — | — | — | — | — | 37.4 | 453614 | — | 3.0 |
| Example 10 | Malic acid | 0.25 | 0.165 | — | — | — | 38 | 407150 | 10.2 | 2.2 |
| Example 11 | — | — | — | Malic acid | 0.5 | 0.329 | 37.6 | 414075 | 8.7 | 2.3 |

TABLE 7

| | Polymerization | | | | Water absorbent agent evaluation result | | |
|---|---|---|---|---|---|---|---|
| | | | | | Molecular weight of | Soluble component molecular | |
| | Additive | Amount added (wt %) | Amount added (mol %) | CRC (g/g) | soluble component (Daltons) | weight reduction ratio (%) | Tactile sensation evaluation |
| Comparative Example 7 | — | — | — | 48.6 | 664786 | — | 3 |
| Example 12 | Sodium lactate | 0.15 | 0.119 | 49.1 | 570811 | 14.1 | 1.5 |

TABLE 8

| | Polymerization | | | Gel grinding | | | Water absorbent agent evaluation result | | |
|---|---|---|---|---|---|---|---|---|---|
| | | | | | | | | Soluble component | |
| | | | | | | | Molecular weight of | molecular | |
| | Additive | Amount added (wt %) | Amount added (mol %) | Additive | Amount added (wt %) | Amount added (mol %) | CRC (g/g) | soluble component (Daltons) | weight reduction ratio (%) | Tactile sensation evaluation |
| Comparative Example 8 | — | — | — | — | — | — | 38.5 | 451746 | — | 3.0 |
| Example 13 | Malic acid | 0.5 | 0.329 | — | — | — | 37.4 | 372389 | 17.6 | 1.2 |
| Example 14 | — | — | — | Malic acid | 1 | 0.658 | 38.8 | 344806 | 23.7 | 1.0 |

TABLE 9

| | Polymerization | | | Gel grinding | | | Water absorbent agent evaluation result | | |
|---|---|---|---|---|---|---|---|---|---|
| | | | | | | | | Soluble component | |
| | | | | | | | Molecular weight of | molecular | |
| | Additive | Amount added (wt %) | Amount added (mol %) | Additive | Amount added (wt %) | Amount added (mol %) | CRC (g/g) | soluble component (Daltons) | weight reduction ratio (%) | Tactile sensation evaluation |
| Comparative Example 9 | — | — | — | — | — | — | 31.5 | 303703 | — | 3.0 |
| Example 15 | Na lactate | 0.6 | 0.473 | — | — | — | 32.4 | 218974 | 27.9 | 1.0 |

TABLE 10

| | | Polymerization | | | Water absorbent agent evaluation result | | | |
| --- | --- | --- | --- | --- | --- | --- | --- | --- |
| | Additive | Amount added (wt %) | Amount added (mol %) | CRC (g/g) | Molecular weight of soluble component (Daltons) | Soluble component molecular weight reduction ratio (%) | Tactile sensation evaluation | |
| Comparative Example 10 | DTPA•3Na | 0.005 | 0.001 | 39.7 | 611247 | — | 3.0 | |
| Example 16 | Malic acid DTPA•3Na | 0.1 0.005 | 0.079 0.001 | 39.2 | 564235 | 7.7 | 2.4 | |

TABLE 11

| | | Polymerization | | | Water absorbent agent evaluation result | | | |
| --- | --- | --- | --- | --- | --- | --- | --- | --- |
| | Additive | Amount added (wt %) | Amount added (mol %) | CRC (g/g) | Molecular weight of soluble component (Daltons) | Soluble component molecular weight reduction ratio (%) | Tactile sensation evaluation | |
| Comparative Example 11 | DTPA•3Na | 0.005 | 0.001 | 38.6 | 454689 | — | 3.0 | |
| Example 19 | Malic acid DTPA•3Na | 0.3 0.005 | 0.197 0.001 | 38.5 | 408268 | 10.2 | 2.1 | |

TABLE 12

| | | Polymerization | | | Water absorbent agent evaluation result | | | |
| --- | --- | --- | --- | --- | --- | --- | --- | --- |
| | Additive | Amount added (wt %) | Amount added (mol %) | CRC (g/g) | Molecular weight of soluble component (Daltons) | Soluble component molecular weight reduction ratio (%) | Tactile sensation evaluation | |
| Comparative Example 12 | DTPA•3Na | 0.005 | 0.001 | 39.5 | 526394 | — | 3.0 | |
| Example 20 | Malic acid DTPA•3Na | 0.5 0.005 | 0.329 0.001 | 39.4 | 456253 | 13.3 | 1.5 | |

TABLE 13

| | | Polymerization | | | Water absorbent agent evaluation result | | | |
| --- | --- | --- | --- | --- | --- | --- | --- | --- |
| | Additive | Amount added (wt %) | Amount added (mol %) | CRC (g/g) | Molecular weight of soluble component (Daltons) | Soluble component molecular weight reduction ratio (%) | Tactile sensation evaluation | |
| Comparative Example 13 | DTPA•3Na | 0.005 | 0.001 | 37.3 | 262384 | — | 3.0 | |
| Example 21 | Malic acid DTPA•3Na | 1.0 0.005 | 0.658 0.001 | 38.1 | 203860 | 22.3 | 1.2 | |

Figure 2:
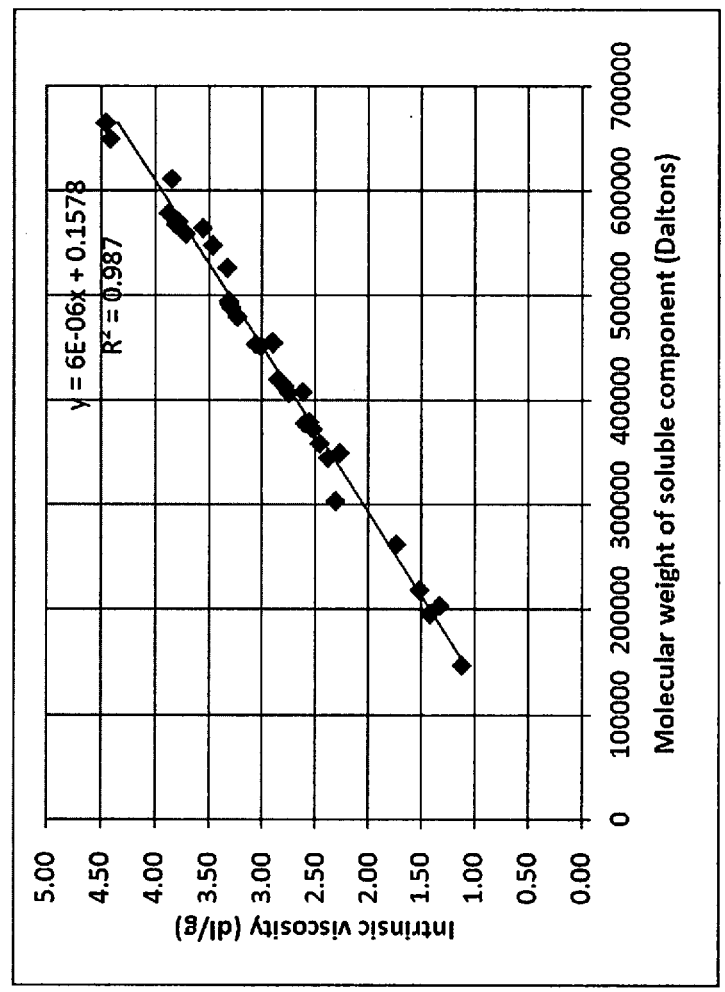
FIG. 2 is a graph plotting the relationship between the molecular weight of soluble component (Daltons) and intrinsic viscosity (dl/g) of soluble component in the water absorbent agents in the Examples and Comparative Examples of the present invention.

The relationship between centrifuge retention capacity (CRC) and the molecular weight of soluble component was plotted for various amounts of α-hydroxycarboxylic acid (0 mol %, 0.165 mol %, 0.329 mol %, and 0.658 mol % (Comparative Examples 3 to 5, Example 8, Examples 3, 4, and 7, and Example 1, respectively)) for the water absorbent agents in the Examples and Comparative Examples (FIG. 1). It was confirmed that compared to cases where an α-hydroxycarboxylic acid is not added (α-hydroxycarboxylic acid 0%), the molecular weight of soluble component tends to decrease when an α-hydroxycarboxylic acid was added. It was confirmed that the molecular weight of soluble component tends to decrease when an α-hydroxycarboxylic acid was added compared to cases where an α-hydroxycarboxylic acid is not added. Further, the molecular weight of soluble component has a linear relationship with the intrinsic viscosity of the soluble component (FIG. 2), so that it can be explained that an addition of an α-hydroxycarboxylic acid reduces the molecular weight of soluble component, which in turn reduces the intrinsic viscosity, resulting in reduced stickiness in tactile sensation evaluation.

Manufacturing Example 1

An aqueous monomer solution (f') was prepared by introducing and mixing 404.82 g of acrylic acid, 0.881 g (0.03 mol % relative to carboxyl group containing unsaturated monomer) of polyethylene glycol diacrylate (molecular weight 523) as an internal crosslinking agent, 2.48 g of aqueous 1.0% by weight diethylenetriaminepentaacetic acid trisodium (DTPA-3Na) solution, 166.8 g of aqueous 48.5% by weight sodium hydroxide solution, and 332.73 g of deionized water (ion exchange water) in a polypropylene container with a capacity of 2 liters.

Next, the aqueous monomer solution (f') was cooled while stirring. When the solution temperature reached 39.5° C., 166.80 g of aqueous 48.5% by weight sodium hydroxide solution adjusted to 40° C. was added and mixed to prepare an aqueous monomer solution (f). The temperature of the aqueous monomer solution (f) at this time rose to 76.9° C. due to the second stage of heat of neutralization immediately after the preparation. Deposits were observed immediately after starting to mix the aqueous 48.5% by weight sodium hydroxide solution, but the deposits gradually dissolved to yield a transparent and homogeneous solution.

Next, after adding 20.87 g of aqueous 3.5% by weight sodium persulfate solution to the aqueous monomer solution (f) being stirred, the mixture was immediately poured into a stainless steel vat (bottom surface 340×340 mm, height 25 mm, inner surface: Teflon(registered trademark) coating) in an open air system. The time from the start of second stage of neutralization until pouring the aqueous monomer solution (f) into the vat was 55 seconds. The vat was heated until the surface temperature was 40° C. using a hot plate (NEO HOTPLATE HI-1000/Iuchi Seleido).

The polymerization reaction started 60 seconds after the aqueous monomer solution (f) was poured into the vat. The polymerization reaction progressed, swelling and bubbling in all directions while generating water vapor. The solution then contracted to a size that was slightly larger than the vat. The crosslinked hydrogel polymer (hereinafter, referred to as "hydrogel") (14) was retrieved after 3 minutes from the start of the polymerization reaction. The series of operations were performed in an open air system.

The hydrogel (14) obtained in the polymerization reaction was ground using a meat chopper (HL-3225N, plate pour diameter; 10.0 mm/Remacom) to prepare particular hydrogel (14).

The amount of the hydrogel (14) supplied was 230 g/min. Gel was ground while adding deionized water adjusted to 90° C. at 50 g/min and simultaneously supplying the hydrogel (14).

The hydrogel particle (14) obtained through the operation was spread on a stainless steel mesh with an opening of 850 µm and dried with hot air for 30 minutes at 180° C. The dried polymer (14) obtained by the drying operation was pulverized using a roll mill (WML roll mill/Inokuchi Giken) and classified using a JIS sieve with an opening of 710 µm and 45 µm.

A surface crosslinking agent solution (14) consisting of 0.024 part by weight of diethylene glycol diglycidyl ether (product name: Denacol EX-810, Nagase ChemteX Corporation), 0.308 parts by weight of ethylene carbonate, 0.515 parts by weight of propylene glycol, and 2.08 parts by weight of deionized water (ion exchange water) was added to and homogeneously mixed with 100 parts by weight of water absorbent resin powder (14). The mixture was then heated for 40 minutes at 1800° C. for surface crosslinking.

After the heating treatment, the resulting water absorbent resin particles (14) were crushed until they passed through the JIS standard sieve with an opening of 850 µm.

An aqueous solution consisting of 0.01 parts by weight of DTPA·3Na and 1.0 part by weight of deionized water (ion exchange water) was added to and homogeneously mixed with the resulting water absorbent agent for granulation. After heating for 45 minutes at 60° C. under windless conditions, the particles were crushed until they passed through a JIS standard sieve with an opening of 850 µm to obtain granulated water absorbent resin particles (14).

0.3 parts by weight of silica (product name Reolosil QS-20, Tokuyama) was mixed with 100 parts by mass of the granulated water absorbent resin particles (14). This was performed by placing 30 g of water absorbent resin with silica in a mayonnaise jar with a capacity of 225 mL and shaking the jar with a paint shaker (Toyo Seiki) for 3 minute to obtain water absorbent agent (14).

Manufacturing Example 2

In Manufacturing Example 1, surface crosslinking was performed in accordance with the following without mixing in silica to obtain water absorbent resin particles (15).

For surface crosslinking, a surface crosslinking agent solution (2) consisting of 0.025 part by weight of diethylene glycol diglycidyl ether (product name: Denacol EX-810, Nagase ChemteX Corporation), 1.5 parts by weight of propylene glycol, and 3.5 parts by weight of deionized water (ion exchange water) was added to and homogeneously mixed with 100 parts by weight of water absorbent resin powder (15). The mixture was then heated for 40 minutes at 100° C.

Comparative Example 14

Comparative water absorbent agent (14) was obtained by the method in Manufacturing Example 1. The performance of comparative water absorbent agent (14) is shown in Table 14.

Comparative Example 15

Water absorbent resin particles (15) obtained by the method in Manufacturing Example 2 are comparative water absorbent agent (15). The performance of comparative water absorbent agent (15) is shown in Table 14.

Comparative Example 16

The same operation was performed as Manufacturing Example 1, except for changing the amount of polyethylene glycol diacrylate added from 0.03 mol % to 0.04 mol %, changing the amount of diethylenetriaminepentaacetic acid trisodium (DTPA·3Na) added upon granulation from 0.01 to 0.1 part by weight, and not mixing in silica in Manufacturing Example 1. The resulting water absorbent resin particles are comparative water absorbent agent (16). The performance of comparative water absorbent agent (16) is shown in Table 14.

Example 22

The same operation was performed as Manufacturing Example 1, except for adding 0.33 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.03 parts by weight, and not mixing in silica in Manufacturing Example 1. The resulting water absorbent resin particles are water absorbent agent (22). The performance of water absorbent agent (22) is shown in Table 14.

Example 23

The same operation was performed as Manufacturing Example 1, except for changing the amount of diethylenetriaminepentaacetic acid trisodium (DTPA-3Na) added to the aqueous monomer solution (f') from 2.48 to 9.90 g. adding 0.83 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.03 parts by weight, and not mixing in silica in Manufacturing Example 1. The resulting water absorbent resin particles are water absorbent agent (23). The performance of water absorbent agent (23) is shown in Table 14.

Example 24

The same operation was performed as Manufacturing Example 1, except for changing the amount of polyethylene glycol diacrylate added from 0.03 mol % to 0.032 mol %, changing the amount of diethylenetriaminepentaacetic acid trisodium (DTPA·3Na) added to the aqueous monomer solution (f') from 2.48 to 9.90 g, adding 1.65 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.02 parts by weight, and not mixing in silica in Manufacturing Example 1. The resulting water absorbent resin particles are water absorbent agent (24). The performance of water absorbent agent (24) is shown in Table 14.

Example 25

The same operation was performed as Manufacturing Example 1, except for changing the amount of polyethylene glycol diacrylate added from 0.03 mol % to 0.032 mol %, adding 1.65 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.09 parts by weight, and not mixing in silica in Manufacturing Example 1. The resulting water absorbent resin particles are water absorbent agent (25). The performance of water absorbent agent (25) is shown in Table 14.

Example 26

The same operation was performed as Manufacturing Example 2, except for changing the amount of polyethylene glycol diacrylate added from 0.03 mol % to 0.032 mol %, adding 1.65 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), and changing the amount of diethylenetriaminepentaacetic acid trisodium (DTPA·3Na) added upon granulation from 0.01 to 0.03 parts by weight in Manufacturing Example 2. The resulting water absorbent resin particles are water absorbent agent (26). The performance of water absorbent agent (26) is shown in Table 14.

Example 27

The same operation was performed as Manufacturing Example 1, except for changing the amount of polyethylene glycol diacrylate added from 0.03 mol % to 0.045 mol % and adding 1.65 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f') in Manufacturing Example 1. The resulting water absorbent resin particles are water absorbent agent (27). The performance of water absorbent agent (27) is shown in Table 14.

Example 28

The same operation was performed as Manufacturing Example 1, except for changing the amount of polyethylene glycol diacrylate added from 0.03 mol % to 0.035 mol %, adding 3.3 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing diethylenetriaminepentaacetic acid trisodium (DTPA·3Na) upon granulation from 0.01 to 0.03 parts by weight, and not mixing in silica in Manufacturing Example 1. The resulting water absorbent resin particles are water absorbent agent (28). The performance of water absorbent agent (28) is shown in Table 14.

Example 29

The same operation was performed as Manufacturing Example 2, except for changing the amount of polyethylene glycol diacrylate added from 0.03 mol % to 0.035 mol %, changing the amount of diethylenetriaminepentaacetic acid trisodium (DTPA·3Na) added to the aqueous monomer solution (f') from 2.48 to 9.90 g, adding 3.3 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.03 parts by weight, and mixing in tricalcium phosphate in Manufacturing Example 2. The resulting water absorbent resin particles are water absorbent agent (29). The performance of water absorbent agent (29) is shown in Table 14.

Example 30

The same operation was performed as Manufacturing Example 2, except for changing the amount of polyethylene glycol diacrylate added from 0.03 mol % to 0.045 mol %, adding 8.25 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA 3Na) added upon granulation from 0.01 to 0.03 parts by weight, and mixing in hydrotalcite (product name: DHT-6, Kyowa Chemical Industry Co., Ltd., $Mg_6Al_2(OH)_{16}CO_3 \cdot 4H_2O$ [x=0.25, m=0.50 in general formula (1)], volume average particle diameter 0.5 μm) in Manufacturing Example 2. The resulting water absorbent resin particles are water absorbent agent (30). The performance of water absorbent agent (30) is shown in Table 14.

Example 31

The same operation was performed as Example 28, except for mixing in silica in Example 28. The resulting water absorbent resin particles are water absorbent agent (31). The performance of water absorbent agent (31) is shown in Table 14.

Example 32

The same operation was performed as Manufacturing Example 1, except for changing the amount of polyethylene glycol diacrylate added from 0.03 mol % to 0.045 mol %, changing the amount of diethylenetriaminepentaacetic acid trisodium (DTPA·3Na) added to the aqueous monomer solution (f') from 2.48 to 9.90 g, adding 8.25 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.03 parts by weight, and not mixing in silica in Manufacturing Example 1. The resulting water absorbent resin particles are water absorbent agent (32). The performance of water absorbent agent (32) is shown in Table 14.

Example 33

The same operation was performed as Manufacturing Example 1, except for changing the amount of polyethylene glycol diacrylate added from 0.03 mol % to 0.045 mol %, adding 8.25 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA 3Na) added upon granulation from 0.01 to 0.09 parts by weight, and not mixing in silica in Manufacturing Example 1. The resulting water absorbent resin particles are water absorbent agent (33). The performance of water absorbent agent (33) is shown in Table 14.

Example 34

The same operation was performed as Manufacturing Example 1, except for changing the amount of polyethylene glycol diacrylate added from 0.03 mol % to 0.055 mol %, changing the amount of diethylenetriaminepentaacetic acid trisodium (DTPA·3Na) added to the aqueous monomer solution (f') from 2.48 to 9.90 g, adding 12.38 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing diethylenetriaminepentaacetic acid trisodium (DTPA·3Na) upon granulation from 0.01 to 0.03 parts by weight, and not mixing in silica in Manufacturing Example 1. The resulting water absorbent resin particles are water absorbent agent (34). The performance of water absorbent agent (34) is shown in Table 14.

Example 35

The same operation was performed as Manufacturing Example 1, except for changing the amount of polyethylene glycol diacrylate added from 0.03 mol % to 0.06 mol %, adding 16.5 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA 3Na) added upon granulation from 0.01 to 0.03 parts by weight, and not mixing in silica in Manufacturing Example 1. The resulting water absorbent resin particles are water absorbent agent (35). The performance of water absorbent agent (35) is shown in Table 14.

Example 36

The same operation was performed as Manufacturing Example 1, except for changing the amount of polyethylene glycol diacrylate added from 0.03 mol % to 0.08 mol %, not adding diethylenetriaminepentaacetic acid trisodium (DTPA·3Na) to the aqueous monomer solution (f'), adding 33.0 g of aqueous 30% by weight D,L-malic acid solution (DL-malic acid, 50% by weight aqueous solution, Fuso Chemical Co., Ltd., Food additive grade, was used by adjusting the concentration with ion exchange water) to the aqueous monomer solution (f'), changing the amount of diethylenetriaminepentaacetic acid trisodium (DTPA·3Na) added upon granulation from 0.01 to 0.03 parts by weight, and not mixing in silica in Manufacturing Example 1. The resulting water absorbent resin particles are water absorbent agent (36). The performance of water absorbent agent (36) is shown in Table 14.

Example 37

The same operation was performed as Manufacturing Example 1, except for changing the amount of polyethylene glycol diacrylate added from 0.03 mol % to 0.035 mol %, adding 1.65 g of aqueous 30% by weight lactic acid solution to the aqueous monomer solution (f'), changing the amount of diethylenetriaminepentaacetic acid trisodium (DTPA·3Na) added upon granulation from 0.01 to 0.05 parts by weight, and not mixing in silica in Manufacturing Example 1. The resulting water absorbent resin particles are water absorbent agent (37). The performance of water absorbent agent (37) is shown in Table 14.

TABLE 14

| | | | Polymerization | | | | | | Granulation Additive③ | |
|---|---|---|---|---|---|---|---|---|---|---|
| | | | Cross-linking agent | Additive① | | Additive② | | | | |
| | | | Amount added mol % | Type | Amount added wt % | Type | Amount added mol % | Amount added wt % | Type | Amount added wt % |
| Manufacturing Example 1 | Comparative Example 14 | Comparative absorbent 14 | 0.03 | DTPA | 0.005 | — | — | — | DTPA | 0.01 |
| Manufacturing Example 2 | Comparative Example 15 | Comparative absorbent 15 | 0.03 | DTPA | 0.005 | — | — | — | DTPA | 0.01 |
| Manufacturing Example 1 | Comparative Example 16 | Comparative absorbent 16 | 0.04 | DTPA | 0.005 | — | — | — | DTPA | 0.1 |
| — | Example 16 | Absorbent 16 | 0.032 | DTPA | 0.005 | Malic acid | 0.066 | 0.1 | — | — |
| — | Example 17 | Absorbent 17 | 0.035 | DTPA | 0.005 | Malic acid | 0.003 | 0.005 | DTPA | 0.03 |
| — | Example 18 | Absorbent 18 | 0.08 | — | — | Malic acid | 0.658 | 1 | — | — |
| Manufacturing Example 1 | Example 22 | Absorbent 22 | 0.03 | DTPA | 0.005 | Malic acid | 0.013 | 0.02 | DTPA | 0.03 |
| Manufacturing Example 1 | Example 23 | Absorbent 23 | 0.03 | DTPA | 0.02 | Malic acid | 0.033 | 0.05 | DTPA | 0.03 |
| Manufacturing Example 1 | Example 24 | Absorbent 24 | 0.032 | DTPA | 0.02 | Malic acid | 0.066 | 0.1 | DTPA | 0.02 |
| Manufacturing Example 1 | Example 25 | Absorbent 25 | 0.032 | DTPA | 0.005 | Malic acid | 0.066 | 0.1 | DTPA | 0.09 |
| Manufacturing Example 2 | Example 26 | Absorbent 26 | 0.032 | DTPA | 0.005 | Malic acid | 0.066 | 0.1 | DTPA | 0.03 |
| Manufacturing Example 1 | Example 27 | Absorbent 27 | 0.045 | DTPA | 0.005 | Malic acid | 0.066 | 0.1 | DTPA | 0.01 |
| Manufacturing Example 1 | Example 28 | Absorbent 28 | 0.035 | DTPA | 0.005 | Malic acid | 0.132 | 0.2 | DTPA | 0.03 |
| Manufacturing Example 2 | Example 29 | Absorbent 29 | 0.035 | DTPA | 0.02 | Malic acid | 0.132 | 0.2 | DTPA | 0.03 |
| Manufacturing Example 2 | Example 30 | Absorbent 30 | 0.045 | DTPA | 0.005 | Malic acid | 0.329 | 0.5 | DTPA | 0.03 |
| Manufacturing Example 1 | Example 31 | Absorbent 31 | 0.035 | DTPA | 0.005 | Malic acid | 0.132 | 0.2 | DTPA | 0.03 |
| Manufacturing Example 1 | Example 32 | Absorbent 32 | 0.045 | DTPA | 0.02 | Malic acid | 0.329 | 0.5 | DTPA | 0.03 |
| Manufacturing Example 1 | Example 33 | Absorbent 33 | 0.045 | DTPA | 0.005 | Malic acid | 0.329 | 0.5 | DTPA | 0.09 |
| Manufacturing Example 1 | Example 34 | Absorbent 34 | 0.055 | DTPA | 0.02 | Malic acid | 0.494 | 0.75 | DTPA | 0.03 |
| Manufacturing Example 1 | Example 35 | Absorbent 35 | 0.06 | DTPA | 0.005 | Malic acid | 0.658 | 1.0 | DTPA | 0.03 |
| Manufacturing Example 1 | Example 36 | Absorbent 36 | 0.08 | — | — | Malic acid | 1.32 | 2.0 | DTPA | 0.03 |
| Manufacturing Example 1 | Example 37 | Absorbent 37 | 0.035 | DTPA | 0.005 | Lactic acid | 0.079 | 0.1 | DTPA | 0.05 |

| | | | Post additive Additive④ | | Performance | | | | |
|---|---|---|---|---|---|---|---|---|---|
| | | | | | concentration error zone YI | Urine resistance Fe/L-as evaluation soluble component wt % | Water absorbing performance | | |
| | | | Type | Amount added wt % | | | CRC g/g | AAP 2.1 kPa g/g | |
| Manufacturing Example 1 | Comparative Example 14 | Comparative Absorbent 14 | Silica | 0.3 | 27.5 | 49 | 38.5 | 28 | |
| Manufacturing Example 2 | Comparative Example 15 | Comparative Absorbent 15 | — | — | 27.8 | 45 | 38 | 32.1 | |
| Manufacturing Example 1 | Comparative Example 16 | Comparative Absorbent 16 | — | — | 26.5 | 16 | 34.8 | 33.1 | |
| — | Example 16 | Absorbent 16 | — | — | 28.5 | 57 | 38.3 | 32.8 | |
| — | Example 17 | Absorbent 17 | — | — | 27 | 22 | 36.1 | 32.8 | |
| — | Example 18 | Absorbent 18 | — | — | 20 | 65 | 36.8 | 31 | |

TABLE 14-continued

| | | | | | | | | |
|---|---|---|---|---|---|---|---|---|
| Manufacturing Example 1 | Example 22 | Absorbent 22 | — | — | 25.6 | 32 | 38.3 | 32.9 |
| Manufacturing Example 1 | Example 23 | Absorbent 23 | — | — | 25.1 | 31 | 37.5 | 33.4 |
| Manufacturing Example 1 | Example 24 | Absorbent 24 | — | — | 24.4 | 29 | 38 | 32.8 |
| Manufacturing Example 1 | Example 25 | Absorbent 25 | — | — | 20.2 | 15 | 37.2 | 32.8 |
| Manufacturing Example 2 | Example 26 | Absorbent 26 | — | — | 24 | 28 | 38.8 | 32.2 |
| Manufacturing Example 1 | Example 27 | Absorbent 27 | Silica | 0.3 | 24 | 29 | 32.3 | 29.4 |
| Manufacturing Example 1 | Example 28 | Absorbent 28 | — | — | 23 | 22 | 38.2 | 33.1 |
| Manufacturing Example 2 | Example 29 | Absorbent 29 | 3Ca phosphate | 0.5 | 23 | 22 | 38.1 | 32.4 |
| Manufacturing Example 2 | Example 30 | Absorbent 30 | DHT-5 | 0.4 | 23.3 | 22 | 38 | 31.3 |
| Manufacturing Example 1 | Example 31 | Absorbent 31 | Silica | 0.3 | 23 | 22 | 37.7 | 28.1 |
| Manufacturing Example 1 | Example 32 | Absorbent 32 | — | — | 18.8 | 17 | 38.4 | 32.6 |
| Manufacturing Example 1 | Example 33 | Absorbent 33 | — | — | 18.5 | 15 | 37.9 | 33.2 |
| Manufacturing Example 1 | Example 34 | Absorbent 34 | — | — | 17.8 | 25 | 37.5 | 32.6 |
| Manufacturing Example 1 | Example 35 | Absorbent 35 | — | — | 17.6 | 24 | 37.4 | 32.5 |
| Manufacturing Example 1 | Example 36 | Absorbent 36 | — | — | 17 | 32 | 37.8 | 29.8 |
| Manufacturing Example 1 | Example 37 | Absorbent 37 | — | — | 21.9 | 19 | 38.2 | 32.8 |

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application 2016-063762 (filed on Mar. 28, 2016) and Japanese Patent Application No. 2016-194920 (Sep. 30, 2016). The entire content thereof is incorporated herein by reference.

INDUSTRIAL APPLICABILITY

The present invention can provide a water absorbent agent with a high fluid retention capacity, capable of reducing stickiness after absorbing a liquid upon use as a sanitation material, or improves both strong urine resistance and resistance to coloration over time. The present invention can be utilized as sanitation articles such as paper diapers and sanitary napkins, as well as in various additional fields such as pet sheets and water stopping materials.

The invention claimed is:

1. A method of manufacturing a water absorbent agent with a centrifuge retention capacity (CRC) of 31 g/g or greater, comprising of subjecting an aqueous monomer solution comprising an acrylic acid (salt) to a polymerization step, a drying step, and a surface crosslinking step, wherein the method comprises a step of adding an α-hydroxycarboxylic acid (salt) before the drying step, wherein a peak temperature during a polymerization reaction of the aqueous monomer solution in the polymerization step is 85° C. or greater, the polymerization step is performed in the presence of a chelating agent, and the method further comprising the step of adding the chelating agent after the drying step.

2. The method of claim 1, wherein the α-hydroxycarboxylic acid (salt) is added before or during the polymerization step.

3. The method of claim 1, wherein an amount of the α-hydroxycarboxylic acid (salt) to be added is 0.010 to 4.0 mol % with respect to the acrylic acid (salt).

4. The method of claim 1, wherein the α-hydroxycarboxylic acid (salt) is one or more selected from the group consisting of a malic acid (salt) and a lactic acid (salt).

5. The method of claim 1, wherein a centrifuge retention capacity (CRC) before crosslinking of the water absorbent agent is greater than 34 g/g.

6. The method of claim 1, wherein an amount of a soluble component of the water absorbent agent is 10% by weight or greater and 30% by weight or less.

7. The method of claim 1, wherein a molecular weight of a soluble component of the water absorbent agent is 200,000 Daltons or greater and 700,000 Daltons or less.

8. The method of claim 1, further comprising a step of adding at least one selected from the group consisting of silicon dioxide, phosphate, and hydrotalcite as a moisture absorption fluidity improving agent after the drying step.

* * * * *